(12) United States Patent
Downey et al.

(10) Patent No.: US 12,220,532 B2
(45) Date of Patent: Feb. 11, 2025

(54) PATIENT INTERFACE AND ASPECTS THEREOF

(71) Applicant: Fisher & Paykel Healthcare Limited, Auckland (NZ)

(72) Inventors: Jonathan Mark Downey, Auckland (NZ); Thomas Mark Richardson, Auckland (NZ); Craig Robert Prentice, Auckland (NZ); Richard John Boyes, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 174 days.

(21) Appl. No.: 17/539,721

(22) Filed: Dec. 1, 2021

(65) Prior Publication Data

US 2022/0249793 A1    Aug. 11, 2022

Related U.S. Application Data

(63) Continuation of application No. 16/094,723, filed as application No. PCT/IB2017/052292 on Apr. 21, 2017, now Pat. No. 11,229,761.

(60) Provisional application No. 62/326,636, filed on Apr. 22, 2016.

(51) Int. Cl.
 *A61M 16/06* (2006.01)
(52) U.S. Cl.
 CPC .... *A61M 16/0611* (2014.02); *A61M 16/0666* (2013.01); *A61M 16/0683* (2013.01)
(58) Field of Classification Search
 CPC ............. A61M 16/0611; A61M 16/0666
 See application file for complete search history.

(56) References Cited

U.S. PATENT DOCUMENTS

| | | | |
|---|---|---|---|
| 4,739,755 A | 4/1988 | White et al. | |
| 4,782,832 A | 11/1988 | Trimble et al. | |
| 6,431,172 B1 | 8/2002 | Bordewick | |
| 7,987,850 B2 | 8/2011 | Zollinger et al. | |
| 9,205,215 B2 | 12/2015 | McAuley et al. | |
| 10,456,540 B2* | 10/2019 | Eves ................ | A61M 16/0683 |
| 11,097,077 B2 | 8/2021 | Richardson et al. | |
| 11,229,761 B2 | 1/2022 | Downey et al. | |

(Continued)

FOREIGN PATENT DOCUMENTS

| | | |
|---|---|---|
| CA | 2919449 | 4/2022 |
| EP | 2022528 | 2/2009 |

(Continued)

OTHER PUBLICATIONS

Farkas et al., "Geography of the nose: a morphometric study", Aesthetic Plastic Surgery, vol. 10, No. 4, pp. 191-223, 1986.

(Continued)

*Primary Examiner* — Joseph D. Boecker
*Assistant Examiner* — Thomas W Greig
(74) *Attorney, Agent, or Firm* — VIA LLP

(57) ABSTRACT

A patient interface can have a frame supporting a sealing member. Various features of the sealing member can improve comfort and sealing performance in the context of forming seals with the nares of a user, as well as contact with other facial surfaces. The sealing member can include convex portions, concave portions and thickness variations for providing various sealing, comfort, and deformability effects.

14 Claims, 73 Drawing Sheets

(56) References Cited

U.S. PATENT DOCUMENTS

| | | | |
|---|---|---|---|
| 11,806,475 | B2 | 11/2023 | Richardson et al. |
| 2005/0028822 | A1* | 2/2005 | Sleeper .............. A61M 16/0833 128/207.18 |
| 2007/0125387 | A1* | 6/2007 | Zollinger ........... A61M 16/0611 128/207.18 |
| 2007/0163600 | A1 | 7/2007 | Hoffman |
| 2008/0060657 | A1* | 3/2008 | McAuley ............ A61M 16/024 128/207.18 |
| 2009/0044808 | A1* | 2/2009 | Guney ............... A61M 16/0875 128/207.18 |
| 2009/0217929 | A1 | 9/2009 | Kwok et al. |
| 2010/0229868 | A1 | 9/2010 | Rummery et al. |
| 2011/0146685 | A1 | 6/2011 | Allan et al. |
| 2012/0067349 | A1 | 3/2012 | Barlow et al. |
| 2012/0132209 | A1 | 5/2012 | Rummery et al. |
| 2012/0204870 | A1 | 8/2012 | McAuley et al. |
| 2012/0266890 | A1* | 10/2012 | Baecke ................. A61M 16/08 128/207.13 |
| 2013/0133664 | A1* | 5/2013 | Startare ............. A61M 16/0666 128/206.24 |
| 2013/0186403 | A1 | 7/2013 | Chang |
| 2014/0174446 | A1 | 6/2014 | Prentice et al. |
| 2014/0366885 | A1* | 12/2014 | Haibach ............ A61M 16/0622 128/206.24 |
| 2016/0095996 | A1* | 4/2016 | Gusky ............... A61M 16/0816 128/205.25 |
| 2016/0184544 | A1* | 6/2016 | Patel ................. A61M 16/0683 128/206.24 |
| 2018/0078725 | A1 | 3/2018 | Richardson et al. |
| 2019/0022343 | A1 | 1/2019 | Kooij et al. |
| 2019/0117923 | A1 | 4/2019 | Downey et al. |
| 2021/0386950 | A1 | 12/2021 | Downey et al. |
| 2024/0082525 | A1 | 3/2024 | Downey et al. |

FOREIGN PATENT DOCUMENTS

| | | |
|---|---|---|
| EP | 2679266 | 1/2014 |
| EP | 2679267 | 1/2014 |
| WO | WO 2006/130903 | 12/2006 |
| WO | WO 2007/064660 | 6/2007 |
| WO | WO 2008/100860 | 8/2008 |
| WO | WO 2009/151344 | 12/2009 |
| WO | WO 2012/020359 | 2/2012 |
| WO | WO 2013/168134 | 11/2013 |
| WO | WO 2014/110626 | 4/2014 |
| WO | WO 2014/155329 | 10/2014 |
| WO | WO 2015/009172 | 1/2015 |
| WO | WO 2015/020540 | 2/2015 |
| WO | WO 2016/043607 | 3/2016 |
| WO | WO 2016/157040 | 10/2016 |

OTHER PUBLICATIONS

Australian Government, Examination Report No. 1 for Standard Patent Application, Application No. 2016241413, dated Nov. 15, 2019, in 5 pages.
European Patent Office, Extended European Search Report, Application No. PCT/IB2017/052292, dated Nov. 12, 2019, in 5 pages.
European Search Report and Search Opinion for Application No. 16 771 484.9.
European Patent Office, Extended European Search Report, Application No. 20191302.7-1122, dated Oct. 29, 2020, in 9 pages.
European Search Report, PCT/IB2016/051665, dated Nov. 13, 2018, in 9 pages.
International Search Report, Application No. PCT/IB2016/051665, dated Jun. 7, 2016, in 4 pages.
International Search Report for International Application No. PCT/IB2017/052292 mailed on Aug. 7, 2017.

* cited by examiner

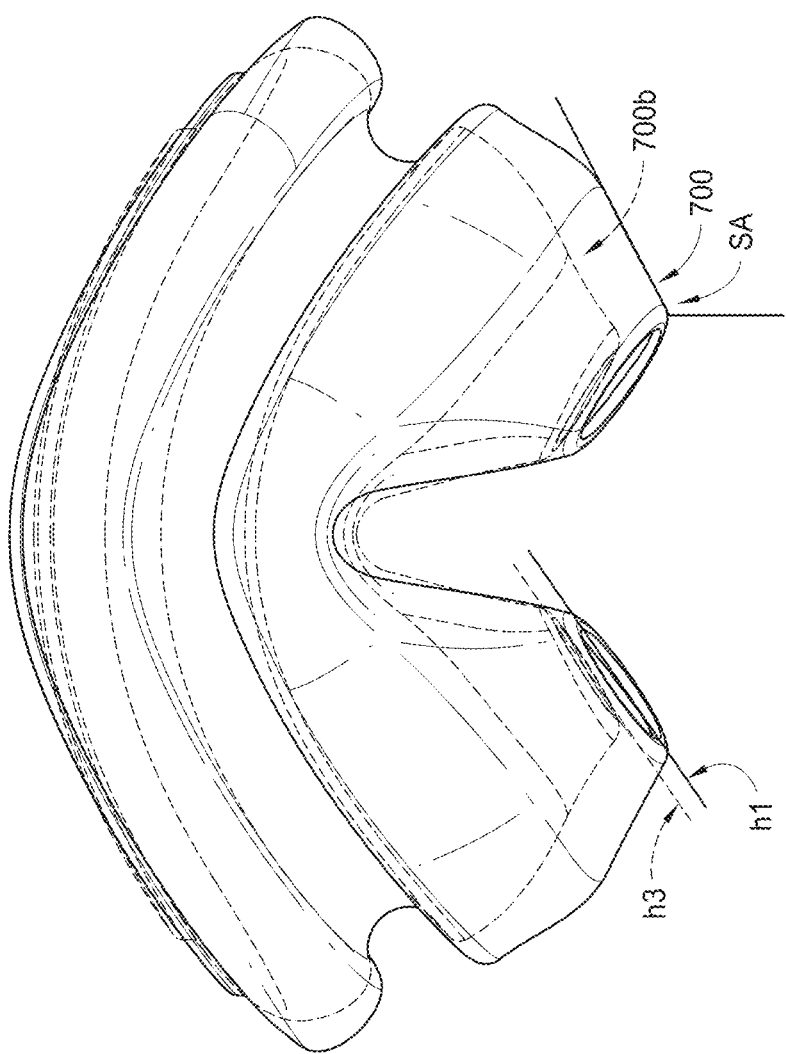

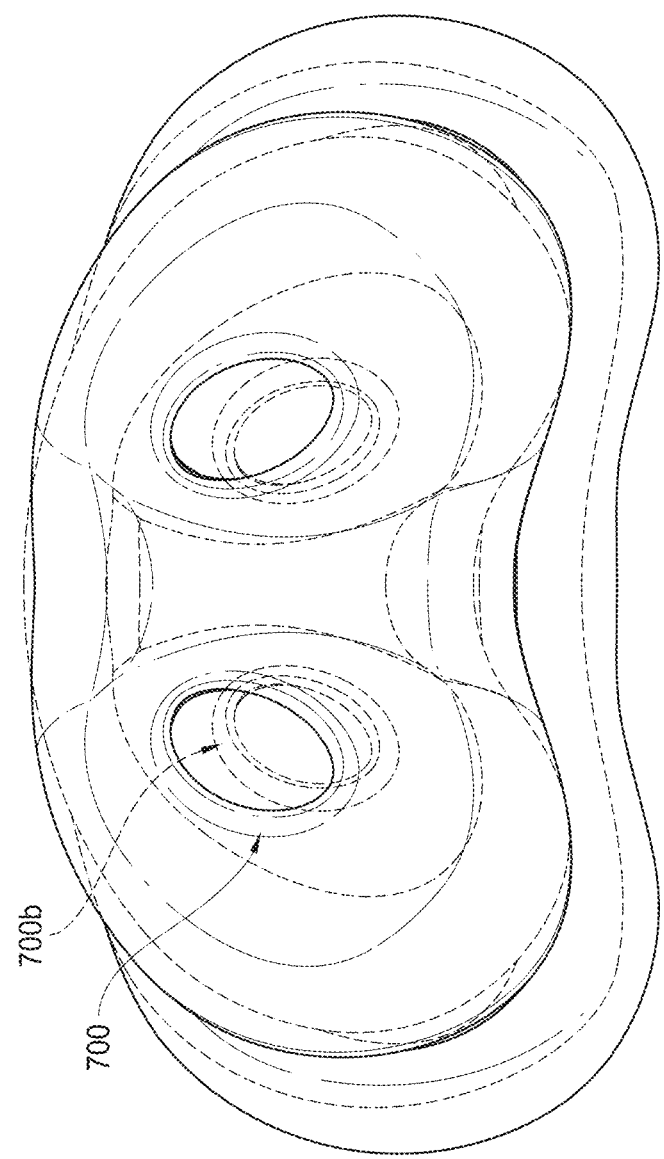

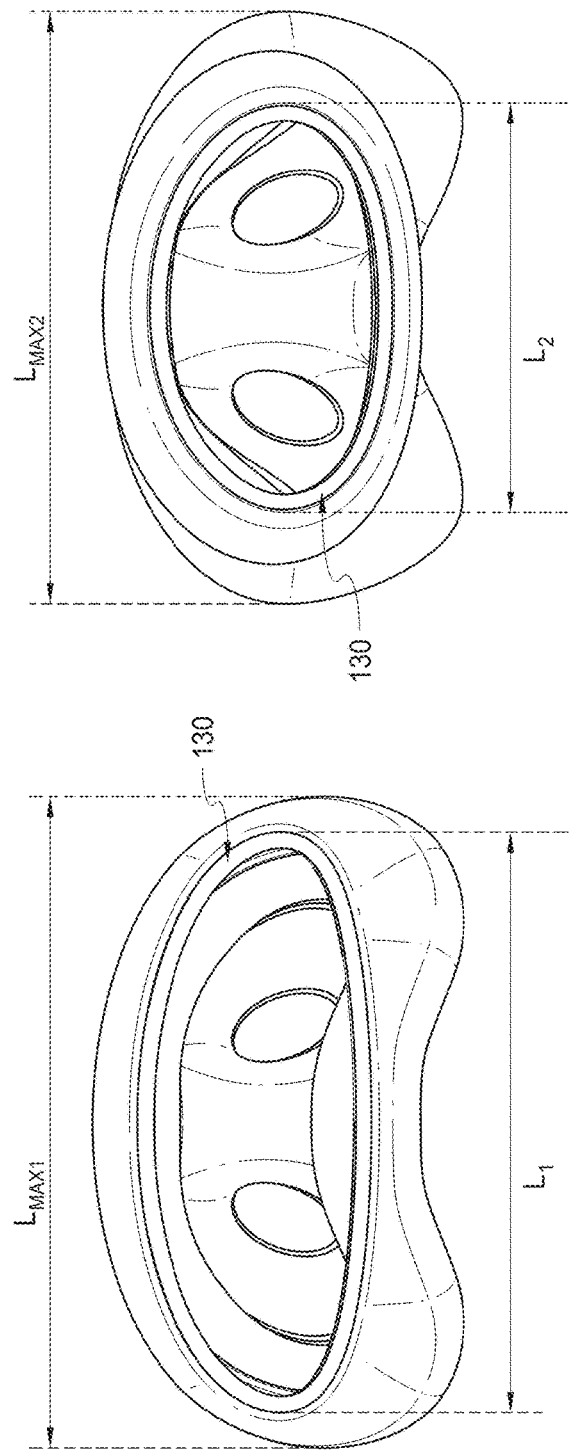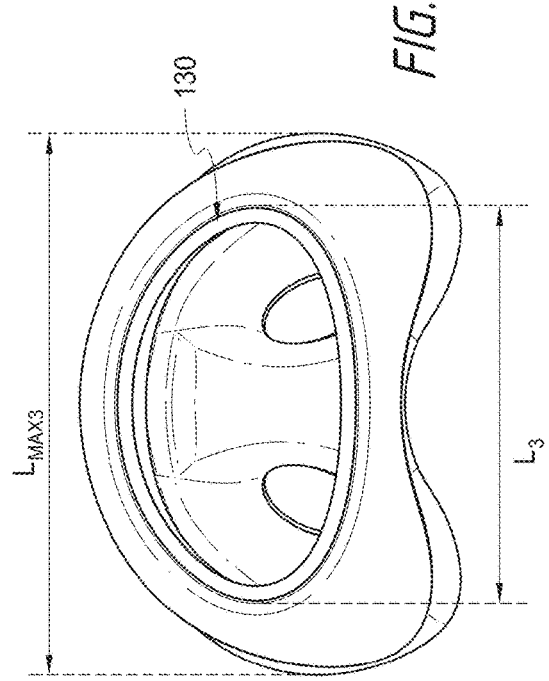

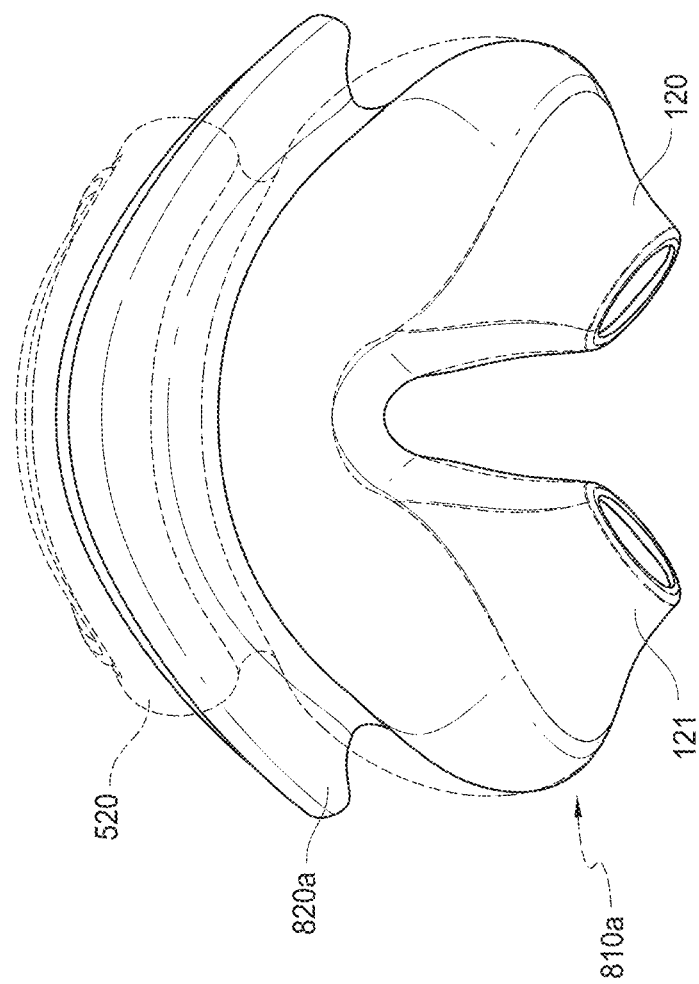

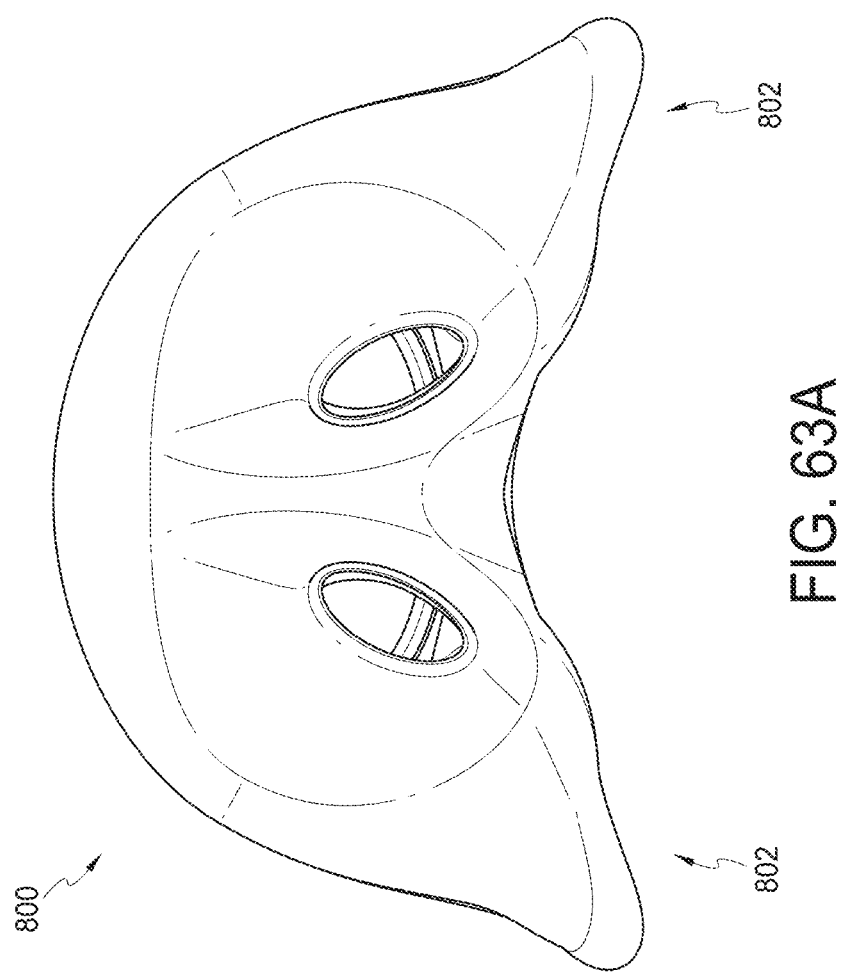

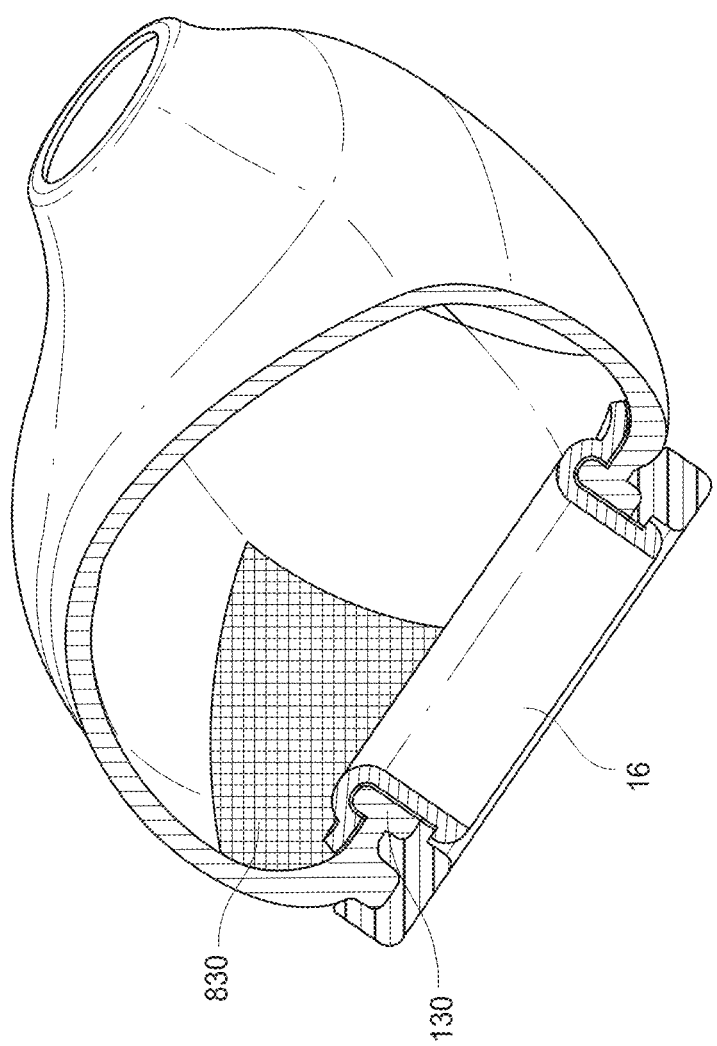

PATIENT INTERFACE AND ASPECTS THEREOF

INCORPORATION BY REFERENCE

This application is a continuation of U.S. application Ser. No. 16/094,723, filed Oct. 18, 2018, which is a U.S. National Phase application of PCT Application No. PCT/IB2017/052292, filed Apr. 21, 2017, which claims priority to U.S. Provisional Application No. 62/326,636, filed Apr. 22, 2016, the entirety of each of which is hereby incorporated by reference herein and made a part of the present disclosure.

BACKGROUND

Field

The disclosure generally relates to interfaces for providing a supply of breathable gas to a recipient.

Description of Related Art

Breathing gases can be delivered to users with a variety of different mask styles and can be delivered for a variety of different purposes. For example, users can be ventilated using non-invasive ventilation (NIV). In addition, continuous positive airway pressure (CPAP) or variable airway pressure can be delivered using masks to treat a medical disorder, such as obstructive sleep apnea (OSA), chronic obstructive pulmonary disease (COPD), or congestive heart failure (CHF).

These non-invasive ventilation and pressure support therapies generally involve the placement of a user interface device, which is typically a nasal or nasal/oral mask, on the face of a user. The flow of breathing gas can be delivered from the pressure/flow generating device to the airway of the user through the mask.

Typically, patient interface devices include a mask frame that supports a sealing member. The sealing member contacts the facial surfaces of the user, including regions surrounding the nose, including the nose and the nares. Because such masks are typically worn for an extended period of time, a variety of concerns must be taken into consideration. For example, in providing CPAP to treat OSA, the user normally wears the mask all night long while he or she sleeps. One concern in such a situation is that the mask should be as comfortable as possible. It is also important that the mask provide a sufficient seal against a user's face without significant discomfort.

SUMMARY OF THE INVENTIONS

Accordingly, it is an object of certain embodiments of the present disclosure to provide an improved sealing member for use in a mask assembly that overcomes the shortcomings of conventional sealing members or at least provides the public with a useful choice.

In some configurations, a nasal mask comprises a seal body formed of a soft flexible material and defining an inner cavity and one or more delivery openings for supply of breathing gases from the inner cavity to the patient. The seal body comprises a first nostril prong and a second nostril prong. Each of the first and second nostril prongs are non-conical and asymmetric.

In some configurations, a nasal mask comprises a seal body formed of a soft flexible material and defining an inner cavity and one or more delivery openings for supply of breathing gases from the inner cavity to the patient. The seal body comprises a breathing gas supply opening, for receiving breathing gas from a breathing gas source. A first nostril prong has a first distal end connected to the seal body and a first proximal end defining a first outlet opening configured to direct breathing gas into a first nostril of a patient. A first nares sealing surface connects the first distal end of the first nostril prong to the seal body. The first nares sealing surface has a first medial side and a first lateral side. A second nostril prong has a second distal end connected to the seal body and a second proximal end defining a second outlet opening configured to direct breathing gas into a second nostril of a patient. The first and second nostril prongs are spaced apart so as to accommodate a septum of a patient disposed between the first and second nostril prongs. A second nares sealing surface connects the second distal end of the second nostril prong to the seal body. The second nares sealing surface has a second medial side and a second lateral side. The first and second medial sides face towards each other and the first and second lateral sides face away from each other. Each of the first and second nares sealing surfaces are non-conical and asymmetric. Portions of the first and second medial sides extend substantially parallel to each other. Portions of each of the first and second lateral sides extend away from each other and at an angle of at least forty-five degrees relative to the first and second medial sides, respectively.

In some configurations, a nasal mask comprises a breathing gas conduit connector. A seal body is formed of a soft flexible material and defines an inner cavity and a first supply opening for supply of breathing gases from the inner cavity to the patient. The seal body comprises a first nostril prong, a second nostril prong and a rolling portion connecting disposed in a sidewall portion of the seal body. The rolling portion includes an upper portion configured to lie distal from an upper lip of a patient during use and a lower portion positioned to lie proximate to an upper lip of a patient during use. The upper portion is configured to provide less rolling resistance than the lower portion.

In some configurations, a nasal mask comprises a breathing gas conduit connector, a seal body formed of a soft flexible material and defining an inner cavity and one or more delivery openings for supply of breathing gases from the inner cavity to the patient. The seal body comprises a first nostril prong having a first distal end connected to the seal body and a first proximal end defining a first outlet opening configured to direct breathing gas into a first nostril of a patient. A first nares sealing surface connects the first distal end of the first nostril prong to the seal body. A second nostril prong has a second distal end connected to the seal body and a second proximal end defining a second outlet opening configured to direct breathing gas into a second nostril of a patient. A second nares sealing surface connects the second distal end of the second nostril prong to the seal body. A breathing gas supply opening is connected to the breathing gas conduit connector, for receiving breathing gas from a breathing gas source. A sidewall portion extends from the first and second nares sealing surfaces toward the breathing gas supply opening, along one or more first radii of curvatures. A rolling portion connects the sidewall portion to the breathing gas supply opening. The rolling portion extends along one or more second radii of curvatures that are less than the first radii of curvature. The rolling portion extends around the entire periphery of the breathing gas supply opening. The rolling portion includes an upper portion configured to lie distal from an upper lip of a patient during use and a lower portion positioned to lie proximate to an upper lip of a patient during use. The upper portion is configured to provide less rolling resistance than the lower portion.

In some configurations, a nasal mask comprises a breathing gas conduit connector, a seal body formed of a soft flexible material and defining an inner cavity and one or more delivery openings for supply of breathing gases from the inner cavity to the patient. The seal body comprises a first nostril prong, a second nostril prong, a breathing gas supply opening connected to the breathing gas conduit connector, for receiving breathing gas from a breathing gas source, and a sidewall portion extending in a first direction from the first and second nostril prongs toward the breathing gas supply opening along a proximal side of the seal body. The side wall portion comprises a concave portion extending along a lateral direction transverse to the first direction.

In some configurations, a nasal mask comprises a breathing gas conduit connector, a seal body formed of a soft flexible material and defining an inner cavity and one or more delivery openings for supply of breathing gases from the inner cavity to the patient. The seal body comprises a first nostril prong having a first distal end connected to the seal body and a first proximal end defining a first outlet opening configured to direct breathing gas into a first nostril of a patient. A first nares sealing surface connects the first distal end of the first nostril prong to the seal body. A second nostril prong has a second distal end connected to the seal body and a second proximal end defining a second outlet opening configured to direct breathing gas into a second nostril of a patient. A second nares sealing surface connects the second distal end of the second nostril prong to the seal body. A breathing gas supply opening is connected to the breathing gas conduit connector, for receiving breathing gas from a breathing gas source. A sidewall portion extends in a first direction from the first and second nares sealing surfaces toward the breathing gas supply opening along a proximal side of the seal body. The side wall portion comprises a concave portion extending along a lateral direction transverse to the first direction. The concavity has a curvature approximating a convex curvature of an upper lip of a patient.

In some configurations, a nasal mask comprises a breathing gas conduit connector, a seal body formed of a soft flexible material and defining an inner cavity and one or more delivery openings for supply of breathing gases from the inner cavity to the patient. The seal body comprises a first nostril prong including a first sealing surface and a second nostril prong including a second sealing surface. Portions of the first and second sealing surfaces are convex.

In some configurations, a nasal mask comprises a breathing gas conduit connector, a seal body formed of a soft flexible material and defining an inner cavity and one or more delivery openings for supply of breathing gases from the inner cavity to the patient. The seal body includes a first nostril prong having a first distal end connected to the seal body and a first proximal end defining a first outlet opening configured to direct breathing gas into a first nostril of a patient. A first nares sealing surface connects the first distal end of the first nostril prong to the seal body. The first nares sealing surface includes a first medial portion and a first lateral portion. A second nostril prong has a second distal end connected to the seal body and a second proximal end defining a second outlet opening configured to direct breathing gas into a second nostril of a patient. A second nares sealing surface connects the second distal end of the second nostril prong to the seal body. The second nares sealing surface includes a second medial portion and a second lateral portion. The first and second lateral portions of the first and second nares sealing surfaces are convex.

In some configurations, a nasal mask comprises a seal body formed of a soft flexible material and defining an inner cavity and a supply opening for supply of breathing gases from the inner cavity to the patient. The seal body comprises a first nostril prong, a second nostril prong, and a bellows portion disposed in a sidewall portion of the seal body. The bellows portion is located between the supply opening and the first and second nostril prongs. The bellows portion comprises an indentation that extends circumferentially around the seal body.

In some configurations, the indentation has a curved shape in cross-section.

In some configurations, the indentation extends around an entire circumference of the seal body.

In some configurations, the seal body comprises a base and a sealing portion, wherein the base comprises the supply opening and the bellows portion and wherein the sealing portion comprises the first nostril prong and the second nostril prong, wherein a volume of a portion of the inner cavity defined by the base is less than a volume the a portion of the inner cavity defined by the sealing portion.

In some configurations, the volume of the portion of the inner cavity defined by the base is less than a volume a portion of the inner cavity defined by either half of the sealing portion that contains the first nostril prong or the second nostril prong.

In some configurations, the sealing portion comprises a pair thickened regions, each associated with one of the first nostril prong and the second nostril prong.

In some configurations, a nasal mask comprises a seal body formed of a soft flexible material and defining an inner cavity and a supply opening for supply of breathing gases from the inner cavity to the patient. The seal body comprises a first nostril prong, a second nostril prong and a rolling section disposed in a sidewall portion of the seal body. The rolling section is located between the supply opening and the first and second nostril prongs. The rolling section is configured to roll over on itself to reduce a distance between the supply opening and the first and/or second nostril prongs.

In some configurations, the rolling section further comprises a rib that extends in a circumferential direction of the seal body.

In some configurations, the rib extends only partially around a circumference of the seal body.

In some configurations, the rib defines a gap in the front of the seal body.

In some configurations, a nasal mask comprises a seal body formed of a soft flexible material and defining an inner cavity and a supply opening for supply of breathing gases from the inner cavity to the patient. The seal body comprises a first portion that comprises the supply opening, a second portion that comprises a first nostril prong and a second nostril prong, and a bellows structure located between the first portion and the second portion. The bellows structure is configured to deform to vary a distance between the first portion and the second portion. A maximum width of the first portion is at least about 90 percent of a maximum width of the second portion.

In some configurations, the maximum width of the first portion is at least about 95% of the maximum width of the second portion.

In some configurations, the maximum width of the first portion is at least about 97.5% of the maximum width of the second portion.

In some configurations, the maximum width of the first portion is greater than the maximum width of the second portion.

In some configurations, the first nostril prong defines a first opening and the second nostril prong defines a second opening, wherein each of the first opening and the second opening comprises a major axis, wherein each of the first opening and the second opening are asymmetric about the major axis.

In some configurations, each of the first opening and the second opening comprise a minor axis, wherein an inner portion of the minor axis is smaller than an outer portion of the minor axis.

In some configurations, a ratio of the inner portion to the outer portion of the minor axis is about 6:7.

In some configurations, the supply opening is wider than the maximum width of the second portion.

In some configurations, a clip that is constructed from a material that is more rigid than a material of the seal body and is configured to connect the seal to a frame, wherein the clip is attached to the seal body and extends around the supply opening, wherein the seal body further comprises a rib that contacts the clip.

In some configurations, the rib extends outwardly away from the inner cavity.

In some configurations, the rib extends inwardly toward the inner cavity.

In some configurations, a clip that is constructed from a material that is more rigid than a material of the seal body and is configured to connect the seal to a frame, wherein the clip defines a male connection portion configured to engage a female connection portion of the frame.

In some configurations, the clip comprises a bias flow vent.

In some configurations, support features extend from each lower outer corner of the seal body and are configured to contact an upper lip of a user in use.

Various features, aspects and advantages of the present embodiments can be implemented in any of a variety of manners. For example, while several embodiments will be described herein, sets or subsets of features from any of the embodiments can be used with sets or subsets of features from any of the other embodiments.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the inventions. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

These and other features, aspects and advantages of the present inventions are described below with reference to the following drawings.

FIG. 55F is a top view of the medium sized version of the seal superimposed over a small sized version of the seal of FIG. 55A.
FIG. 55G is a front view of the seal of FIG. 55F.
FIG. 55I is a rear view of the seal of FIG. 55A.
FIG. 55J is a rear view of the seal of FIG. 61A.
FIG. 55K is a rear view of the seal of FIG. 62A.
FIG. 55O is a side cross-sectional view of the seal of FIG. 55A.
FIG. 56A is a top view of another example embodiment of a seal including a bellows.
FIG. 63A is a front view of an example embodiment of a seal including support features.
FIG. 64 is a side cross sectional view of an example embodiment of a seal including a seal clip.

DETAILED DESCRIPTION

Figure 1:
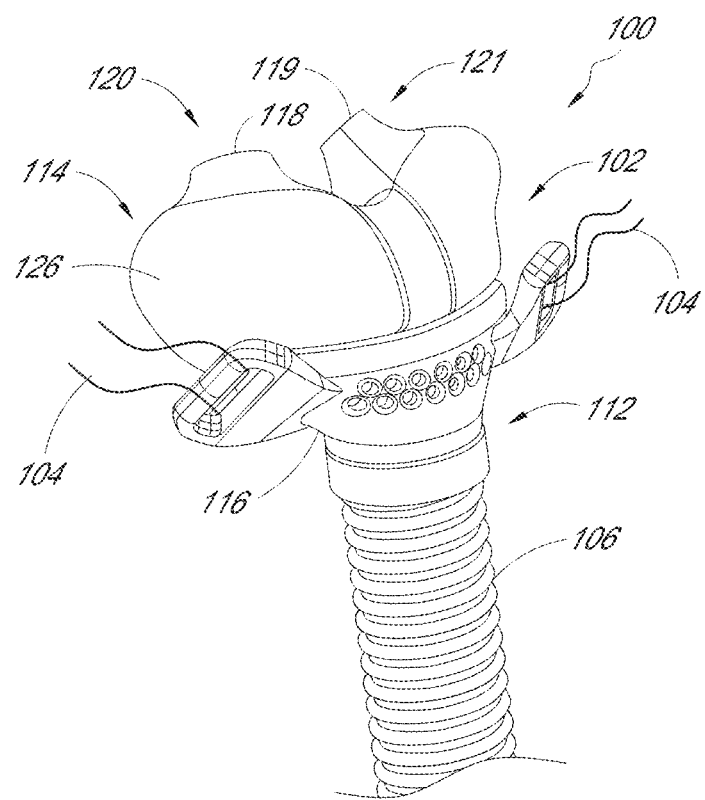
FIG. 1 is a front, top, and right side perspective view of a patient interface including a seal, a conduit connector, and a gas supply conduit, configured in accordance with an embodiment.
Figure 2:
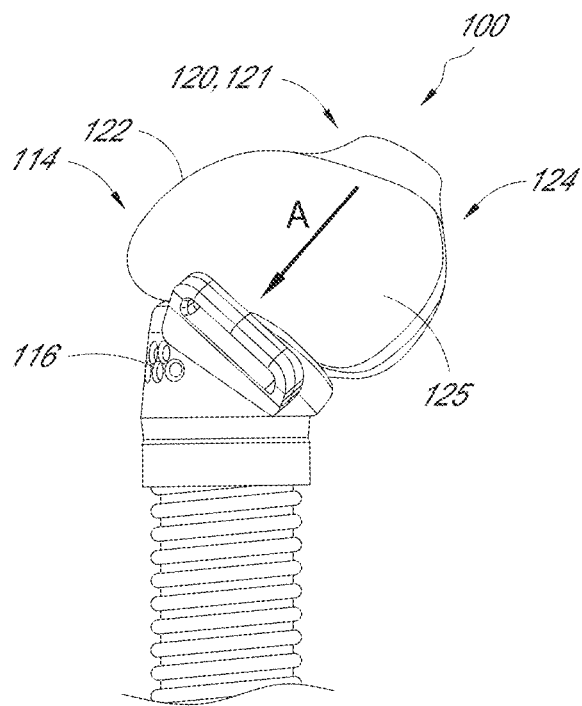
FIG. 2 is a side elevational view of the interface of FIG. 1.
Figure 3:
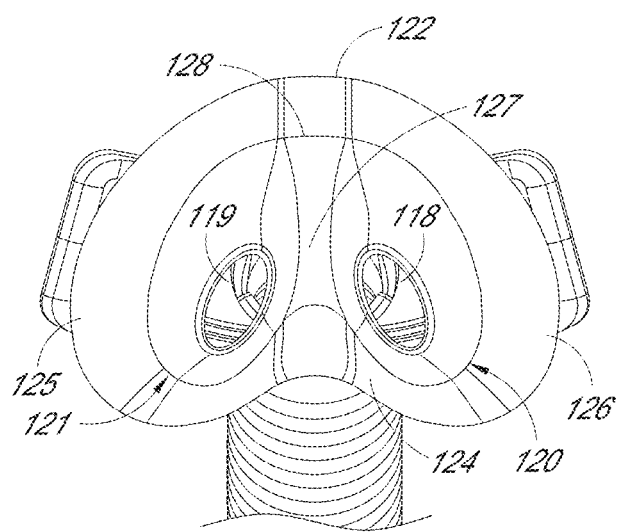
FIG. 3 is a view of the interface as viewed along arrow A of FIG. 2.
Figure 4:
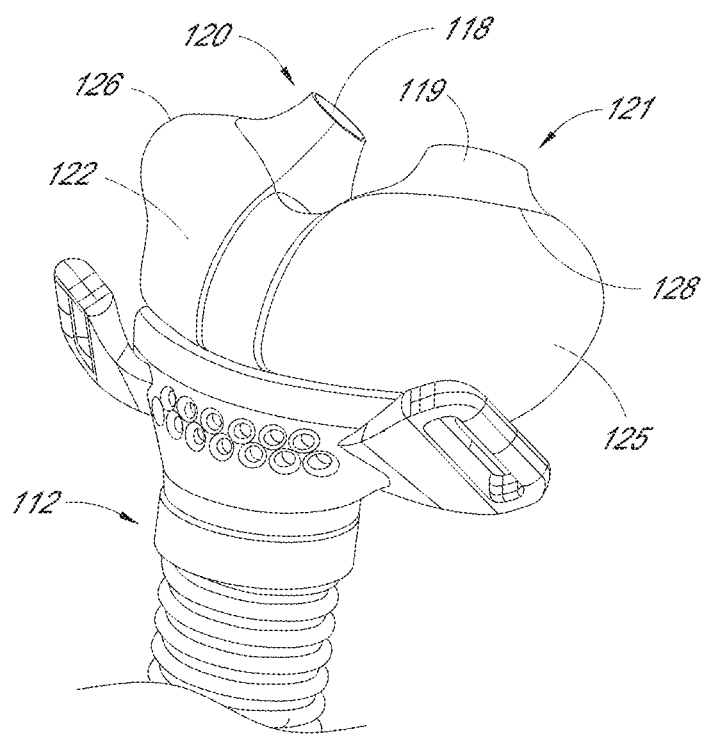
FIG. 4 is a front, left, and top perspective view of the interface of FIG. 1.

FIGS. 1-4 schematically illustrate a patient interface 100 that can include one or any combination of certain features, aspects, and advantages described herein. The interface 100 can be used to supply pressurized breathing gases to a recipient, such as a user or a patient. The interface 100 can be used for providing breathing gases to a recipient in situations where significant pressure changes may be encountered. For example but without limitation, the interface 100 can be used for delivering continuous positive airway pressure (CPAP).

With continued reference to FIGS. 1-4, the patient interface 100 is shown separated from a patient who might wear the interface 100. Some aspects of the patient interface 100, and variations on each aspect, have been described in U.S. patent application Ser. No. 12/945,141, filed Nov. 12, 2010, which is hereby incorporated by reference in its entirety. The interface 100 can be in the form of a mask 102. In some configurations, a strap 104 can be used to secure the mask to a patient. In some configurations, the interface can also comprise a flexible supply conduit 106 which can connect to the mask 102.

The mask 102 can be configured to fit over or overlie both nostrils of a patient. The strap 104 can be wrapped around the user's head in a simple loop above the user's ears, although other configurations and uses for the strap 104 are also available. In some configurations, the mask 102 can include lateral extending portions (not shown) configured to curve around toward each lateral side of a nose of a patient. Such lateral portions can form a perimeter seal on outwardly facing surfaces of flanks of the nose. On the other hand, the embodiments disclosed herein are described in the context of masks, which can be referred to as nasal pillow masks, which do not include laterally extending portions configured to curve around toward each lateral side of the nose of a patient to contact or form a perimeter seal on outwardly facing surfaces of flanks of the nose of a patient, such as the wings 130 disclosed in PCT Application No. PCT/NZ2014/000150 filed Jul. 17, 2014. Some of the embodiments disclosed herein can provide beneficial advantages of enhanced seals sealing performance and comfort while eliminating such laterally extending portions.

The flexible conduit 106 can depend from a central connection 112. In some configurations, the central connection 112 can be positioned at a frontal portion of the mask 102. The central connection 112 can include a swiveling elbow. Such a swiveling elbow can be configured to allow the flexible conduit 106 to pivot relative to the mask 102. By enabling pivoting, the elbow can help the interface 100 to better adapt to the sleeping positions of a patient. In some configurations, the central connection 112 may comprise a ball joint so that the elbow can pivot about axes parallel to and perpendicular to its connection with the mask 102. In some configurations, the central connection 112 may comprise a swivel or swivel elbow.

The illustrated mask 102 can generally comprise a seal 114 and a body or frame 116. The seal 114 and the frame 116 can be connected in any suitable manner.

The seal 114 can define a supple pocket or envelope that can contain a recess region. In some configurations, the seal 114 can comprise a low wall thickness and can be formed of any suitable material. For example but without limitation, the seal 114 can be formed of latex, vinyl, silicone or polyurethane. In some configurations the wall thickness can be below about 0.5 millimeters and could be lower than about 0.2 millimeters in some regions and in some configurations. Additionally, as described below, some portions of the seal 114 can include thickened regions having thicknesses of 0.7 millimeters, 0.9 millimeters, 1.2 millimeters, as well as greater thicknesses. In some configurations, the seal 114 can be formed of a material having sufficient elasticity and yield strength so that the combination renders the seal 114 supple. The seal 114 can be configured to withstand repeated drastic deformations without failure.

With continued reference to FIGS. 1-4, the seal 114 can include one or two nostril prongs 120, 121. The nostril locators 120, 121, can protrude from the seal 114. In some configurations, the nostril locators 120, 121 extend generally upwardly and rearwardly from a proximal wall 124 of the seal 114. As used herein, the term "proximal" is intended to refer to portions of the mask 102 that are proximate or closer to a patient during use. On the other hand, the term "distal" is used to refer to portions of the mask 102 which are disposed further away from a patient during use.

In the configurations illustrated in FIGS. 1-4, the nostril prongs 120, 121 are formed integrally (i.e., in a single monolithic piece) with the seal 114. Each nostril prong 120, 121 can comprise an outward aperture 118, 119 through which gas can be supplied from the flexible conduit 106, to nostrils of the patient. In some configurations, the gas can be supplied from within the pocket or envelope defined by the seal 114. In other configurations, the gas that is supplied can be separate from the gas supplied to the pocket or envelop defined by the seal 114.

The seal 114 can also be considered as having a distal wall 122. As such, an outer surface of the distal wall 122 would face away from the user during use, while an outer surface of the proximal wall 124 would face the user.

Figure 7:
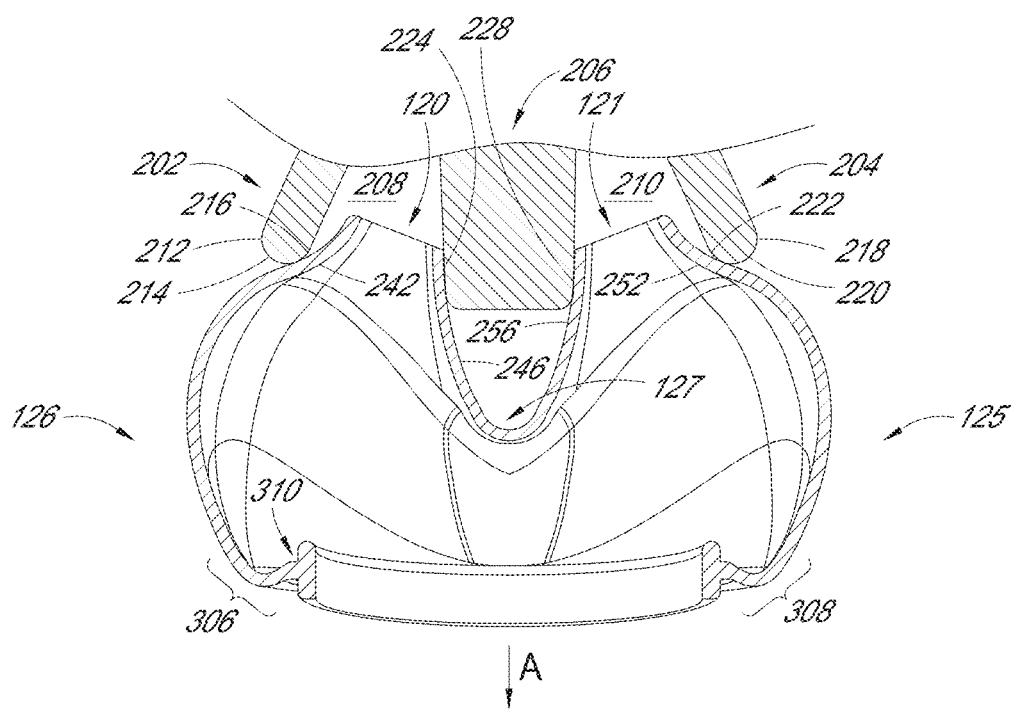
FIG. 7 is a sectional view of the seal of FIG. 5 engaged with human nostrils schematically illustrated in FIG. 6.

The seal 114 can also include left and right lateral walls 125, 126 disposed on the left and right sides, respectively, of the nostril prongs 120, 121. Additionally, the seal 114 can include an intermediate wall portion 127 extending between the nostril prongs 120, 121. The walls 122, 124, 125, 126 extend from the nostril prongs 120, 121 toward the flexible conduit 106, along the direction of arrow A in FIG. 2. Thus, proximal portions of the walls 122, 124, 125, 126 can be considered as connecting with the nostril prongs 120, 121. Distal ends of the walls 122, 124, 125, 126 can extend to an inlet orifice 130 (FIG. 7). The inlet orifice 130 can be connected to the frame 116 and/or directly to the flexible conduit 106. In some embodiments, a seal clip 16 can be coupled to the inlet orifice 130, for example as shown in FIG. 64, to help provide support to the seal and increase the ability of the seal to handle and accommodate shear forces.

As such, the envelope or pocket described above can be defined within at least the distal wall 122 and the proximal wall 124 and/or optionally, the lateral walls 125, 126, or a combination thereof. The seal 114 can be configured to achieve a desired seal without wrapping around the tip or lower portion (e.g., locations below the bridge) onto substantial portions of the outer surfaces a user's nose. However, in some embodiments, the seal 114 can be designed to wrap around the tip or lower portion of a user's nose. The seal 114 can also be considered as including a central portion 128 which can be considered as including the nostril prongs 120, 121, and the central wall 127. The central portion 128 can, in some embodiments, include sealing surfaces of the mask 102 which form seals with the nostrils of a user during use. The central wall 127 can be disposed significantly deeper and further distally from the orifices 118, 119 than the other portions, such as the sealing surface within the central portion 128. As such, the central wall 127 provides improved clearance for the user's septum, reducing contact and potential discomfort or irritation.

As described above, optionally, a substantial portion of the seal 114 can be supple. For example, a region surrounding the nostril locators, such as the central region 128, can be more supple than distal portions of the walls 122, 124, 125, 126. Further, optionally, the proximal wall 124 and the nostril prongs 120, 121 can be very supple so that they can expand to conform to the contours of a user's nares. The supple portions of the seal 114 can be of sufficient dimension and shape that when positive pressure of gases within the seal 114 can partially expand portions of the seal 114 to enhance a seal between the seal 114 and the user's face, for example, nostrils of the user. Additionally, portions of the seal, for example, along proximal portions of the proximal wall 124 can rest against or provide the sealing engagement with a portion of the user's upper lip.

Optionally, portions of the seal 114 can have an increased rigidity to improve form, fit, and function of the mask 102. For example, portions of the seal 114 can be made significantly stiffer to provide control of ballooning of other regions of the seal 114. Further, distal portions of the walls 122, 124, 125, 126, for example, regions or areas adjacent to or proximate to the inlet orifice 130 (FIG. 7) can be less supple. Thus, for example, one or more the walls 122, 124, 125, 126 can have a decreasing suppleness from the proximal portions thereof to the distal portions thereof. Such less supple regions can be formed of a different material or can be formed of the same material but with an increased thickness.

The frame 116 can have any arrangement for fixation or connection to the seal 114. In some configurations, an annular wall can extend from a proximal side of the frame 116 around a perimeter of an opening extending to the connector 112. The annular wall can include an outwardly extending lip. The inlet orifice 130 of the seal 114 can engage over the outwardly extending lip of the annular wall. In some configurations, the inlet orifice 130 of the seal 114 can be stretched to fit over the annular wall. The inlet orifice 130 of the seal 114 can be provided with a thickened or reinforced wall section, for example but with limitation. In some configurations, an extended portion of the inlet orifice 130 can be rolled up over the annular wall of the frame 116. In other configurations, the seal 114 can be provided with a portion of a connector on at least one of the frame 116 and the conduit 106 can include a complimentary connector portion.

The frame 116 can be configured to be minimal in size. For example, a small sized frame 116 can enable a clear field of vision for the user and can allow a user to wear glasses while wearing the interface 100. The frame 116 can be formed of an elastomeric material, which can allow the frame 116 to flex to conform slightly to the face of the user. The frame 116, however, can provide some support for the seal 114. By providing support for the seal 114, the seal 114 can be more effectively pressed into contact with the face and nose of the user. The frame 116 can be formed by injection molding, preferably from an elastic material, such as silicone or polyurethane, for example but without limitation. In some configurations, the frame 116 can be formed of more rigid materials, such as polycarbonate, polyester polystyrene, or nylon, for example but without limitation.

In use, portions of the seal 114 can be inflated and thus expanded outwardly. Pressure within the seal 114 (e.g., inflated from the flow of pressurized gases supplied to the patient interface 100) can press the sealing surfaces of the seal 114 against the skin of a user and to further conform to contours of the outside surfaces of the nose of the user, to surfaces of the lower portion of the nose of the user, to various portions of the nares of the user, as well as surfaces of the upper lip of the user immediately below the nose.

Figure 6:
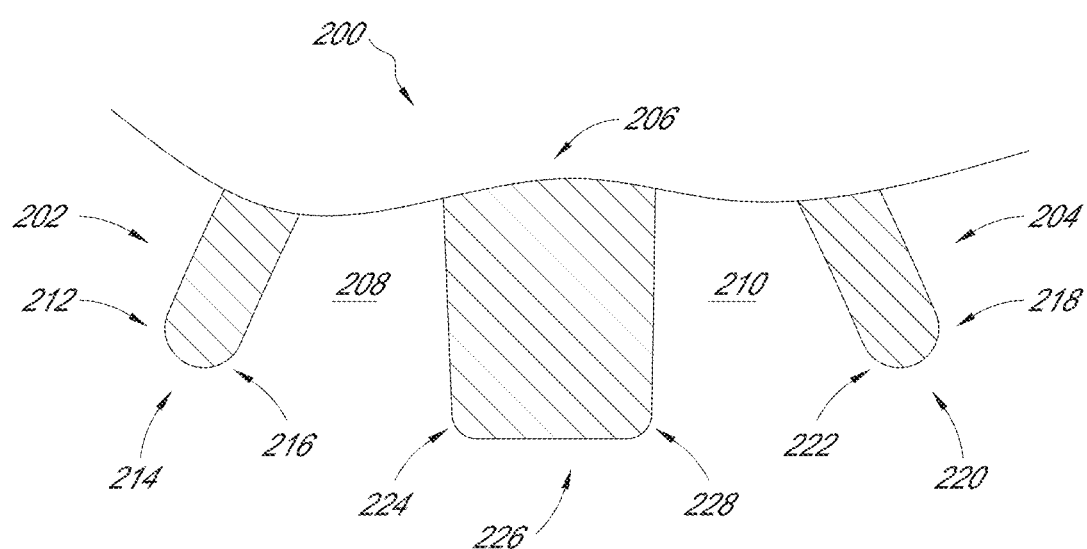
FIG. 6 is an enlarged schematic and partial sectional view of nostrils of a human patient.

With reference to FIG. 6, the lower portion of a human nose 200 (illustrated in front elevation and partial cross section) can be considered as including the walls and surfaces and portions described below, the names of which are included herein for facilitating understanding of the present disclosure.

With continued reference to FIG. 6, the lower end of a human nose 200 can include a right nostril lateral wall 202, a left nostril lateral wall 204, and a septum 206. The right nostril lateral wall 202 extends from a forward facing surface of the patient's face, to the tip of the nose. Similarly, the left nostril lateral wall 204 extends from a left side of the user's face toward the tip of the nose. The septum 206 extends from the user's face to the tip of the nose, and between the left and right nostril lateral walls 202, 204. As such, the right nostril lateral wall 202 and the septum 206 define the right nostril 208 of the user. Similarly, the left nostril lateral wall 204 and the septum 206 define the right nostril 210 of the user.

The lower ends of the lateral walls 202, 204 and the septum 206 can be also considered as forming the nares of the user, including outer, inner and lower surfaces thereof.

For example, the lower portion of the right nostril lateral wall 202 can be considered as having lateral outer surface 212, bottom surface 214, and intermedial surface 216. Similarly, the lower portion of the left nostril lateral wall 204 can be considered as including outer lateral surface 218, bottom surface 220, and intermedial surface 222.

The septum 206 can be considered as including right lateral surface 224, bottom surface 226 and left lateral surface 228.

Figure 5:
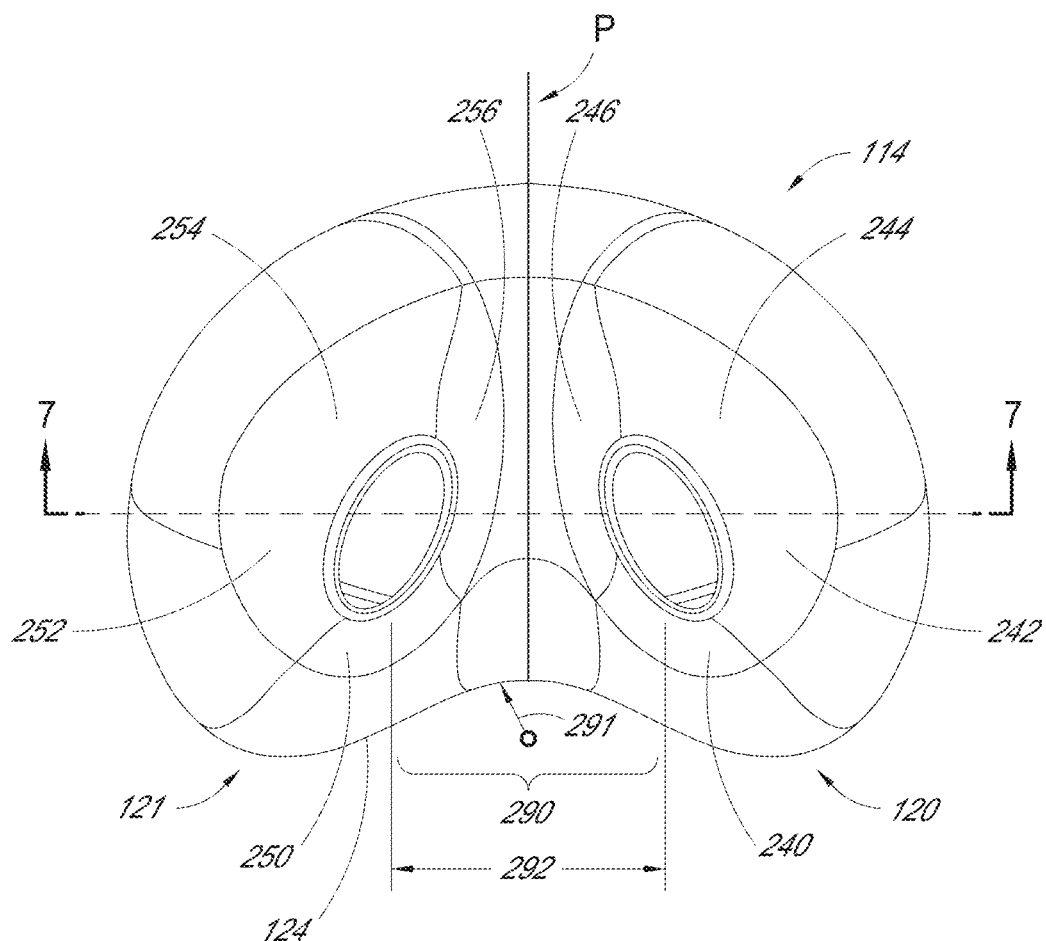
FIG. 5 is an embodiment of a seal body that can be used with the interface of FIGS. 1-4, viewed in a direction such as that on by arrow A in FIG. 2.

With reference to FIG. 5, the right and left nostril prongs 120, 121 can also be considered as including lateral, medial, proximal, and distal portions. For example, the right nostril prong 120 can be considered as including a proximal portion 240, a lateral portion 242, a distal portion 244 and a medial portion 246. Similarly, the left nostril prong 121 can be considered as including a proximal portion 250, a lateral portion 252, a distal portion 254 and a medial portion 256.

With continued reference to FIG. 7, as noted above, the seal 114 can be configured to be sufficiently supple that it can be inflated and thus expanded by positive pressure within the seal 114. Thus, for example, as illustrated in FIG. 7, such pressure can beneficially push the lateral portions 242, 252 of the right and left nostril prongs 120, 121 into enhanced contact with the medial surfaces 216, 222, and optionally further contact with the bottom surfaces 214, 220, and further optionally, the lateral surfaces 212, 218, optionally without making contact with substantial portions of the lateral surfaces 212, 218. Similarly, the medial portions 246, 256 can be pushed inwardly by the positive pressure, thereby increasing contact and sealing effect against the lateral walls 224, 228.

Figure 7A:
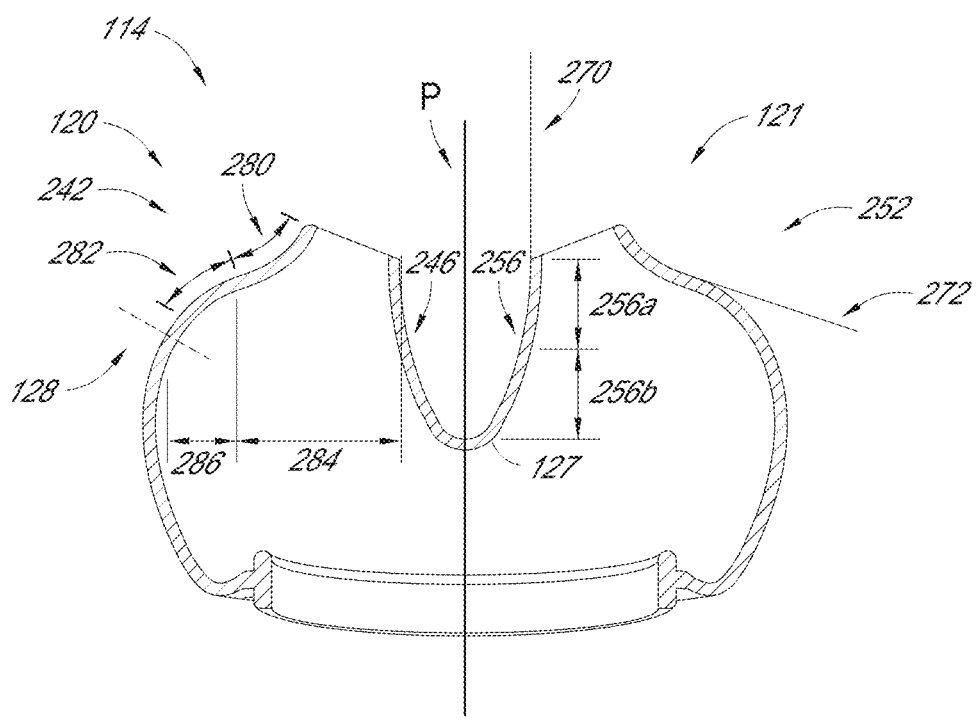
FIG. 7a is a sectional view of the embodiment of FIG. 7, with certain lines removed.

With continued reference to FIGS. 7 and 7a, as described above, the nostril prongs 120, 121 can be configured to seal against the septum 206 and the lateral nostril walls 202, 204, differently. For example, as described above, the medial portions 246, 256 of the nostril prongs 120, 121 can be configured, oriented, and/or shaped to press more against the lateral surfaces 220a, 224 of the septum 206 and reduce or minimize contact with bottom surface 226 of the septum 206. Optionally, the central wall 127, as noted above, can be spaced deeply between the nostril prongs 120, 121, so as to reduced or eliminate the likelihood of contact with any or a substantial portion of the bottom surface 226 of the septum 206. The degree to which the medial portions 246, 256 press against the lateral surfaces 224, 228 and less on the bottom surface 226 can be contrasted with the configuration, shape, and orientation of the laterals portions 242 and 252.

Optionally, the lateral portions 242, 252 can be shaped, configured and/or oriented so as to contact less of the medial portions 216, 222 of the right and left nostril walls 202, 204 and more of the bottom surfaces 214, 220 and the lateral surfaces 212, 218, during use, as compared with the contact of the medial portions 246, 256 with the corresponding portions of the septum 206, described above.

Asymmetric Prongs

With reference to FIGS. 7 and 7a, optionally, in some embodiments, the nostril prongs 120, 121 can be configured to provide a differential sealing contact with a user's nose 200, with an asymmetric prong shape. Certain aspects of the asymmetry of the prongs 120, 121 can be described with reference to a central plane P bisecting the seal 114 in a direction directly between the prongs 120, 121. For example, as shown in FIG. 7a, the medial portion 256 of the nostril prong 121 extends in a direction that is nearly vertical or in other words, parallel, nearly parallel, substantially parallel, or within approximately 10 degrees of the central plane P. In some embodiments, the medial portion 256 of nostril prong 121 extends at an angle, with respect to central plane P, of approximately 10 degrees, 0-15 degrees, 0-5 degrees, 5-10 degrees, 10-15 degrees, 5-15 degrees, greater than 0 degrees, or various sub-ranges of 0-15 degrees. The slope of the medial portion 256 is represented by line 270. With regard to this description of the seal 114, and other descriptions set forth below, in some instances, features are only described in connection with one of the prongs 120, 121, but it is to be understood that both of the prongs 120, 121 can have the same shape, and thus the descriptions would apply equally to both prongs 120, 121. With continued reference to FIG. 7a, in some embodiments, the medial portion 256 comprises an upper portion 256a and a lower portion 256b. The upper portion 256a can be angled, with respect to plane P, at approximately 10 degrees, 0-15 degrees, 0-5 degrees, 5-10 degrees, 10-15 degrees, 5-15 degrees, greater than 0 degrees, or various sub-ranges of 0-15 degrees. The lower portion 256b of the medial portion 256 can be angled, with respect to plane P, at approximately 20 degrees, 0-30 degrees, 0-20 degrees, 10-30 degrees, 15-25 degrees. In some embodiments, the upper portion 256a of the medial portion 256 comprises up to one half of the medial portion 256.

In contrast to the slope of the medial portion 256, the slope of the lateral portion 252 is not nearly parallel, approximately parallel or substantially parallel with the central plane P. Rather, the slope of the lateral portion 252 is transverse to the plane P and optionally can be nearly perpendicular to the plane P. In FIG. 7a, the slope of the lateral portion 252 is identified by the line 272. The line 272 extends at an angle of about 75 degrees relative to the plane P. In some embodiments, the slope 272 can be within the range of approximately 60-90 degrees relative to the plane P. In some embodiments, the angle is approximately 70 degrees, 60-70 degrees, 70-80 degrees, 80-90 degrees, 60-75 degrees, 75-90 degrees, less than 90 degrees, or various sub-ranges of 60-90 degrees.

With continue reference to FIGS. 5 and 7a, the difference in shape between the medial portions 246, 256 and the lateral portions 242, 252 also extends, optionally, partly into the distal and proximal portions 244, 254, 240, 250. Additionally, the distal and proximal portions 244, 254 can extend through contours so as to smoothly transition between the different shapes of the medial portions 246, 256 and the lateral portions 242, 252. For example, portions of the proximal and distal portions 250, 254 adjacent to the lateral portion 252 can have a similar shape, while portions of the proximal and distal portions 250, 254 adjacent to the medial portion 256 can have a shape similar to the medial portion 256, so as to provide a smooth transition around the periphery of the prongs 120, 121.

Convex Sealing Surface

Optionally, the seal 114 can include further features for sealing differently against the left and right lateral walls 202, 204 compared to sealing against the septum 206. For example, with reference to FIG. 7a, as noted above, the medial portions 246, 256 of the prongs 120, 121 extend generally vertical or parallel with the central plane P. In contrast, the lateral portions 242, 252 can include a convex sealing surface positioned for contact with the lower portion of the patient's lateral nostril walls 202, 204.

As shown in FIG. 7a, a proximal end of the lateral portion 242 includes a concave portion 280. Distal from the portion 280 is a convex portion 282. The concave and convex portions 280, 282 fall within the central area 128 which can be considered as comprising the sealing surfaces of the seal 114, described above with reference to FIG. 3.

In some embodiments, the concave portion 280 can be smaller than the convex portion 282. Thus, the concave portion may only act as a sealing surface on patients with particularly small nares. The convex portion 282 can be larger to accommodate a larger range of different size nares, and preferentially sealing against such nares with the convex portion 282 which is convex in a relaxed state, but may be deformed into a concave state upon application against a patient's nose 280. In this respect, in at least some patients, the concave portion 280 may be a locating or alignment feature and the convex portion 282 is a sealing surface. Extending in a substantially horizontal angle can help limit the depth to which the nostril prongs 120, 121 extend into the patient's nostrils 208, 210. Inserting prongs too deeply into a patient's nose can cause contact with sensitive internal surfaces of the nares and cause irritation and discomfort for the patient. Thus, the depth of the prongs 120, 121 and the extent to which prongs 120, 121 would extend into a nose can be balanced with the need for stability provided by the prongs 120, 121, which is enhanced when the prongs 120, 121 sit far enough within the nostrils that they aren't too easily displaced when the mask 102 moves on the patient's face. In a non-limiting example, the distance between the medial surface 246 and the lateral end of the concave portion 280 is approximately 12.7 millimeters, and the width of the convex portion 282 can be approximately 6.8 millimeters, as measured in the directions identified in FIG. 7a.

As noted above, the prongs 120, 121 and have a concave sealing area which can be configured to provide reduced contact area with nares a user, so as to reduce irritation of the nares. Measurements of human noses have revealed that among at least some groups of human populations, the width x of a human septum 226, is fairly constant, i.e., varies little. On the other hand, such measurements have revealed that the length y of human nares, as well as the outermost width of human nares, vary relatively more. Thus, the shape of the openings and the prongs 120, 121 themselves, are generally non-conical and asymmetric so as to better accommodate these variations. For example, as noted above, because the with x of the human septum 226 varies little, the shape of the prongs 120, 121, in those areas which would contact a septum 226, such as the medial walls 256, 246, can be fairly vertical so as to reduce the likelihood of irritation caused on the nares, such as the lateral wall portions 224, 228, and the lower wall of the septum 226.

Figure 7B:
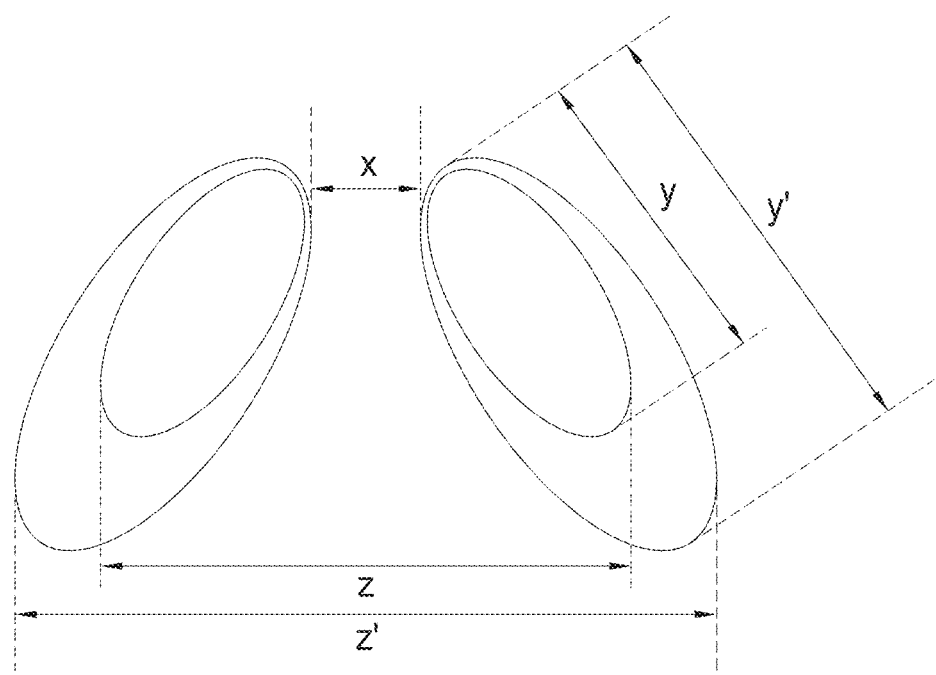
FIG. 7b is a schematic diagram illustrating variations in dimensions of nares amongst some human populations.
Figure 7C:
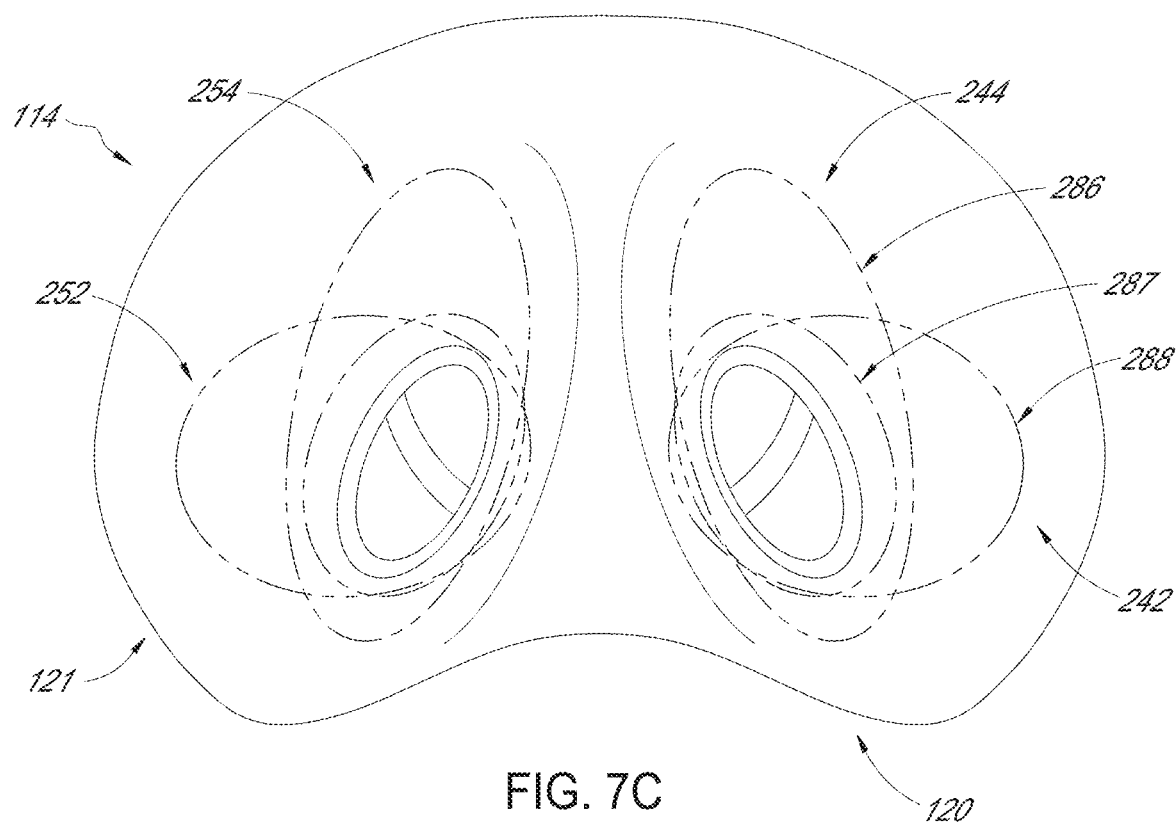
FIG. 7c is a view of the seal of FIG. 5, which schematic indications of examples of optional locations of sealing between the seal and the nares of differently-shaped human noses.
Figure 7D:
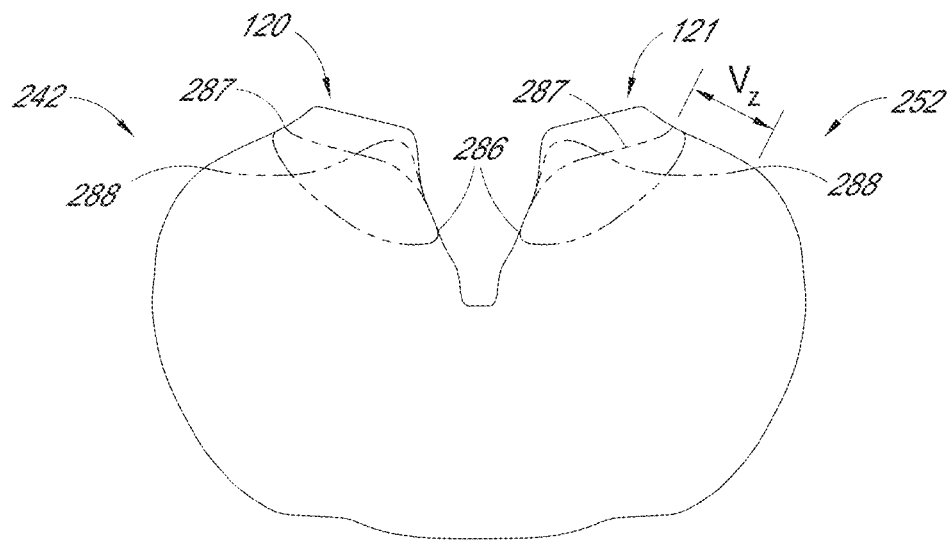
FIG. 7d is a top plan view of the seal with the schematic indications of FIG. 7c.

For example, with reference to FIG. 7c, longer and narrower nostrils can tend to seal around the prong 120 along sealing line 286, smaller nostrils can tend to seal around the prong 120 along sealing line 287, and wider nostrils can tend to seal around the prong 120 along sealing line 288. With regard to FIG. 7d, comparison of the lines 286, 287, 288, shows a distal-proximal variation Vz (generally corresponding to the "z" dimension identified above with reference to FIG. 7b) in the lateral locations of the lines 286, 287, 288, on the lateral portions 242, 252, of the prongs 120, 121.

Figure 7E:
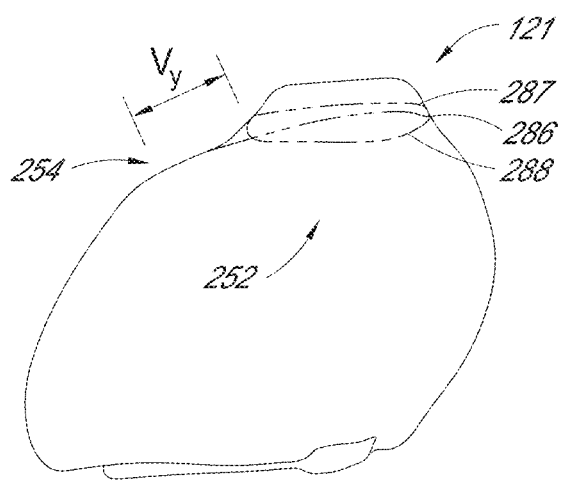
FIG. 7e is a left side elevational view of the seal with the schematic indications of FIG. 7c.

Similarly, with reference to FIG. 7e, comparison of the lines 286, 287, 288 shows a medial-lateral variation VY (generally corresponding to the "y" dimension identified above with reference to FIG. 7b) of the locations of the feeling lines 286, 287, 288, on the distal portions 244, 254, of the prongs 120, 121.

Figure 7F:
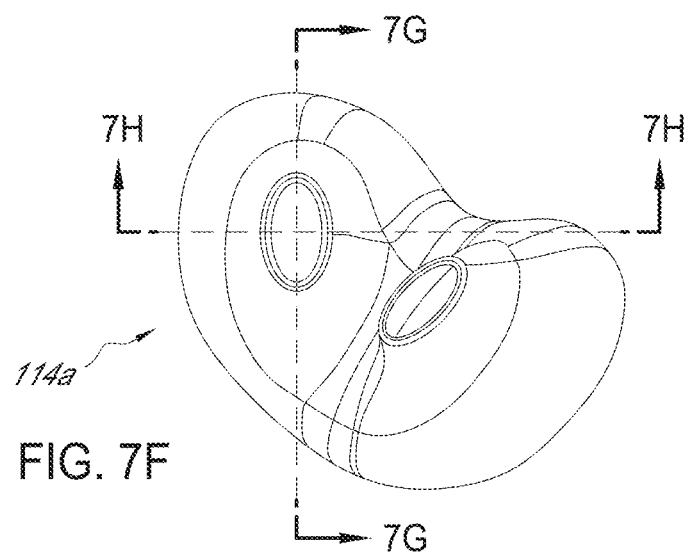
FIG. 7f is a top, front, and left side perspective view of a modification of the seal of FIG. 5.
Figure 7G:
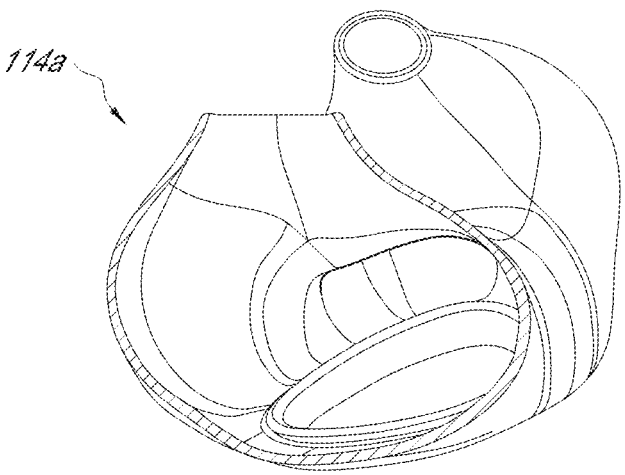
FIG. 7g is a sectional view of the seal of FIG. 7f, taken along section line 7g-7g.
Figure 7H:
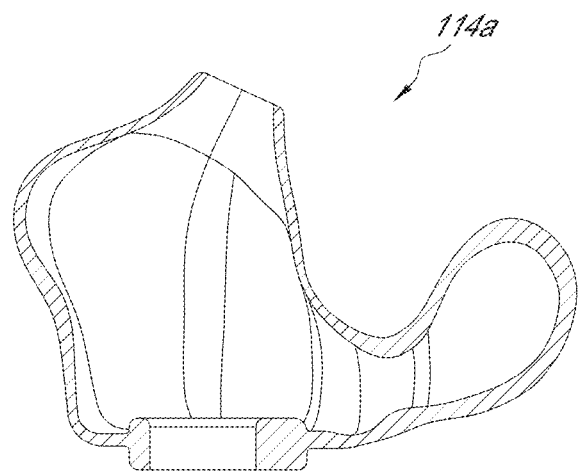
FIG. 7h is a sectional view of the seal of FIG. 7f, taken along section line 7h-7h.
Figure 8:
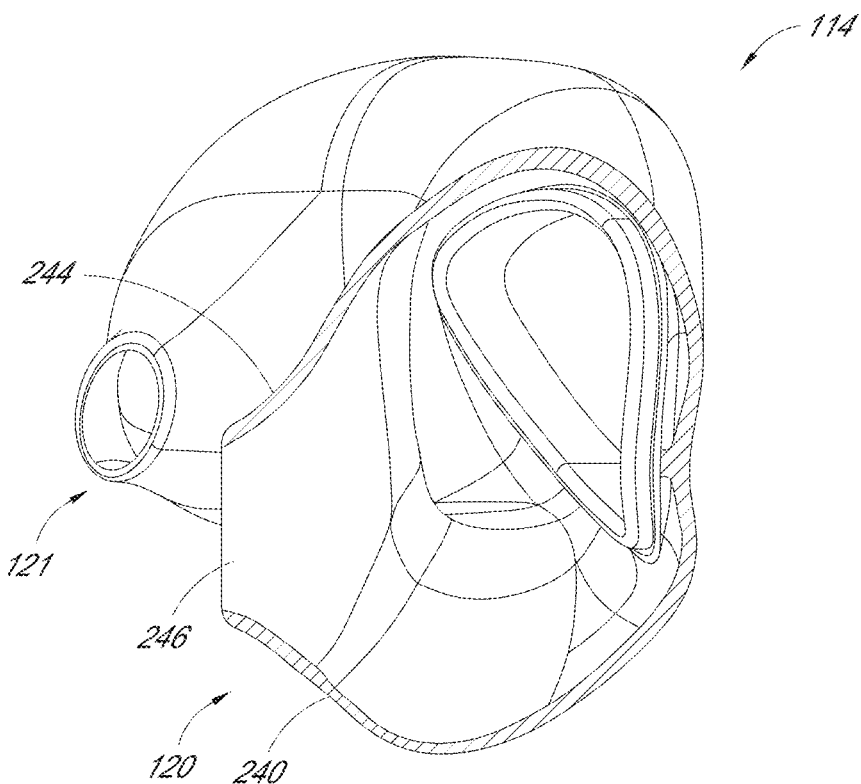
FIG. 8 is a perspective and partial sectional view of the seal of FIG. 5.

FIGS. 7f-7h illustrate a modification of the seal 114, identified generally by the reference numeral 114a that can also include the features described above with reference to seal 114 as well as the features described below with reference to seal 1114.

Semi-Inflating Seal

As noted above, the sealing surfaces extending around the nostril prongs 120, 121 can be made sufficiently flexible and supple so as to inflate to a degree when subject to positive air pressure within the seal 114. Such inflation allows for more positive engagement between the sealing surfaces and the lower surfaces of the patient's nose. More specifically, the proximal, lateral, distal, and medial portions 240, 242, 244, 246 of the nostril prong 120, which comprise the sealing surfaces within the area 128, can be made sufficiently thin and/or supple so as to partially inflate and deflect under positive pressure generated within the seal 114. As such, these portions 240, 242, 244, 246 can deflect to a degree, i.e., outwardly, so as to provide better positive sealing and engagement with the medial surface 228 of the septum 206 and the medial, bottom, and lateral surfaces 222, 220, 218 of the patient's lateral nostril wall 204.

Lip Engagement

Optionally, the seal 114 can also include enhanced comfort and/or engagement with an upper lip of a patient. For example, with reference to FIG. 5, the proximal wall 124 can include a concave portion 290 extending in a lateral direction, transverse to the central plane P. This concave portion 290 can have a shape that generally conforms to a typical shape of a human's upper lip, and particularly the portion of the upper lip proximal to the lower end of the user's nose. Typically, the upper lip of a human extends in a lateral direction and has a generally convex shape. Thus, the concave portion 290 is configured to fit a typical human upper lip configuration. In some embodiments, the concave portion 290 extends over a distance 292 which is approximately equal to a distance between the centers of the nostril prongs 120, 121. However, other lengths of the concave portion can also be used.

In some embodiments, the concave portion 290 includes a radius of curvature 291 of approximately 12.5 mm, 10-15 mm, 12-13 mm, or various sub-ranges thereof. However, other configurations can also be used. Optionally, the thickness of the proximal wall 124, in the area of the concave portion 290 can be reduced so that it conforms more readily to the lip geometry of individual users. In a non-limiting exemplary embodiment, the thickness of the proximal wall 124 is approximately 0.7 mm.

Rolling Section

Optionally, the seal 114 can include a configuration for a preferential rolling deformation in the vicinity of the connection between the side walls of the seal 114 and the inlet orifice 130. For example, as described above with reference to FIG. 2, the proximal, lateral, and distal walls 124, 125, 126, 122, extend from the nostril prongs 120, 121 to the inlet orifice 130. The distal ends of the walls 124, 125, 126, 122, include rolling portions formed in the vicinity of the inlet orifice 130, for example, including the last few millimeters of the walls. For example, the walls can extend toward the inlet orifice 130 along the direction A (FIGS. 2 and 7), overshoot the connection point to the inlet orifice 130, and curl back, in a direction opposite to the direction of arrow A. This overshoot and curl configuration generates an area in these walls which tends to deform first when forces are applied, causing a rolling deformation effect.

Figure 11:
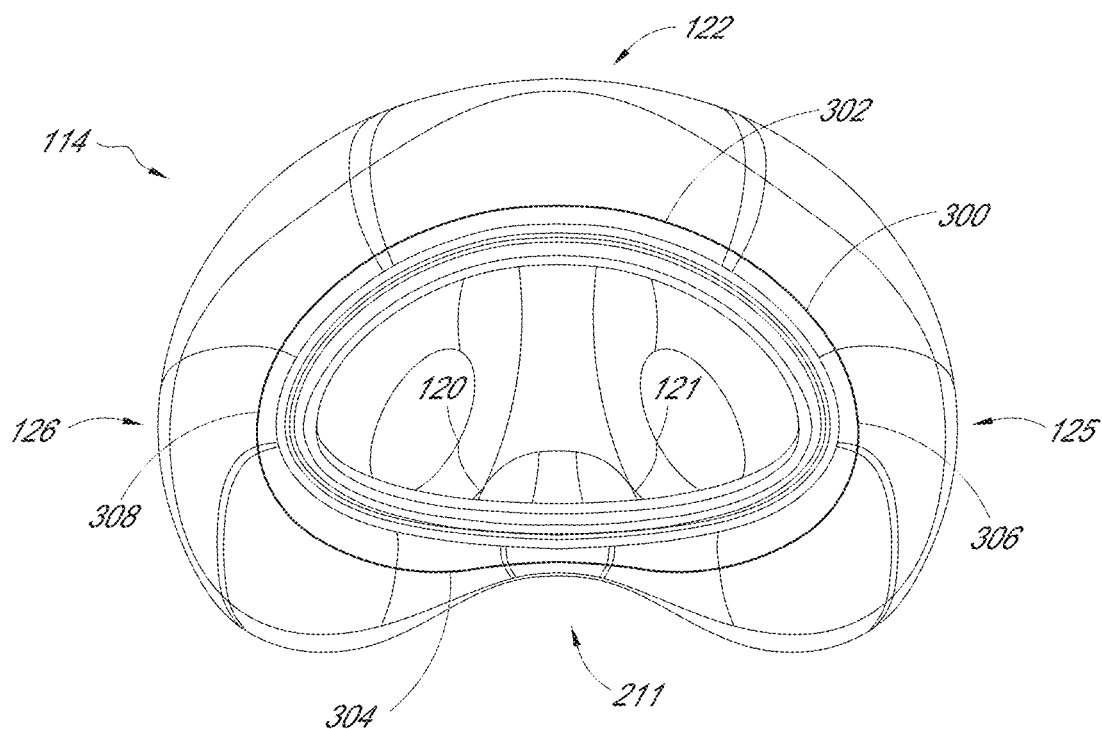
FIG. 11 is a front elevational view of the seal of FIG. 5.

With reference to FIG. 11, the rolling portions at the distal ends of the walls 122, 124, 125, 126 can be considered as being within the area 300. Thus, the walls 122, 124, 125, 126 can have associated rolling portions 302, 304, 306, 308, within the rolling area 300, as illustrated in FIG. 11. The cross-section of FIG. 7 illustrates a configuration of the portions 306, 308.

As shown in FIG. 7, the wall 126 extends distally from the nostril prong 120 to the rolling portion 306. The rolling portion 306 extends beyond the connection point 310; i.e., lower than the connection point 310 as viewed in FIG. 7, then extends upwardly in a direction opposite to the direction of arrow A, to the connection point 310. This overshot and curled back configuration of the rolling portion 306 can provide for enhanced and preferential deformation and rolling of the rolling area 300.

Figure 9:
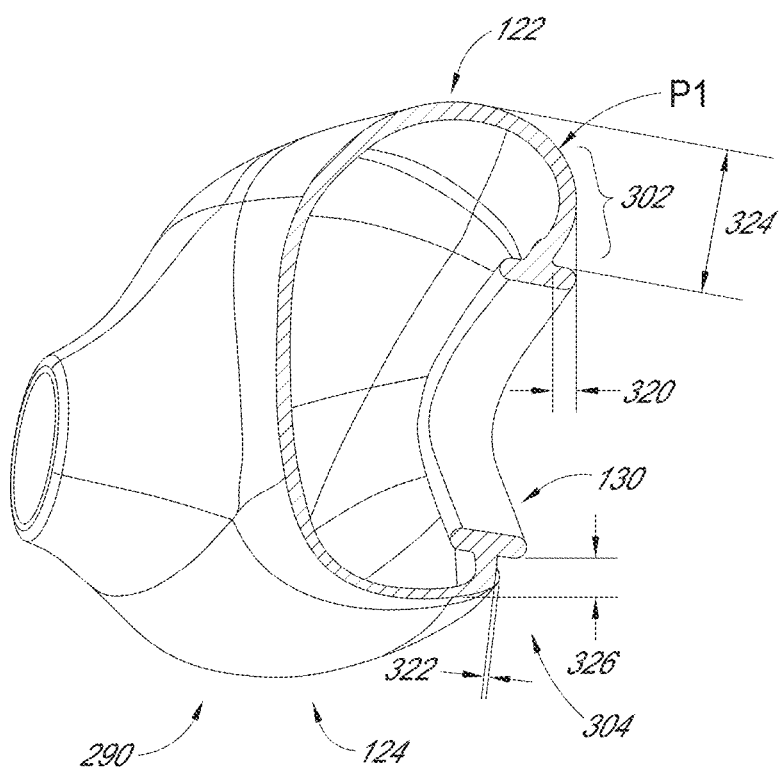
FIG. 9 is another partial sectional and perspective view of the seal of FIG. 5.
Figure 10:
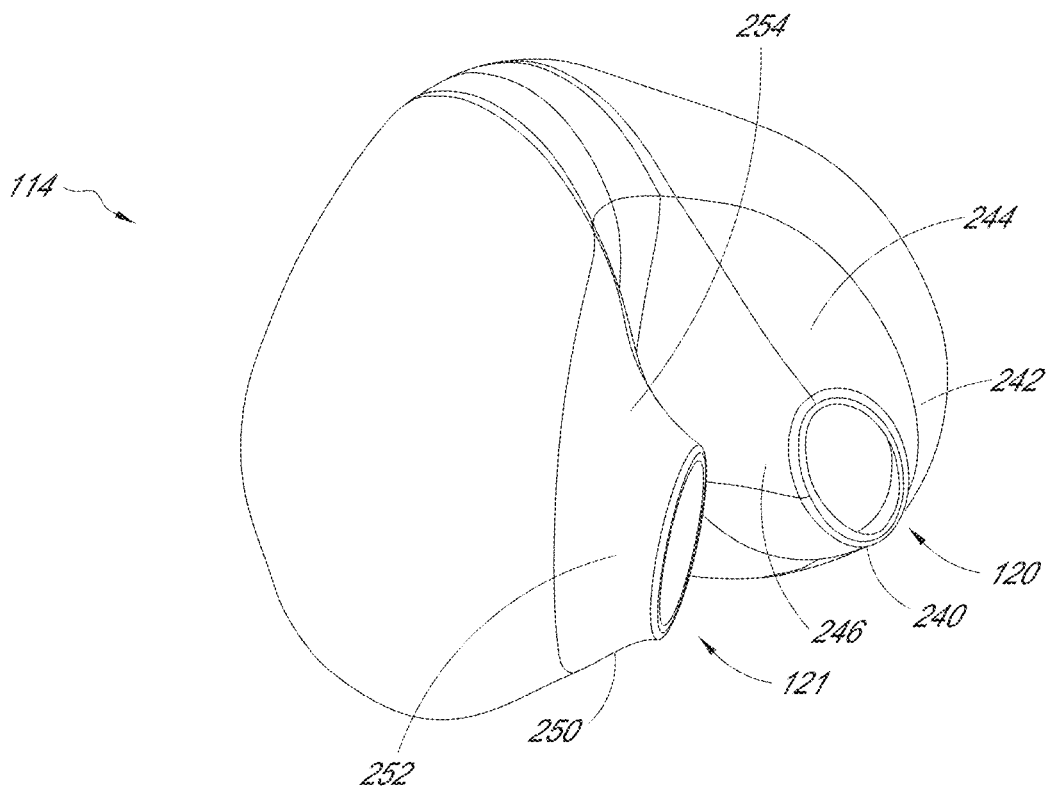
FIG. 10 is a perspective view of the seal of FIG. 5.

FIG. 9 illustrates rolling portions 302 and 304. As shown in FIG. 9, the rolling portion 302 is generally larger than the rolling portion 304. One characteristic of the rolling portion 302 that is larger than the rolling portion 304 is the magnitude of the overshoot, identified generally by the reference numeral 320. As illustrated in FIG. 9, the overshoot 320 is larger than the overshoot 322. In some embodiments, the overshoot 320 can be approximately 1 millimeters and the overshoot 322 can be approximately 0.5 millimeters.

Another differentiating characteristic of the rolling portions 302 and 304 is the radial dimensions of the rolling portions 302, 304. For example, as shown in FIG. 9 the rolling portion 302 has a radial dimension 324 that is larger than a corresponding radial dimension 326 of the rolling portion 304. In some embodiments, the radial dimension 324 is approximately 8 mm. In some embodiments, the radial dimension 326 is approximately 3 mm.

These dimensional differences provide a differential rolling propensity of the rolling portions 302 and 304. For example, the larger overshoot 320 and larger radial dimension 324 can cause the rolling portion 302 to roll more readily and through larger magnitudes of rolling deformation than the rolling portion 304.

As such, although the rolling area 300 can extend around the entire periphery of the inlet orifice 130, it can be configured to more readily roll and deform at the distal portions of the seal 114. Thinner wall sections, near the inlet orifice 130, for example, in the rolling area 300, can help determine points at which rolling deformation is initiated or greater in magnitude.

The rolling area 300 can act as a shock absorber that can isolate effects of hose drag, for example, forces on the conduit 106 and tension that may be generated in the head gear or strap 104 (FIG. 1), preventing those forces or tensions from affecting the seal performance. This can help reduce the likelihood that the nostril prongs 120, 121 are pulled away from the patient's nose 200, thereby preventing or reducing the likelihood of leaking.

With reference to FIG. 9, during use, the inlet orifice 130 can be relatively close to the upper lip of the user. Thus, lower portions of the frame 116 and connector 112 can also be close to the upper lip of the user. Thus, by providing the rolling section 304 with smaller dimensions and or larger thicknesses can provide the optional benefit of a lower propensity for rolling. Optionally, the rolling portion 304 can be configured for very little rolling in this area. Such rolling portions 300 can help reduce the likelihood that the seal 114 will collapse on the patient's lip or other parts of the face, thereby providing an enhanced degree of stability that helps maintain the position of the sealing surfaces relative to the lower nasal surfaces of the user's nose 200. Optionally, the rolling portion 302 can have a continuous curve to thereby increase the likelihood that the portion 302 will roll rather than collapse or fold during use.

FIGS. 12-31 illustrate a modification of the seal 114, identified generally by the reference numeral 1114. Parts, components, and features of the seal 1114 which are similar or the same as corresponding parts, components, or features of the seal 114 are identified with the same reference numeral, except that 1000 has been added thereto.

With reference to FIGS. 12-19, the seal 1114 can include the same features of the seal 114 noted above with respect to asymmetric prongs, convex sealing surfaces, semi-inflating, lip engagement, and rolling. Thus, those features which can optionally be embodied in the seal 1114, are not further described below.

The seal 1114 includes an optional configuration for enhancing response to lateral forces and a rolling movement accommodated by the lateral walls 1125, 1126.

Figure 16:
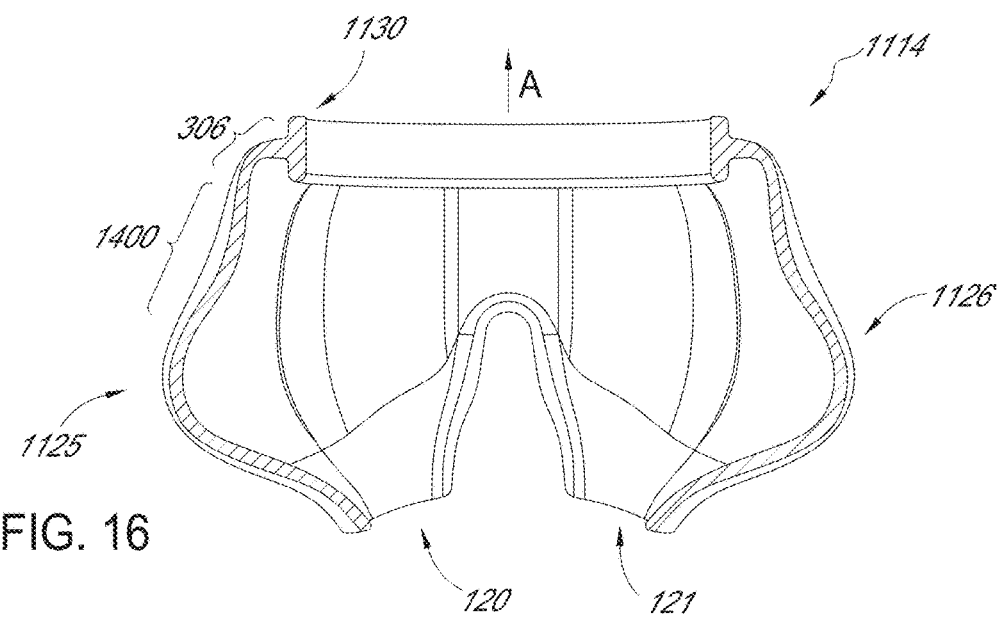
FIG. 16 is a sectional view of the seal taken along line 16-16 of FIG. 13.
Figure 17:
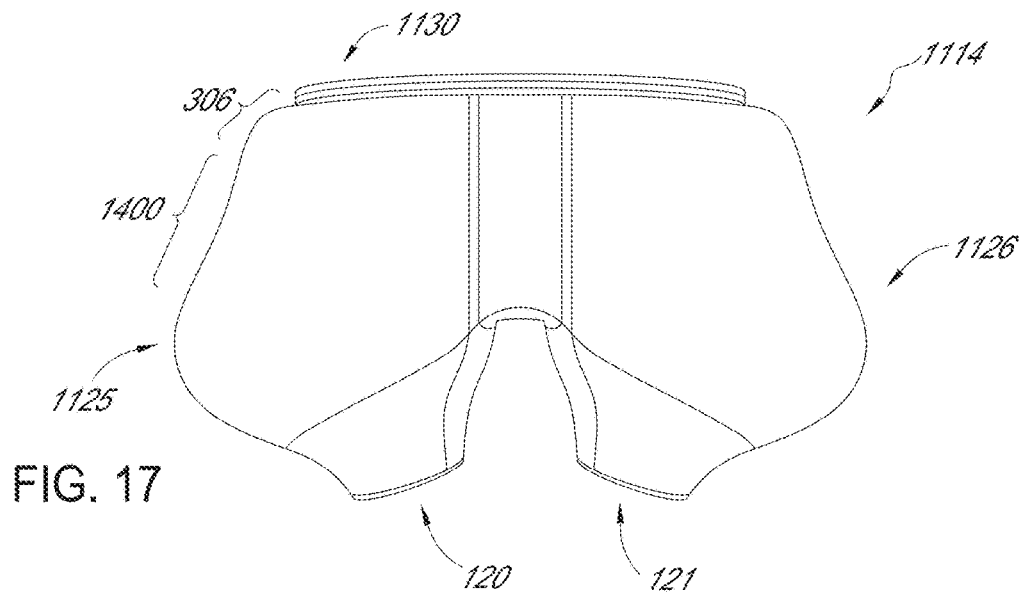
FIG. 17 is a top plan view of seal of FIG. 12.
Figure 18:
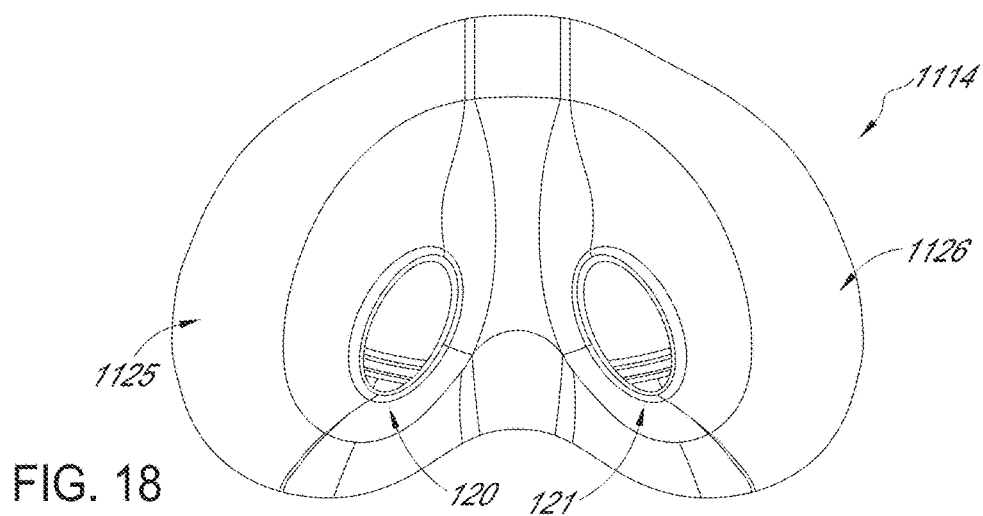
FIG. 18 is a skewed view of the seal of FIG. 12 as viewed in the direction of arrow A of FIG. 2.

With reference to FIG. 16, the lateral wall 1125 can be considered as extending from the nostril prong 120, in the direction of arrow A, toward the inlet orifice 1130. The seal 1114 can optionally include the rolling portion 306 in the area proximal to the inlet orifice 1130. Additionally, the seal 1114 can include an additional rolling portion 1400 in the lateral wall 1125. The seal 1114 can include an additional rolling portion 1400 in the lateral wall 1126. For brevity, the description set forth below of the rolling portion 1400 only with reference to the lateral wall 1125, however, this description also applies equally to the lateral wall 1126.

Figure 19:
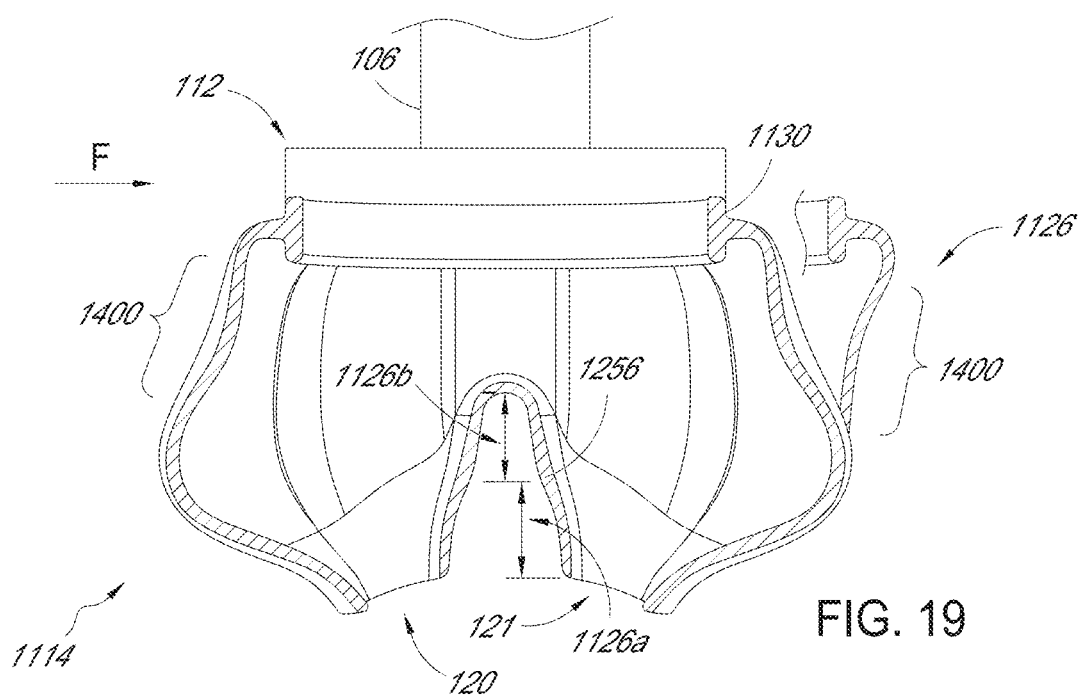
FIG. 19 is a sectional view of the seal taken along line 16-16 of FIG. 13 and illustrating a lateral movement.
Figure 20:
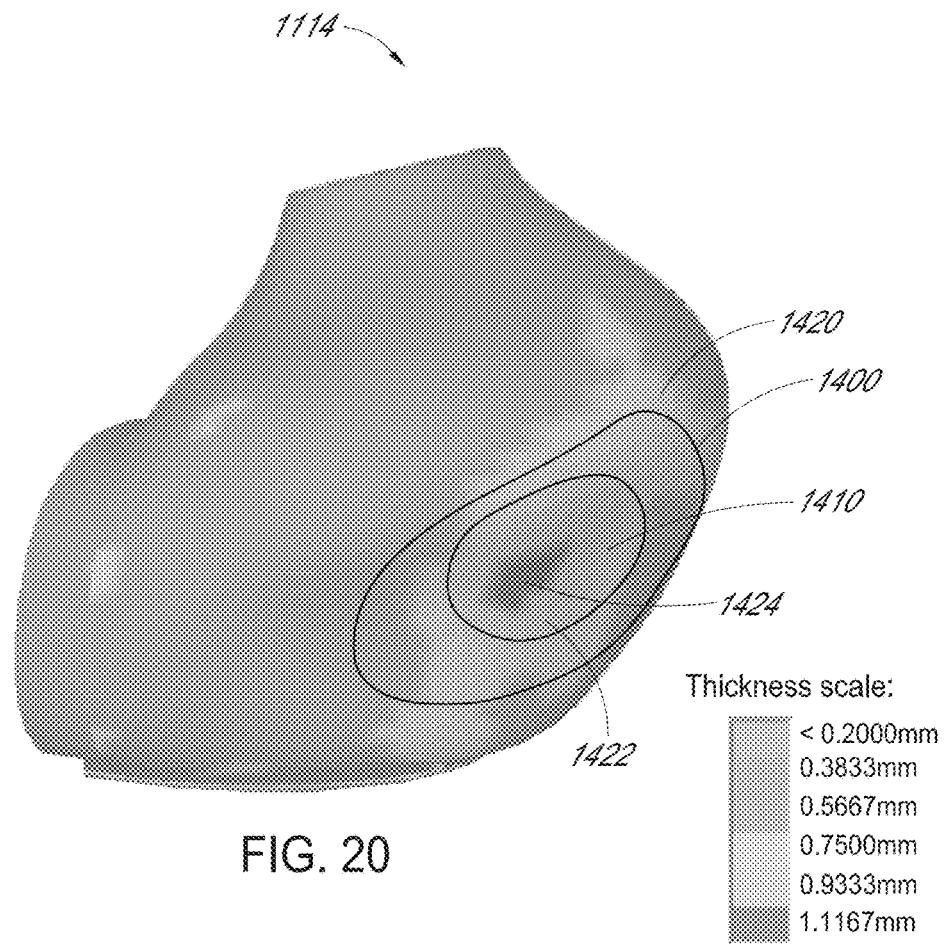
FIG. 20 is a top, front and left side perspective view of the seal member of FIG. 12, including shaded contours corresponding to optional thicknesses.

With reference to FIG. 19, as noted above with reference to the seal 114 and FIG. 7a, the medial portion 1256 comprises an upper portion 1256a and a lower portion 1256b. The upper portion 1256a can be angled, with respect to plane P, at approximately 10 degrees, 0-15 degrees, 0-5 degrees, 5-10 degrees, 10-15 degrees, 5-15 degrees, greater than 0 degrees, or various sub-ranges of 0-15 degrees. The lower portion 1256b of the medial portion 1256 can be angled, with respect to plane P, at approximately 20 degrees, 0-30 degrees, 0-20 degrees, 10-30 degrees, 15-25 degrees. In some embodiments, the upper portion 1256a of the medial portion 1256 comprises up to one half of the medial portion 1256.

Figure 12:
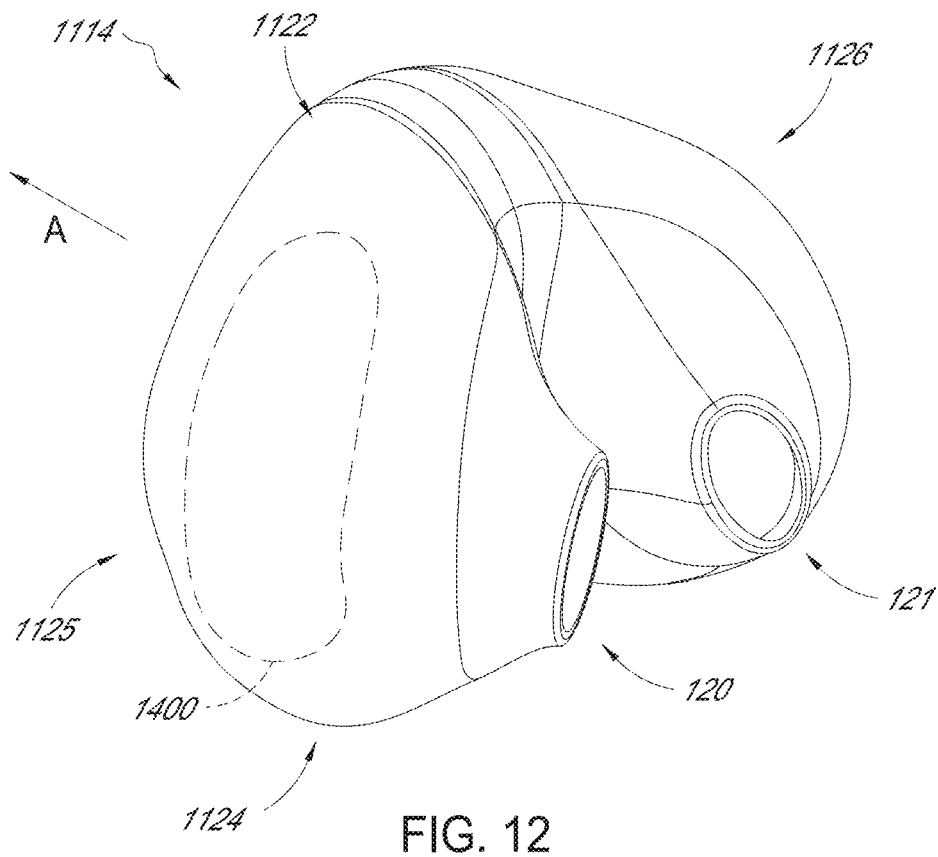
FIG. 12 is a perspective view of a modification of the seal of FIGS. 5-11.
Figure 13:
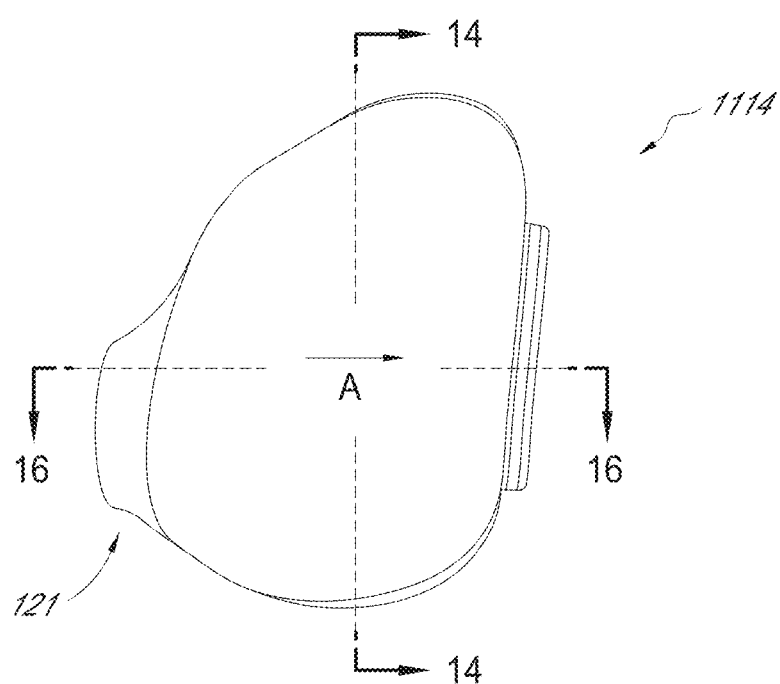
FIG. 13 is a side elevational view of the seal of FIG. 12.

As viewed in the cross-section of FIG. 16, the rolling portion 1400 can comprise a concave portion of the lateral wall 1125. With reference to FIG. 12, the concave portion 1400 can extend across the lateral wall 1125, in the circumferential direction around the seal 1114. Optionally, portions of the concave portion 1400 can extend onto portions of the distal wall 1122 and the proximal wall 1124. As noted above, the lateral 1126 can include the same or similar concave portion 1400.

By including a concave portion 1400 along the lateral wall 1125, between the nostril prong 120 and the rolling portion 306, the concave portion 1400 can help facilitate a more dispersed and larger magnitude rolling deformations. For example, with reference to FIG. 19, when a user is wearing a mask including the seal 1114, a lateral force F can cause deformation of the seal 1114. The force F can be caused by numerous different sources. For example, the force F can be generated when a user sleeps on their side with the side of their head resting on a pillow. In such as position, the pillow can push on a side of the seal 1114, frame 116 or the conduit 106. The force F can be caused in other ways as well.

In response to the force F, the seal 1114 can deform, for example, the inlet orifice 1130 can be pushed laterally towards the right, as viewed in FIG. 19, causing the side wall 1126 to deform, allowing the inlet orifice 1130 to move laterally relative to the nostril prongs 120, 121. This is also known as a "racking" motion. The concave portions 1400 can help allow the side walls 1125, 1126 to rack in response to the force F and thus more readily allow the motion to be accommodated without collapsing the seal 1114. In addition to "racking" motion, there may be some rolling or rotating (not shown) of the inlet orifice 1130 in response to the force F.

Figure 14:
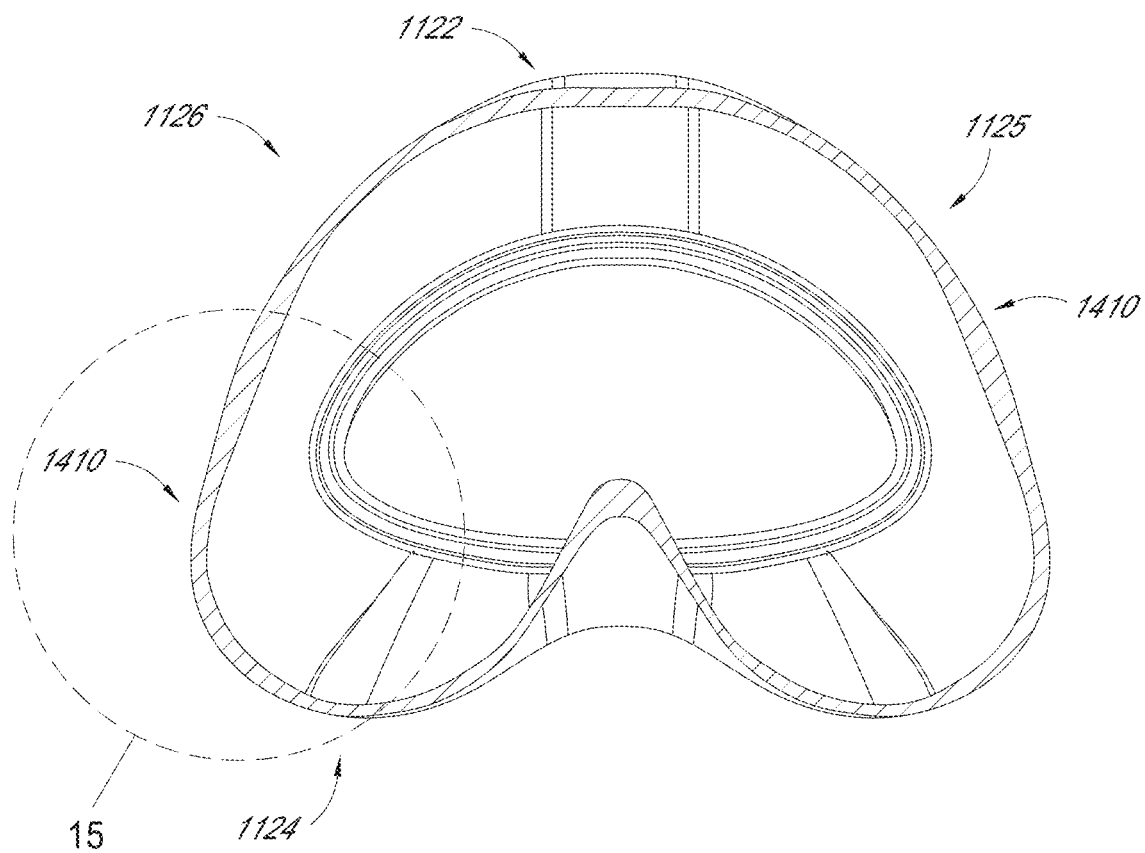
FIG. 14 is a sectional view of the seal taken along line 14-14 of FIG. 13.
Figure 15:
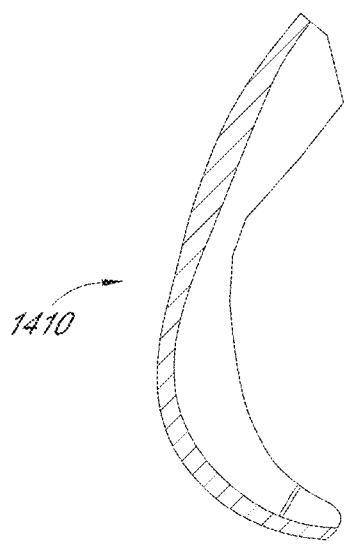
FIG. 15 is an enlarged view of a portion of the sectional view of FIG. 14.

With reference to FIGS. 14 and 15, the seal 1114 can also include a thickened area 1410. As shown in FIG. 14, the thickened area 1410 can be approximately centered in the lateral walls 125, 126. Thus, as shown in the sectional view of FIG. 14, as the lateral wall 126 extends from the proximal wall 1124 toward the distal wall 1122, the thickness of the lateral wall 1126 starts from a thinner thickness adjacent to the proximal wall 1124, thickens in the thickened portion 1410, then reduces thickness again in the portions approaching the distal wall 1122. In some embodiments, the portions adjacent to the proximal wall 1124 can be in the range of 0.7 to 0.9 millimeters. The thickened portion can have a thickness of 1.2 millimeters, and the portions of the lateral wall 1126 adjacent the distal wall 1122 can have a thinner thickness, for example, 0.7 millimeters. The above mentioned thicknesses are merely example and are not intended to be limiting.

Figure 21:
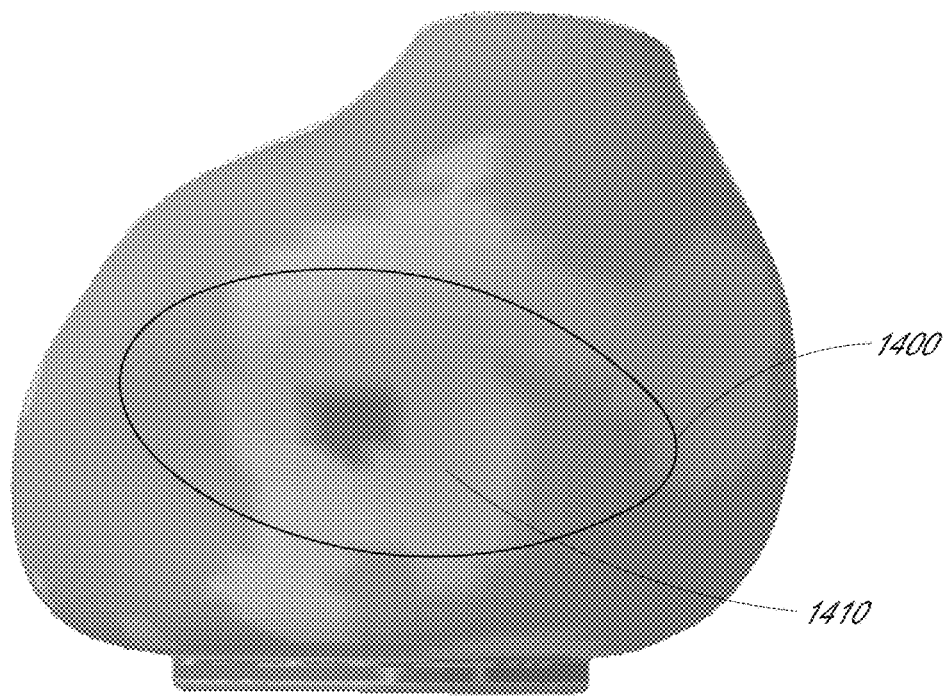
FIG. 21 is a left side elevational view of the seal with the thickness shading of FIG. 20.
Figure 22:
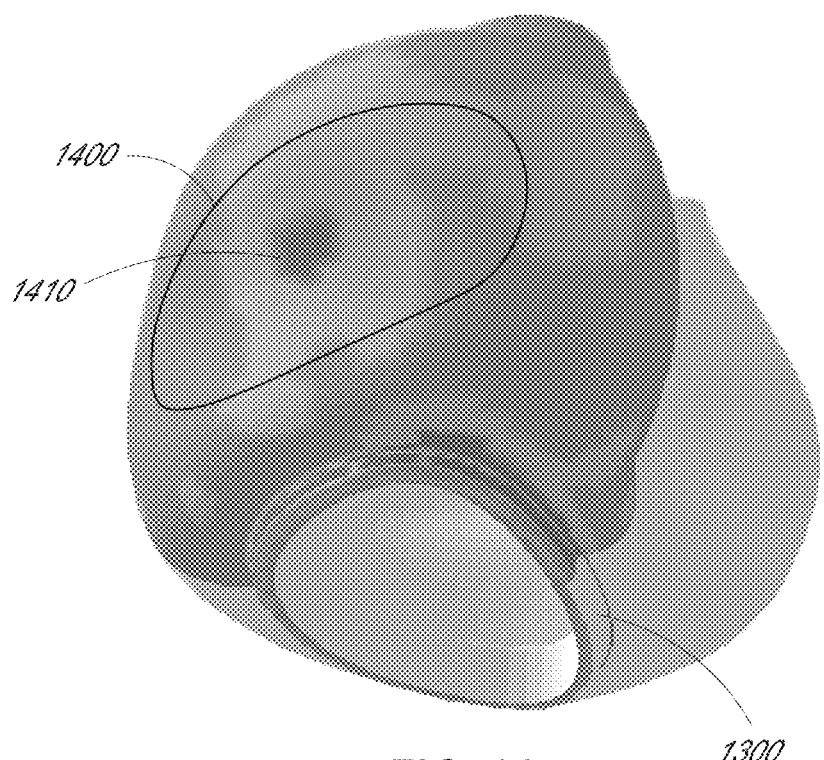
FIG. 22 is a bottom, rear and left side perspective view of the seal with the thickness shading of FIG. 20.
Figure 23:
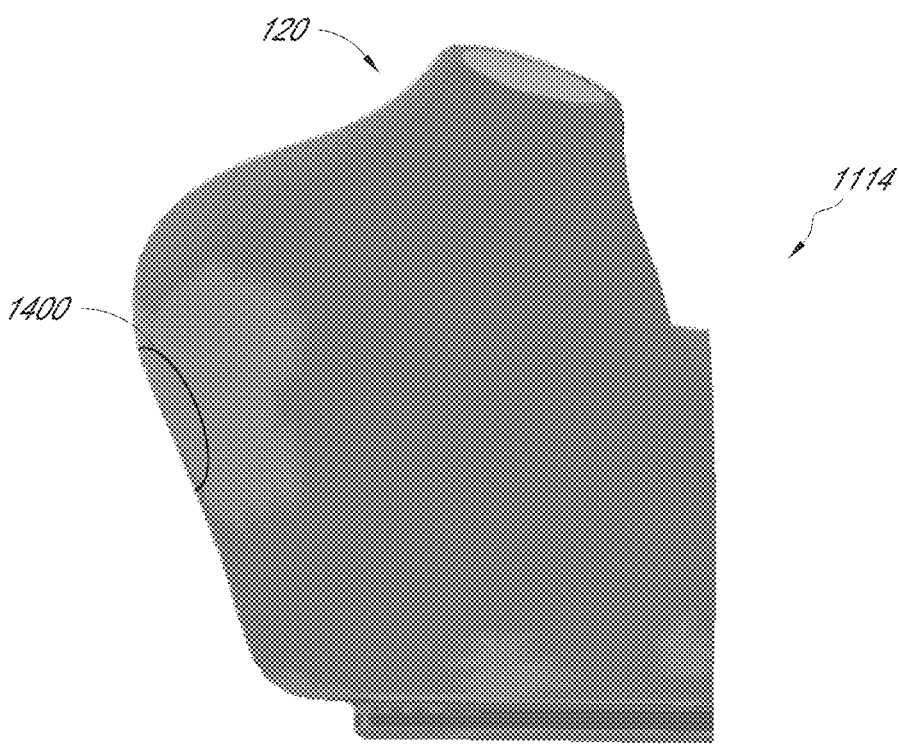
FIG. 23 is a rear elevational view of the seal and with the thickness shading of FIG. 23.
Figure 24:
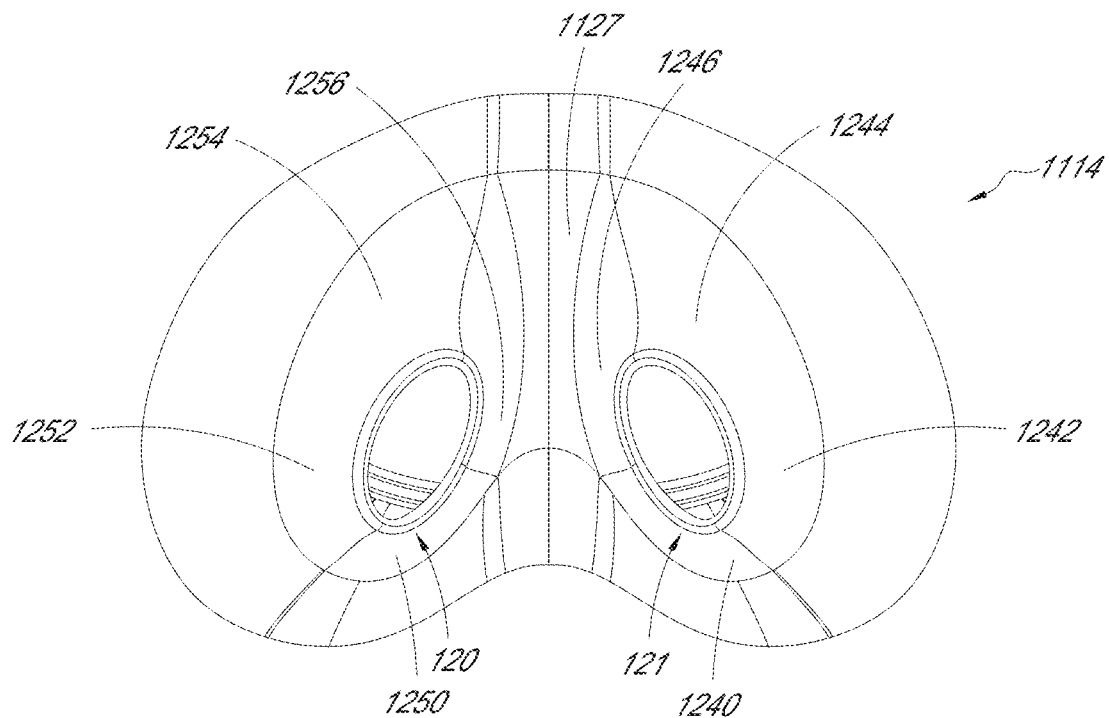
FIG. 24 is a skewed view of the seal of FIG. 12 taken along a direction identified by arrow A of FIG. 2, and including schematic lines and shading as optional boundaries of different portions of the seal.
Figure 25:
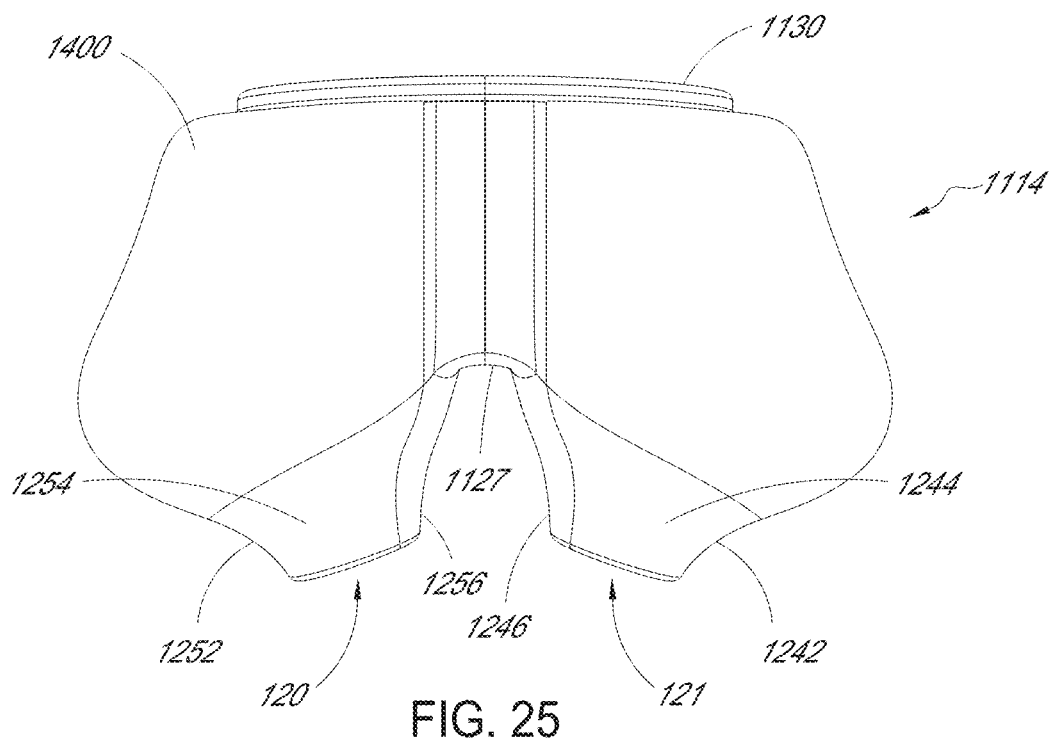
FIG. 25 is a top plan view of the seal of FIG. 20.
Figure 26:
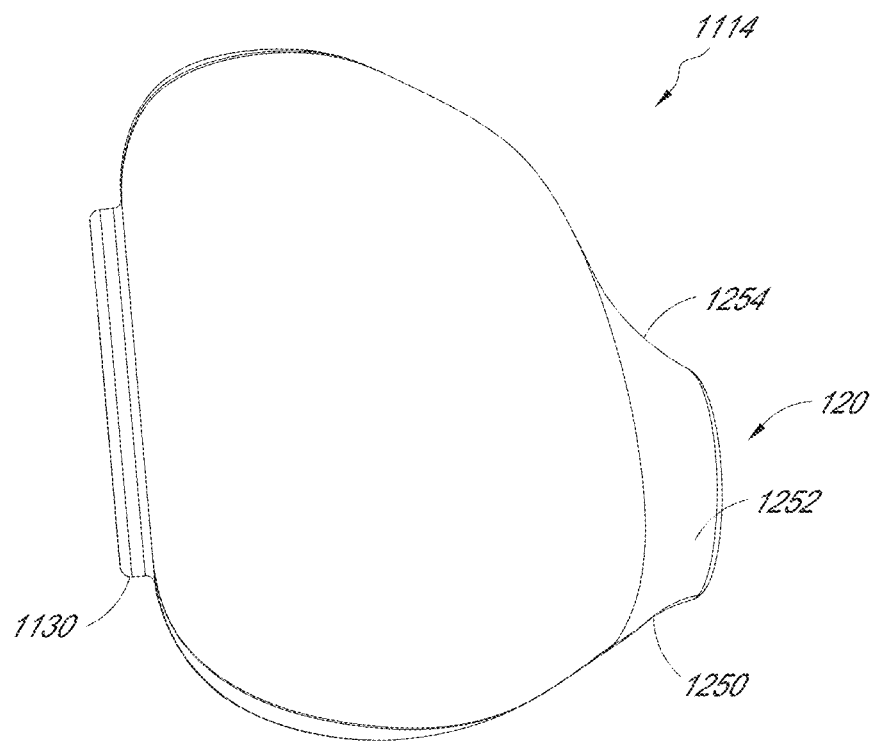
FIG. 26 is a side elevational view of the seal of FIG. 20.
Figure 27:
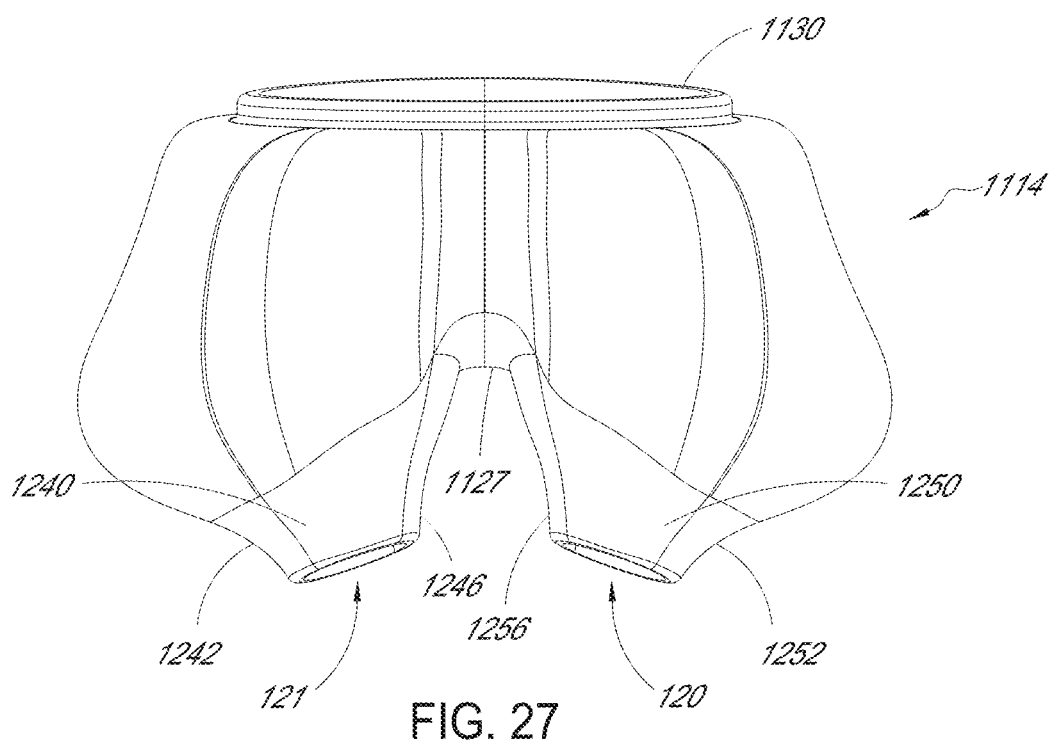
FIG. 27 is a bottom plan view of the seal of FIG. 20.
Figure 28:
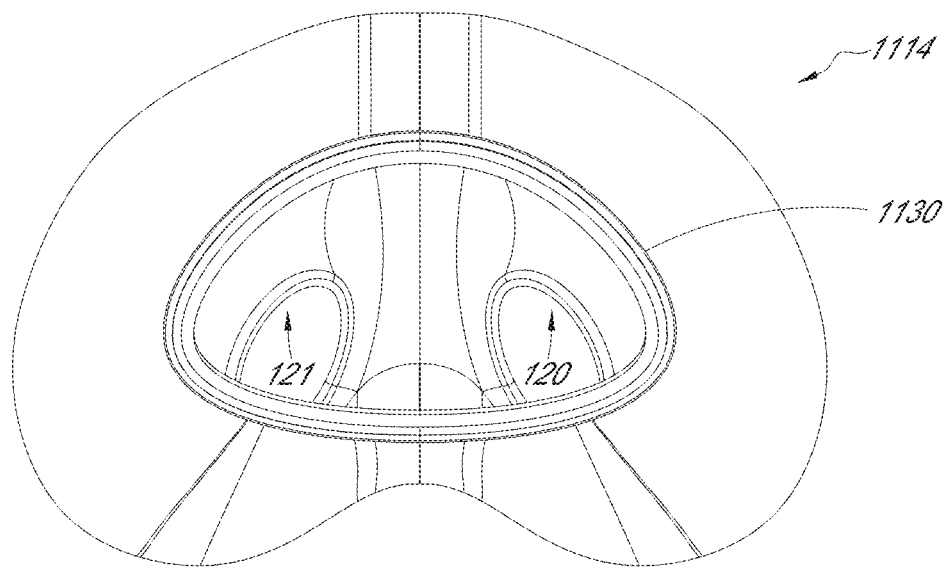
FIG. 28 is a front elevational view of the seal of FIG. 20.
Figure 29:
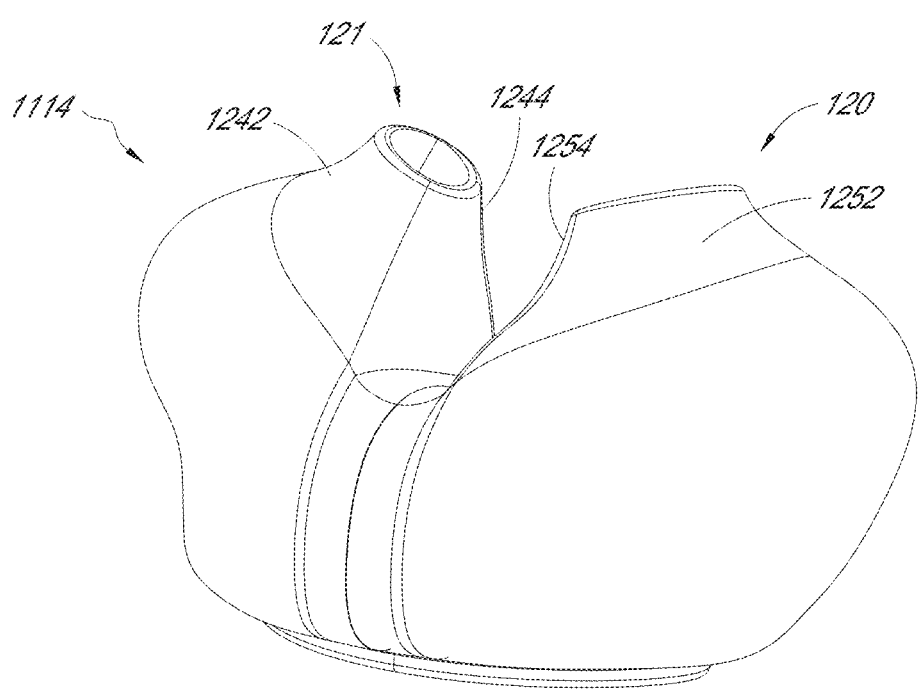
FIG. 29 is perspective view of the seal of FIG. 20.
Figure 30:
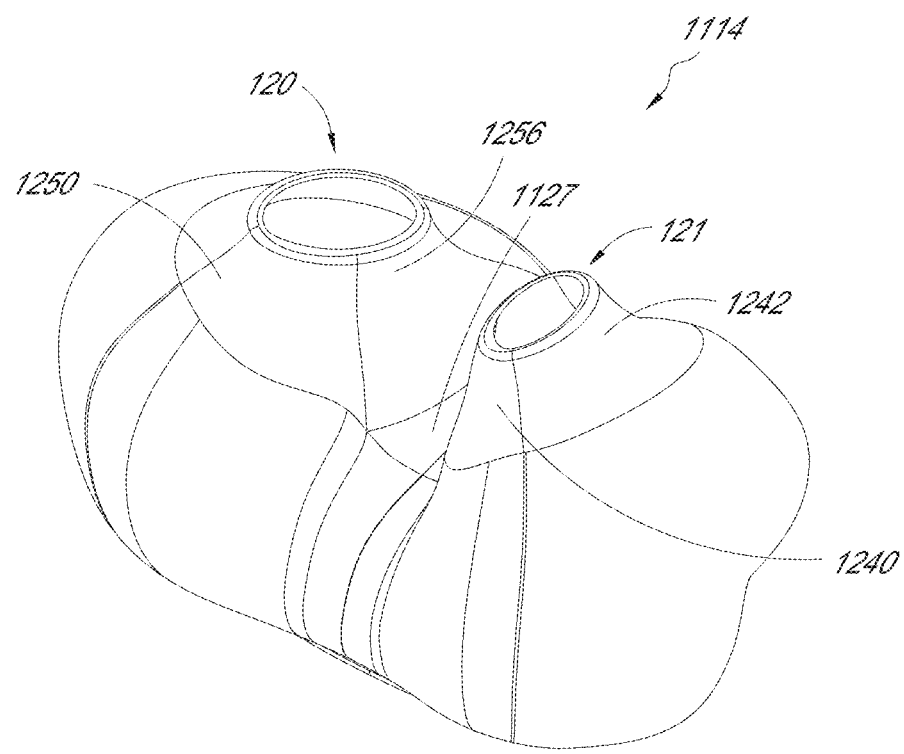
FIG. 30 is a rear, right, and bottom perspective view of the seal of FIG. 20.
Figure 31:
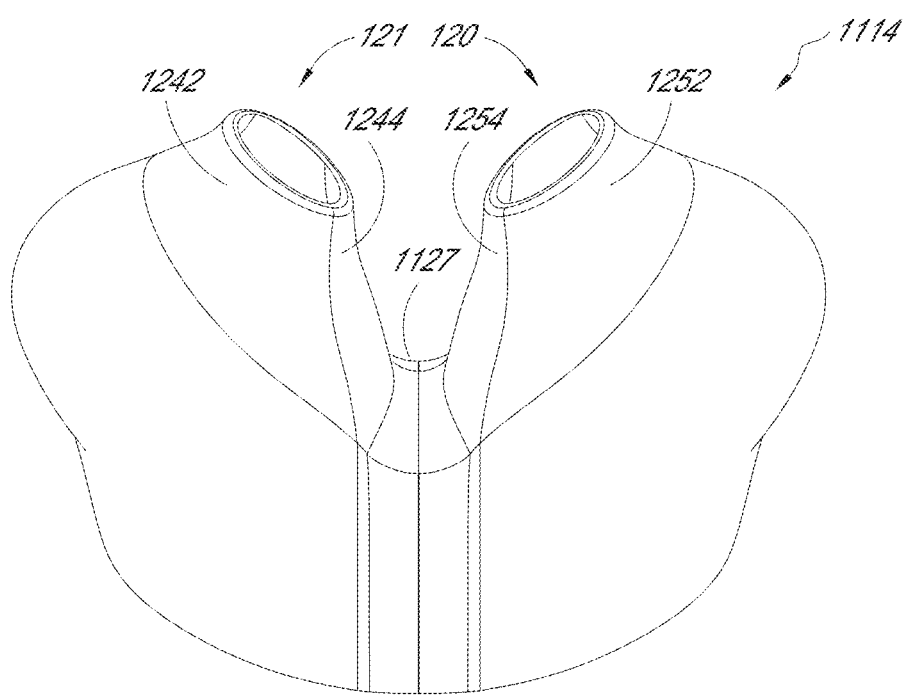
FIG. 31 is a perspective view of the seal of FIG. 20.
Figure 32:
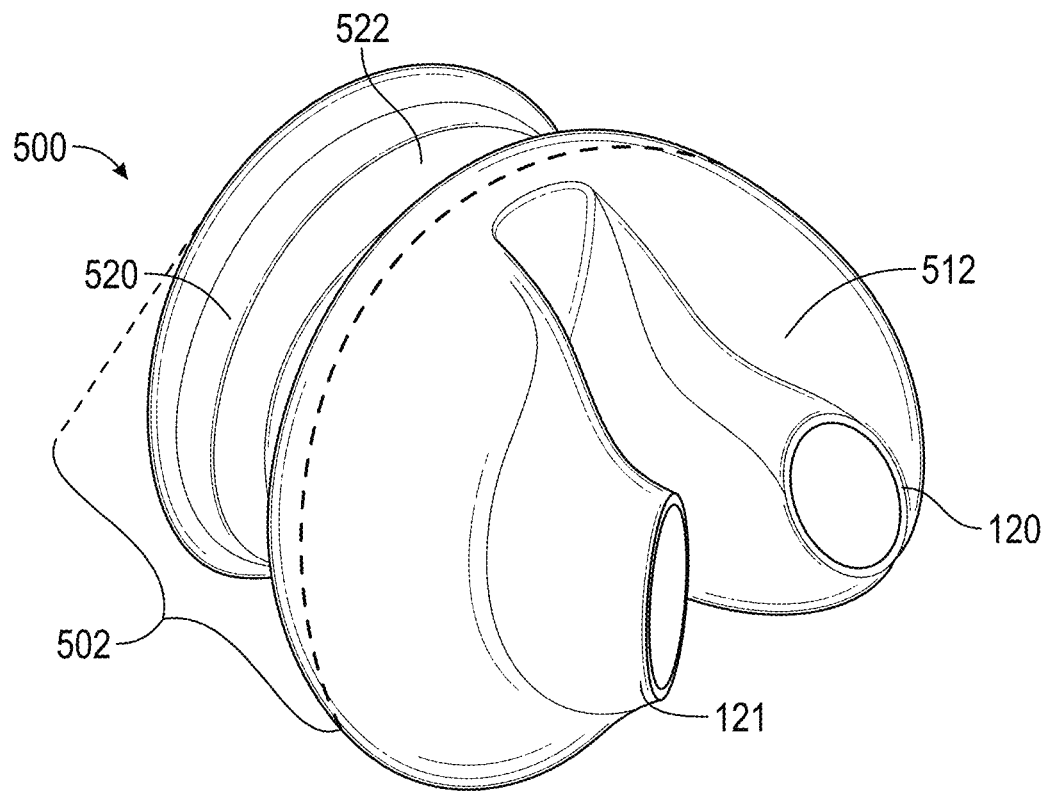
FIG. 32 is a perspective view of an example embodiment of a seal including a bellows.

With reference to FIGS. 20-23, the thickened portion 1410 of the seal 1114 can be roughly circular and can optionally be disposed within the concave portion 1400. As shown in the various views of FIGS. 20-23, the areas indicated by shading 1420 can be approximately 0.75 millimeters, the thickness of the region shaded 1422 can be approximately 0.9 millimeters, and the thickness of the region shaded 1424 can be approximately 1.1 millimeters. These thicknesses are merely examples of an embodiment, and other thicknesses can be used. As shown in FIGS. 21-23, additional thickened areas can be disposed near the rolling portion 1300. FIG. 64 illustrates another embodiment of a seal including a thickened region 830. The thickened region 830 can be 2.0 mm adjacent or near the inlet orifice 130, taper to 1.2 mm moving toward the prongs 120, 121, and can be 0.8 mm in a remainder of the seal including the sealing surface.

The additional rolling structure provided to the lateral walls 1125, 1126 can provide for additional comfort and sealing performance. The concave portion 1400 and/or the thickened portion 1410 can provide an additional rolling section that forms a cushion and can act as a shock absorber, such that movement of the sealing surfaces extending around the nostril prongs 120, 121 and the movements of the frame 116 can be more isolated from one another. The concave portion 1400 can extend on portions of the seal 1114 forward from the patient's face and on lateral walls 1125, 1126, as described above.

The concave sections 1400 can be configured to provide more stability under lateral, side-to-side movement of the seal 1114, such as that illustrated and described above with reference to FIG. 19. An additional benefit is that the concave portions 1400 can help reduce the overall visual appearance of the sides of the seal 1114, improving patient acceptance.

Seal with Bellows

FIGS. 32-42I illustrate an example embodiment of a seal 500 that includes a sealing portion 510 and a lower bellows portion 520. The sealing portion 510 includes nostril prongs 120, 121 and sealing surfaces 512 that form seals with the nostrils of a user during use, which may be similar to other embodiments shown and described herein. In some embodiments, the prong 120, 121 apertures 118, 119 are elliptical as shown. Upper ends of the prongs 120, 121 and apertures 118, 119 can be angled inward such that the prong 120, 121 apertures 118, 119 form an inverted V shape when viewed from the front (or viewed from the perspective of the patient). The lower bellows portion 520 supports the sealing portion 510. The lower bellows portion 520 includes a bellows structure 522 and the inlet orifice 130. The inlet orifice 130 can have an oval or generally oval shape. In some embodiments, the inlet orifice 130 includes a rigid oval ring that acts as a connector for e.g., a frame or conduit.

The bellows structure 522 extends circumferentially around a portion or an entirety of a base and/or the inlet orifice 130 of the seal 500. The bellows structure 522 allows for linear compression and/or expansion of the seal 500 in an axial direction (e.g., along an axis extending through a center of the inlet orifice 130 and between the prongs 120, 121 as shown by the dashed lines in FIG. 33) as shown by outline 524 in FIG. 34. Such compression and/or expansion can advantageously compensate for and/or isolate hose drag (i.e., forces applied to the seal 500 by a conduit coupled to the inlet orifice 130) and/or can advantageously allow for adaptation to differing facial geometry of different users. The bellows structure 522 can therefore act as a compliant spring and/or resilient portion between the inlet orifice 130 and the prongs 120, 121. In use, the lower bellows portion 520, e.g., the bellows structure 522, is configured to be in a compressed state when the seal 500 is fitted to the user's face. Therefore, if hose drag occurs, the lower bellows portion 520 expands away from the user's face before the sealing surfaces 512 and/or prongs 120, 121 are pulled away from the user's face, which can cause or allow for leaks between the seal 500 and user's face. A greater range of possible compression and extension of the lower bellows portion 520 allows the seal 500 to withstand a greater degree of hose drag. In some embodiments, an initial (i.e., in a relaxed state in which the seal 500 has not been expanded, compressed, splayed, or inflated as described herein) height of the seal 500 (indicated by h1 in FIG. 34) is 32 mm. In some embodiments, when the seal 500 is fully or maximally compressed, a connector coupled to the inlet orifice 130 can be displaced (where the amount of displacement is indicated by h2 in FIG. 34) relative to the sealing surface 512 by up to 12 mm without adversely affecting the performance of the sealing surface 512.

The bellows structure 522 may be any suitable bellows arrangement that permits relative movement between the base and the prongs 120, 121, such as the movement described immediately above or elsewhere herein. For example, the bellows structure 522 may be a structure of reduced cross sectional area or, alternatively, may be a thinner section on the inner side of the wall, or a combination thereof. The bellows section may have a planar outer wall shape/structure (or a curved shape that is continuous with portions of the seal 500 outside of the bellows section) and may have an internal thinning of the wall to result in the same/similar function as the bellows structure 522.

A further alternative arrangement is that the bellows section could be a convex bellows rather than a concave section as shown. The current illustrated embodiment shows a bellows section 522 or a pleat that is concave in shape, but alternatively the bellows section 522 may be a pleat that is convex and extends outwardly. In at least some configurations, the convex bellows would expand outwardly when compressed. Such a convex bellows section can act as a support to prevent the seal from over rotating about the center of the bellows.

The sealing portion 210 can pivot around the center of the bellows structure 522 (for example, as indicated by the curved arrows in FIG. 33) such that the sealing portion 210 can be angled relative to the lower bellows portion 520. Such pivoting can allow the seal 500 to compensate for angled forces applied to the seal 500 by the conduit attached to the inlet orifice 130 and can help inhibit or reduce disturbance to the sealing surface 512 that may result from such angled forces. The pivoting can also allow the seal 500 to adjust for and accommodate variability in the angle of the user's lower nasal surfaces for different users.

Figure 33:
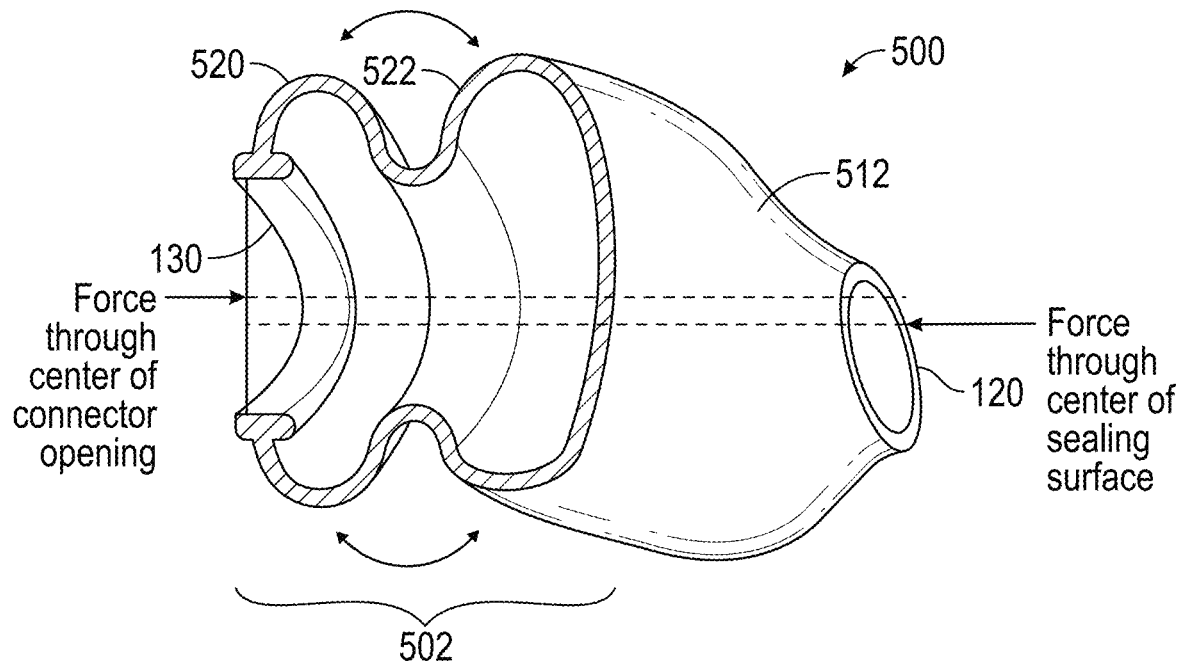
FIG. 33 is a sectional view of the seal of FIG. 32 showing a longitudinal axis and possible pivoting movement of the seal.
Figure 34:
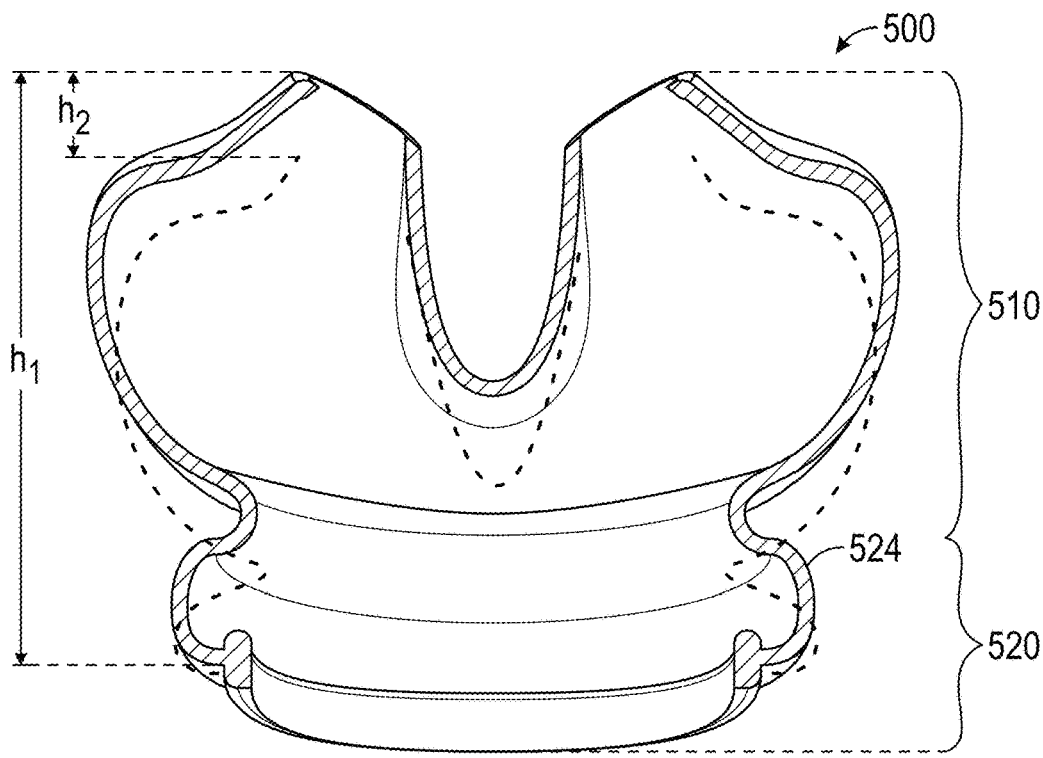
FIG. 34 is a sectional view of the seal of FIG. 32 showing an outline of a compressed profile of the seal.
Figure 35:
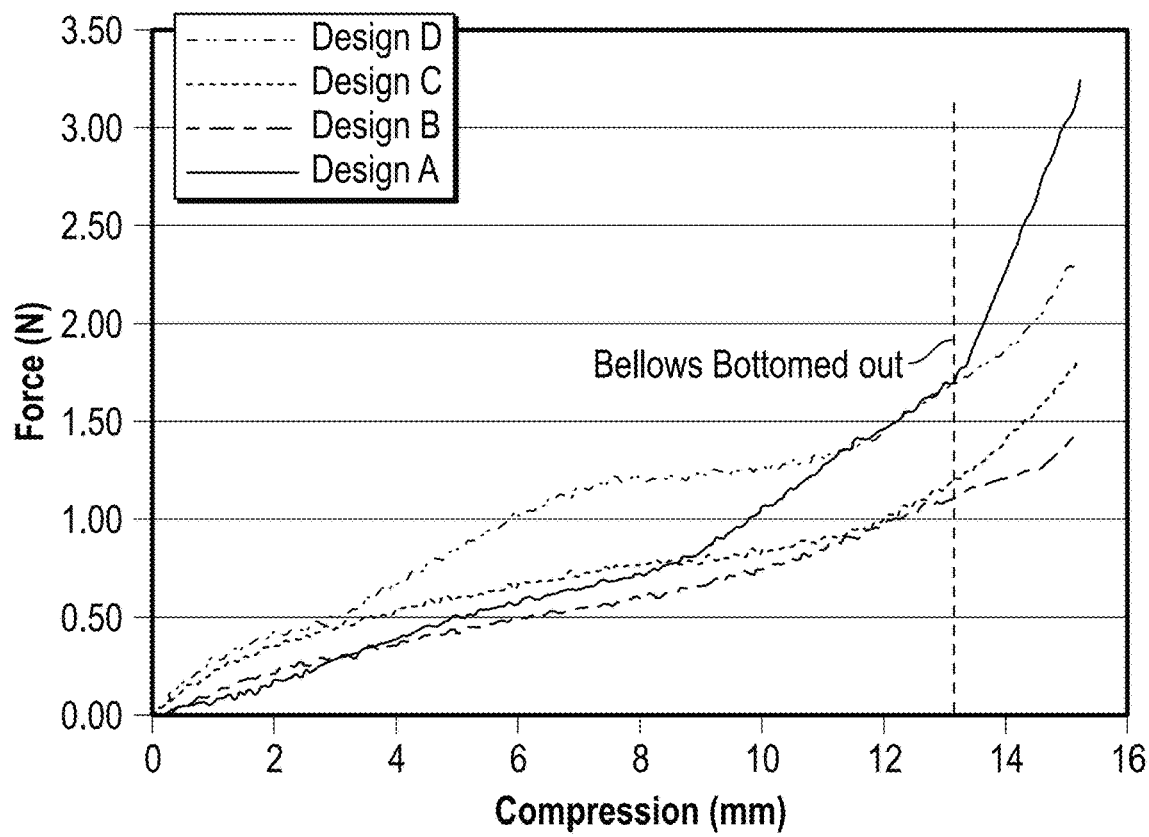
FIG. 35 is a force vs. compression graph.

In some embodiments, the center of the inlet orifice 130 and center of the sealing surface 512 are aligned or approximately aligned, as indicated by the horizontal arrows and dashed lines in FIG. 33. Such alignment can advantageously encourage the bellows structure 522 to compress rather than form a hinge about which the sealing portion 510 and lower bellows portion 520 bend relative to each other. The forces applied to the inlet orifice 130 and the sealing surface 512 can be offset, but oriented in the same direction or parallel to one another. In some configurations, the offset is small relative to a size of the seal 500, such as relative to a cross-sectional dimension of the connector opening 130 or interior cavity of the seal 500.

As shown, the seal 500 can have a rounded cross-sectional profile. In other words, the seal 500 may not have sharp corners. A rounded cross-sectional profile can advantageously promote a smooth compression motion of the seal 500 and a substantially linear increase in force as displacement or compression of the seal 500 increases during at least a portion of the range of compression, as shown in the force vs. extension graph of FIG. 35.

In the illustrated embodiment, the seal 500 has a relatively large inlet orifice 130 in comparison with an overall size of the seal 500 (e.g., cross-sectional dimension of the cavity or other portion of the seal 500). A relatively large inlet orifice 130 can allow the seal 500 to be removed from a mold tool more easily during manufacturing. As shown, a perimeter of the inlet orifice 130 is inwardly offset from an outer perimeter of the lower bellows portion 520. This offset is large enough such that the inlet orifice 130 does not significantly interfere with the function of the lower bellows portion 520 and bellows structure 522.

Figure 36:
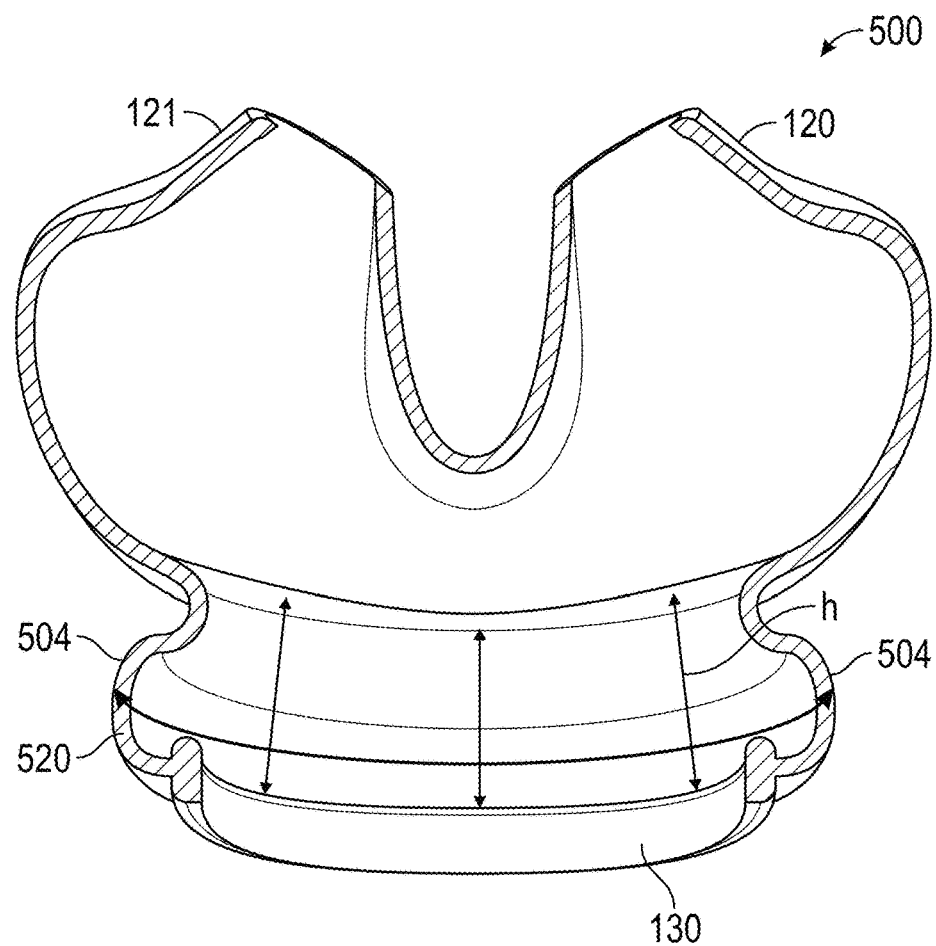
FIG. 36 is a sectional view of the seal of FIG. 32.

As shown by the generally horizontal arrow in FIG. 36, lateral sides of the lower bellows portion 520 can curve toward the sealing portion 510 (upward in the orientation of FIG. 36), such that the lower bellows portion 520 is generally U-shaped. In the illustrated embodiment, a curvature of the lower bellows portion 520 matches or corresponds to (or substantially or generally matches or corresponds to) a curvature of the lower surfaces of the sealing portion 510. In such embodiments, a distance between the lower bellows portion 520 and the lower surfaces of the sealing portion 510 (indicated by the generally vertical arrows in FIG. 36) is substantially the same or equal around an entire circumference of the seal 500. In some embodiments, the distance between the lower bellows portion 520 and the lower surfaces of the sealing portion 510 is 6 mm. A constant distance between the lower bellows portion 520 and lower surfaces of the sealing portion 510 around the circumference of the seal 500 can advantageously allow for a more even compression of the seal 500 around the entire lower bellows portion 520. In other words, the seal 500 is less likely to bottom out in one area of the seal 500 before a remainder of the circumference of the seal 500. The curvature of the lower bellows portion 520 can also give the seal 500 a smaller appearance. In some embodiments, a U-shaped lower bellows portion 520 can advantageously reduce load on the underside of the patient's nose when the headgear is engaged to the patient's face to secure the seal 500 to the patient's face.

Figure 37:
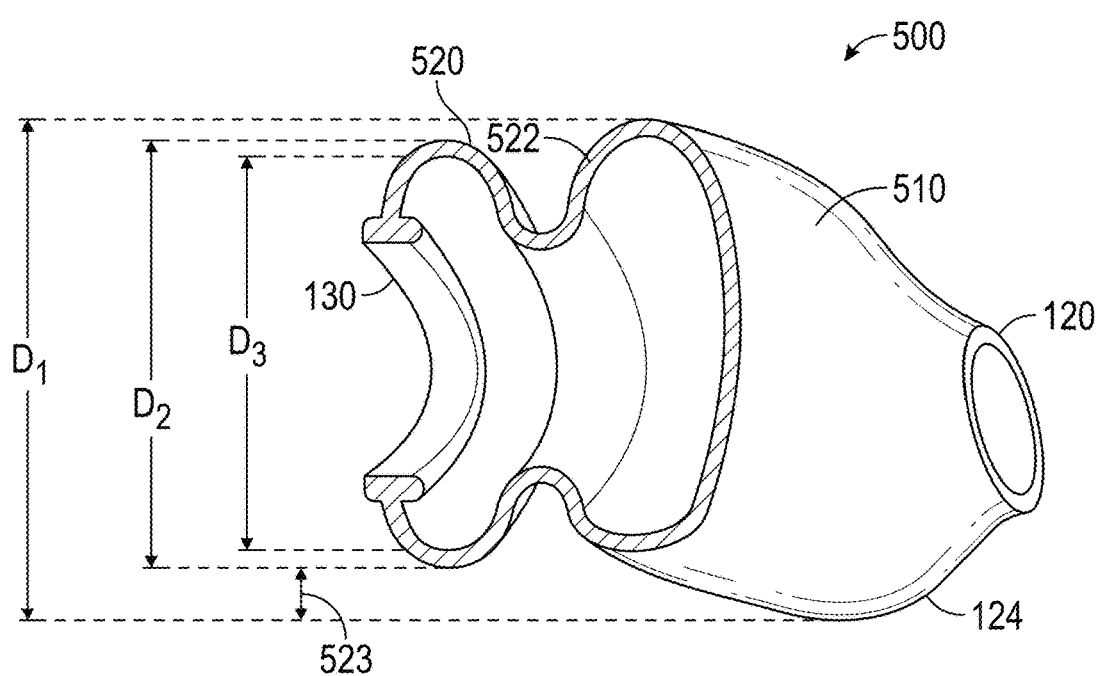
FIG. 37 is another sectional view of the seal of FIG. 32.
Figure 38:
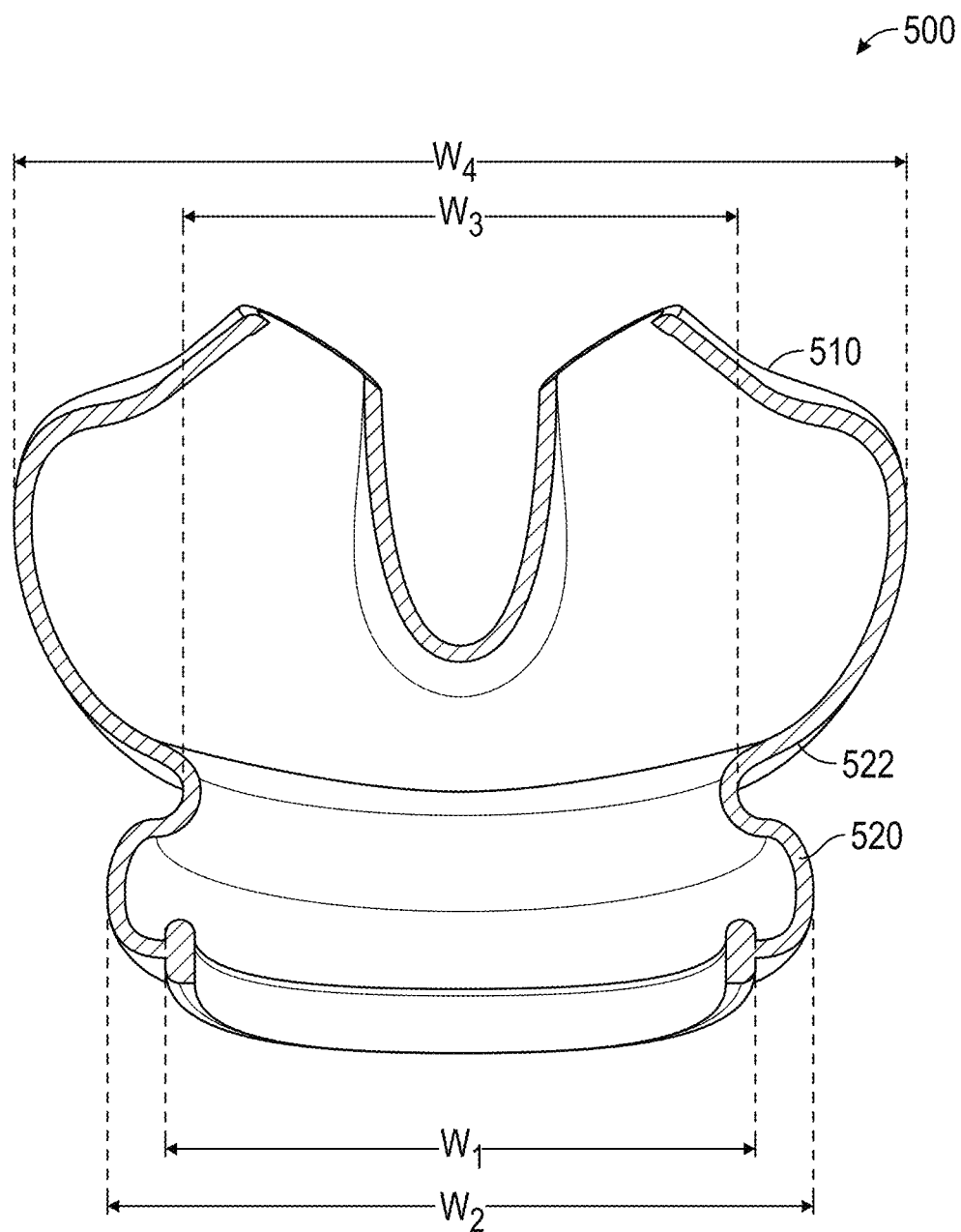
FIG. 38 is a sectional view of the seal of FIG. 32 showing widths of various parts of the seal.
Figure 55A:
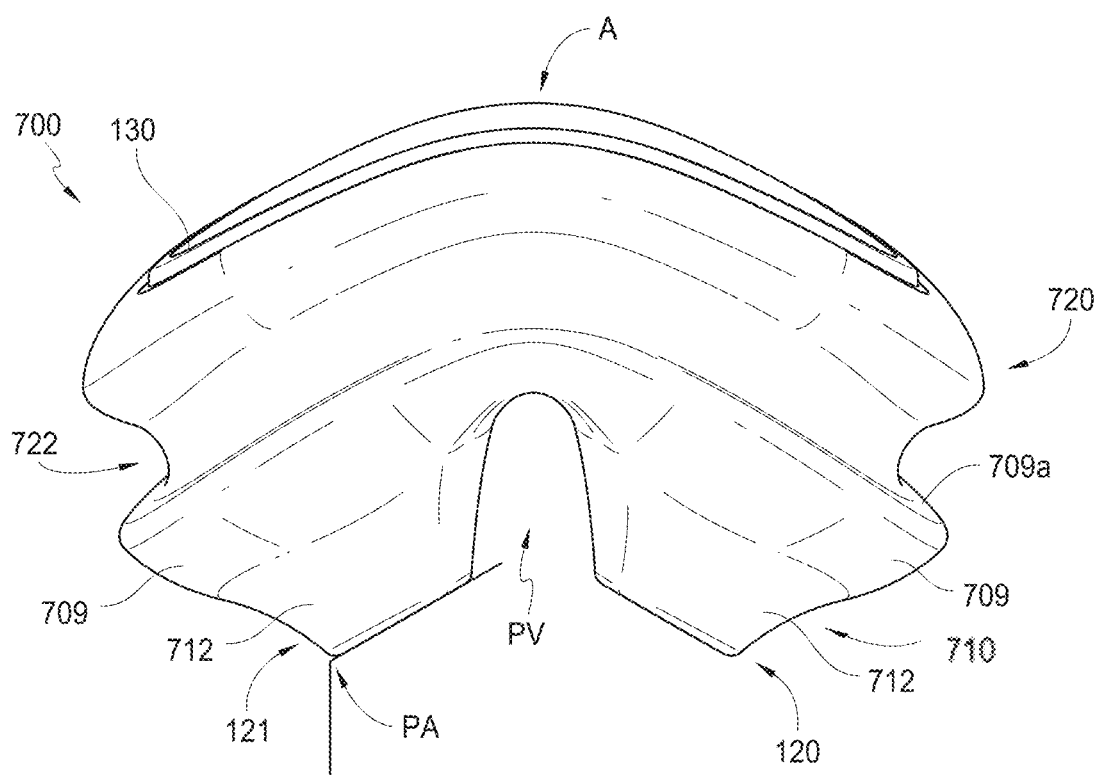
FIG. 55A is a top view of another example embodiment of a seal having a bellows section
Figure 55B:
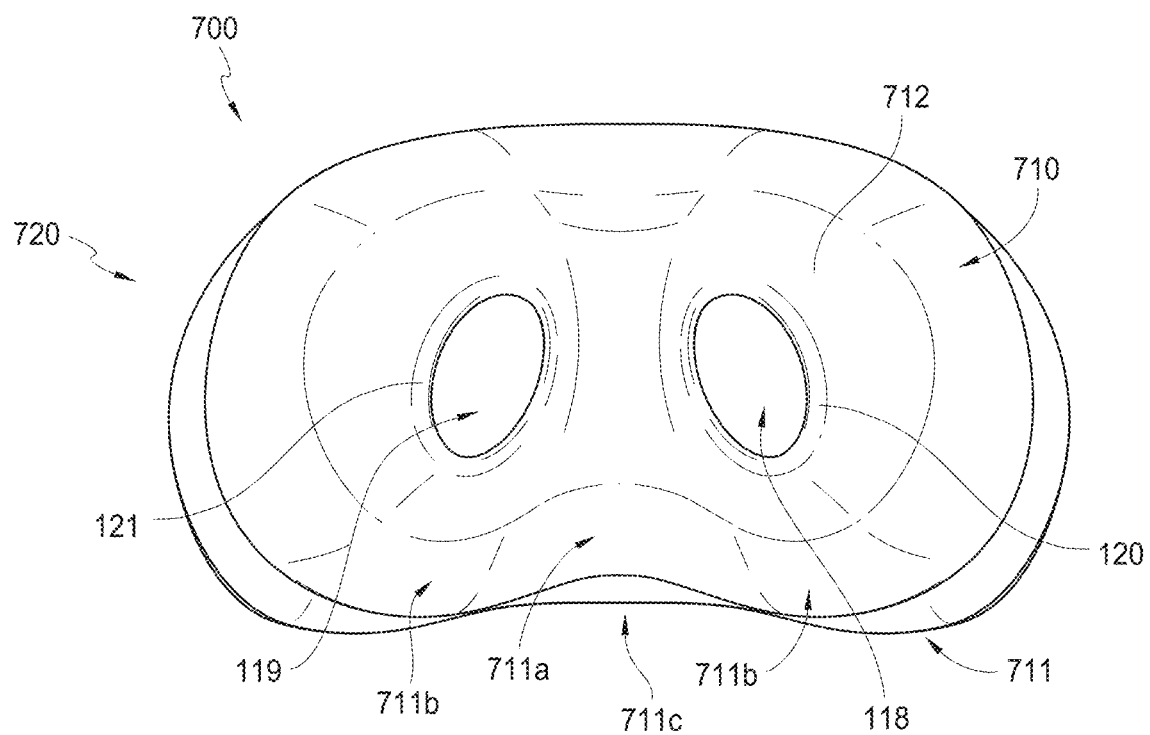
FIG. 55B is a front view of the seal of FIG. 55A.
Figure 55C:
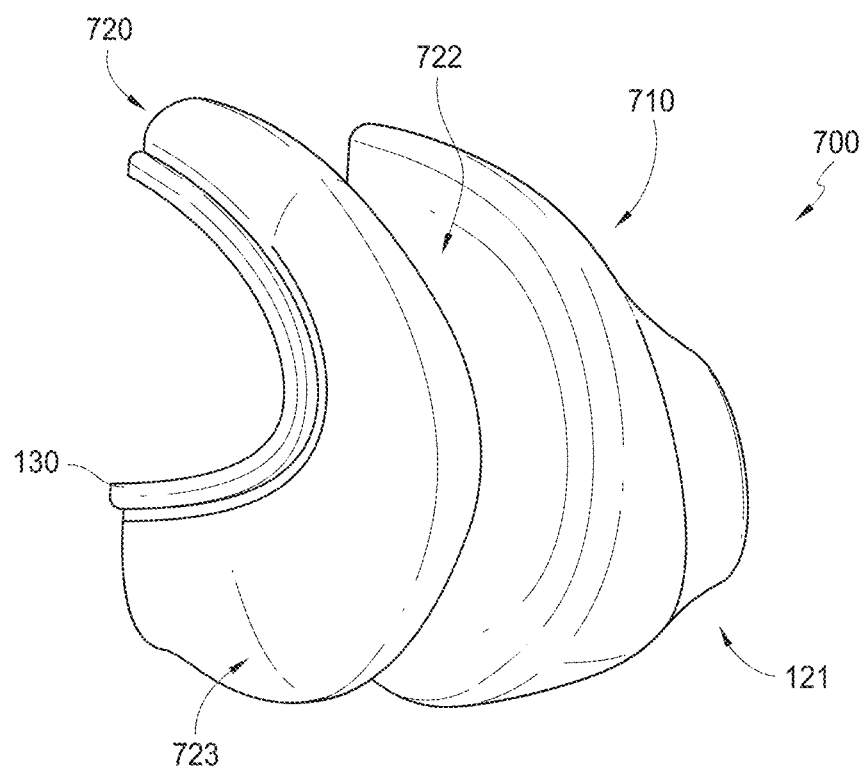
FIG. 55C is a side view of the seal of FIG. 55A.

The perimeter of the lower bellows portion 520 and bellows structure 522 can be smaller than the perimeter of the sealing portion 510 as shown in FIGS. 37-38. A relatively smaller lower bellows portion 520 can advantageously help reduce or minimize the size of the seal 500. As shown in FIG. 37, the lower bellows portion 520 can offset (indicated by arrow 523) from a back of the sealing portion 510 (e.g., from a lowest, in the orientation of FIG. 37, point of proximal wall 124). Such an offset can inhibit the lower bellows portion 520 from contacting the user's lip in use. In some embodiments, the sealing portion 510 has a greatest width (indicated by W4 in FIG. 38) of 43 mm, the inlet orifice 130 has a width (indicated by W1 in FIG. 38) of 28 mm, the lower bellows portion 520 has a greatest width (indicated by W2 in FIG. 38) of 34 mm, and the bellows structure 522 has a width (indicated by W3 in FIG. 38) of 26.5 mm. Such dimensions are exemplary and may vary. However, in some configurations, the relative sizes can be as illustrated. In other embodiments, the perimeter of the lower bellows portion can be larger than the perimeter of the sealing portion, for example as shown in the embodiment of FIGS. 55A-55C.

Figure 39:
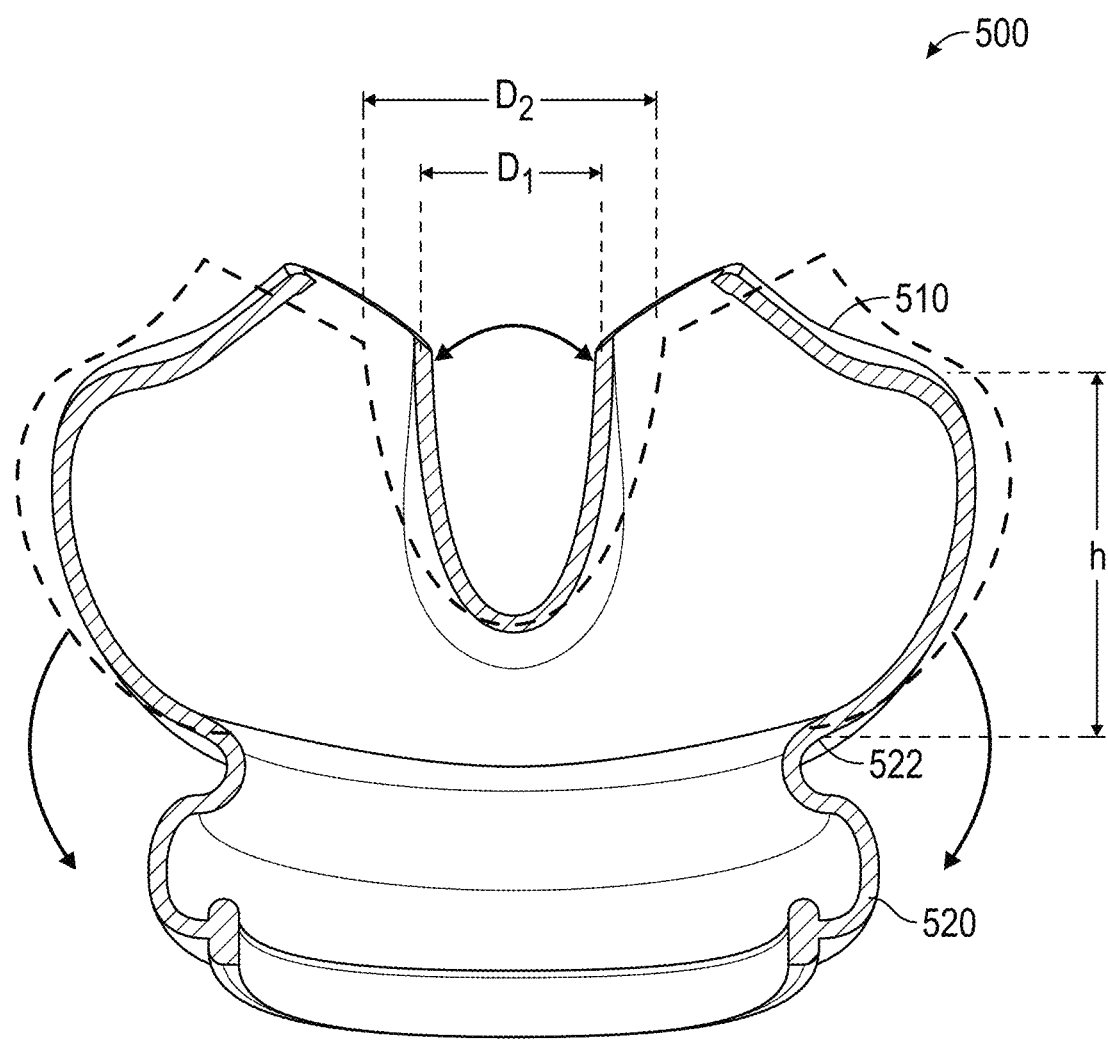
FIG. 39 is a sectional view of the seal of FIG. 32 showing an outline of a splayed profile of the seal.
Figure 40:
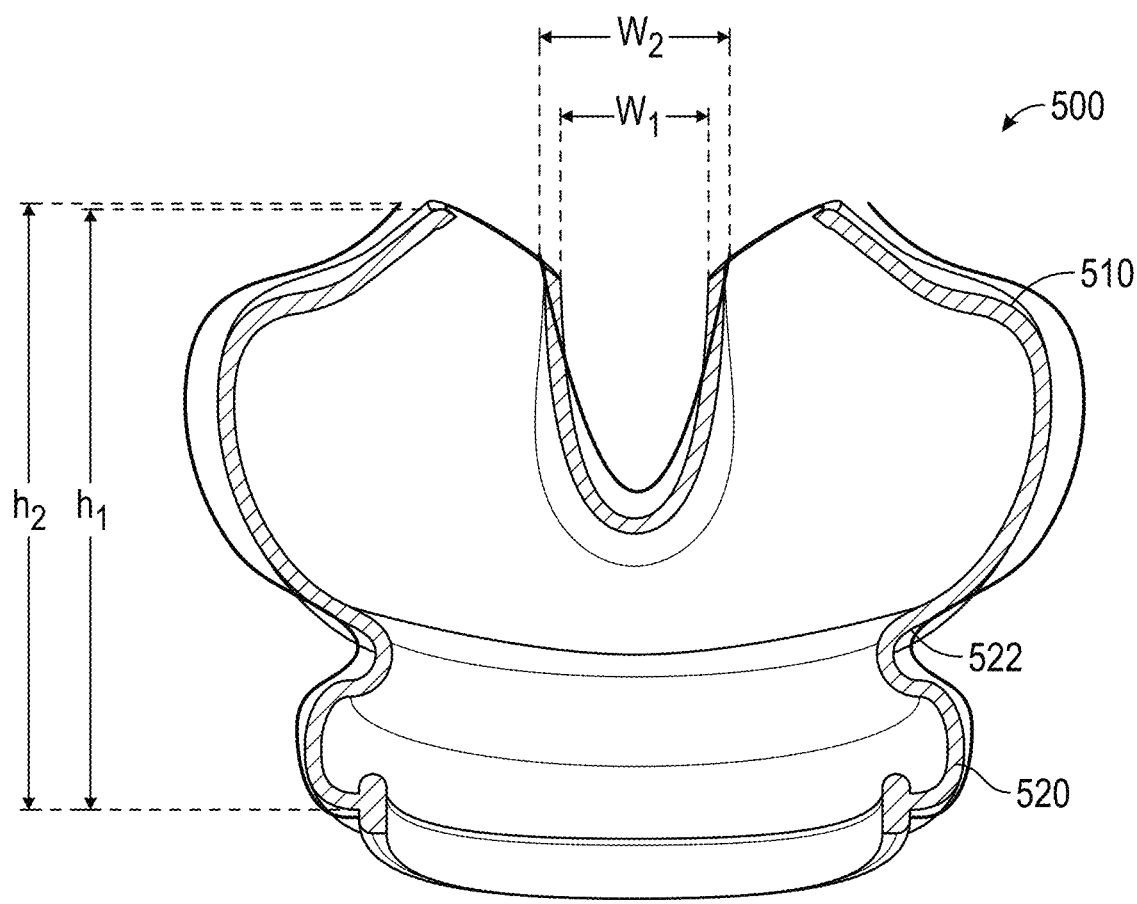
FIG. 40 is sectional view of the seal of FIG. 32 showing an outline of an inflated profile of the seal.

In some embodiments, the sealing portion 510 and/or prongs 120, 121 can flex outwardly or away from each other as indicated by dashed lines showing a flexed or splayed prong profile in FIG. 39. Flexing of the prongs 120, 121 or sealing portion 510 can advantageously allow the seal 500 to accommodate users having relatively large nares and/or nares that are spaced apart by a relatively wide septum. Reducing or minimizing a height of a portion of the sealing portion 510 not including the prongs 120, 121 (indicated by "h" in FIG. 39) advantageously allows for a tight, continuously curved outer surface in the sealing portion 520, which can increase the ability of the prongs 120, 121 to splay outwards without the outer surfaces of the seal 500 collapsing as a shorter, more curved surface is generally less likely to buckle and/or collapse. In some embodiments, the height h is 19 mm. In some embodiments, the prongs 120, 121 can splay outwardly away from each other by 2 mm or more. In some embodiments, a distance between innermost edges of the prongs 120, 121 in a relaxed state is 7.5 mm and a distance between the innermost edges of the prongs 120, 121 is a splayed state is 9.5 mm.

In some embodiments, the seal 500 is semi-inflatable. When the prongs 120, 121 are engaged and sealed with the user's nares and CPAP pressure is applied in use, the seal 500 inflates slightly. The seal 500 can extend or increase in height (along a direction parallel to an axis extending through the center of the inlet orifice 130, indicated by the dashed lines in FIG. 33) and/or the prongs 120, 121 can splay apart from each other as shown by the inflated profile outline shown in FIG. 40. Such inflation can advantageously allow the prongs 120, 121 to engage the user's nares more securely and improve the seal with the user's nares. In some embodiments, the seal 500 can increase in height by 2 mm or more when inflated. In some embodiments, the prongs 120, 121 can splay apart from each other by 2 mm or more when the seal 500 is inflated.

In some embodiments, a thickness of the bellows structure 522 is consistent or constant throughout the bellows structure 522. The thickness of the bellows structure 522 can be 0.75 mm. In some embodiments a thickness of the lower bellows portion 520 is consistent or constant throughout the lower bellows portion 520. A constant thickness can advantageously provide unbiased compression over the entirety of the bellows structure 522 and/or lower bellows portion 520. In such an embodiment, the cross-sectional profile of the seal 500 would therefore have a more significant impact on how compression of the seal 500 occurs than the thickness of the seal 500.

Figure 41:
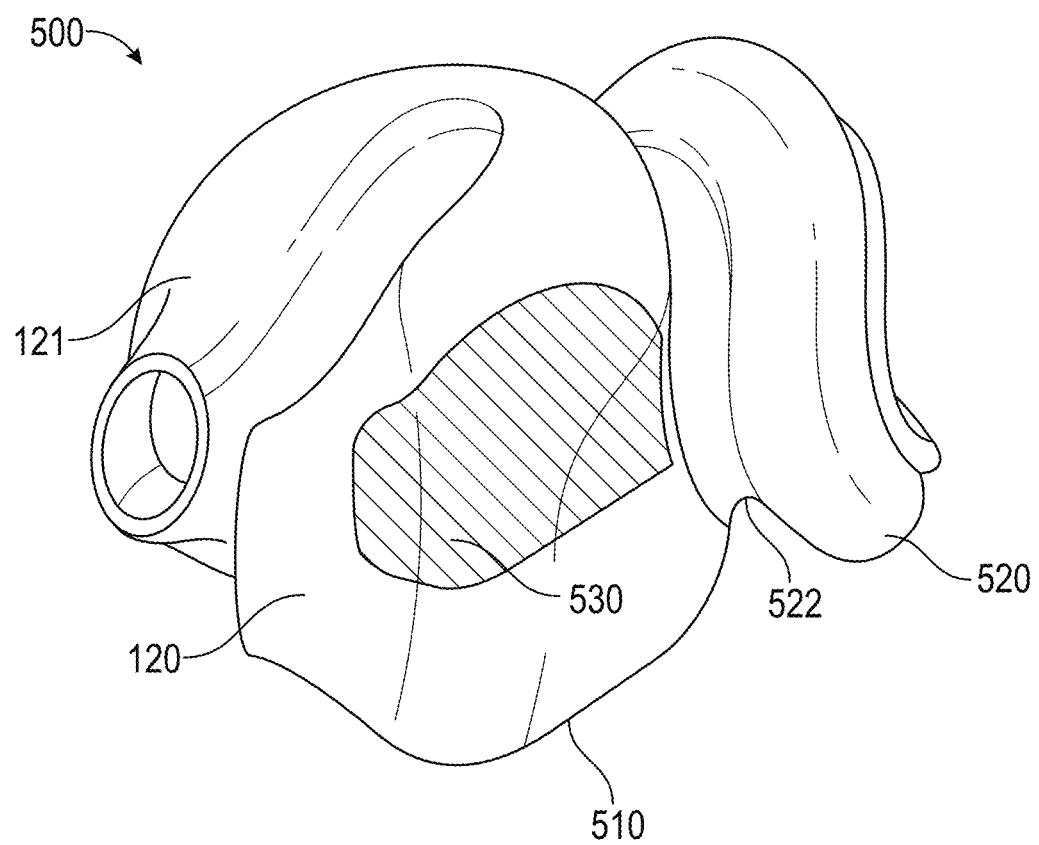
FIG. 41 is a perspective view of an embodiment of the seal of FIG. 32 including a thickened region.

In some embodiments, the seal 500 includes a thickened region 530 as shown in FIG. 41 that has a greater cross-sectional thickness than a remainder of the seal 500. In the illustrated embodiment, the thickened region 530 extends along lateral front portions of the seal 500. The thickened region 530 can help prevent or inhibit the sealing surface 512 from collapsing in the thickened region 530. In some embodiments, the thickened region 530 has a thickness of 1 mm and a remainder of the seal 500 has a thickness of 0.75 mm or similar relative thicknesses. FIG. 61C illustrates another embodiment of a seal with a thickened region 730 extending across the front of the prongs 120, 121 or sealing surfaces. This thickened region can help prevent or inhibit the prongs 120, 121 from collapsing in use.

Alternatively, the bellows section may have a varying thickness. The base section of the bellows may be thickest and the portion of the bellows at the top, i.e., closest to the prong or pillow is thinnest, or vice-versa. The thin portion of the bellow allows for greater flexing/pivoting. The thicker base allows for greater stability at the base.

In a further alternative, the bellow may be thick at the base and at the top and thin in the middle. The middle being thinner than the top and the bottom of the bellow. This allows for greater flexibility and flexure in the middle section of the bellow, while the thicker section provide for greater support at the top and bottom of the seal, allowing the prong to maintain its shape and also maintain orientation.

Figure 42A:
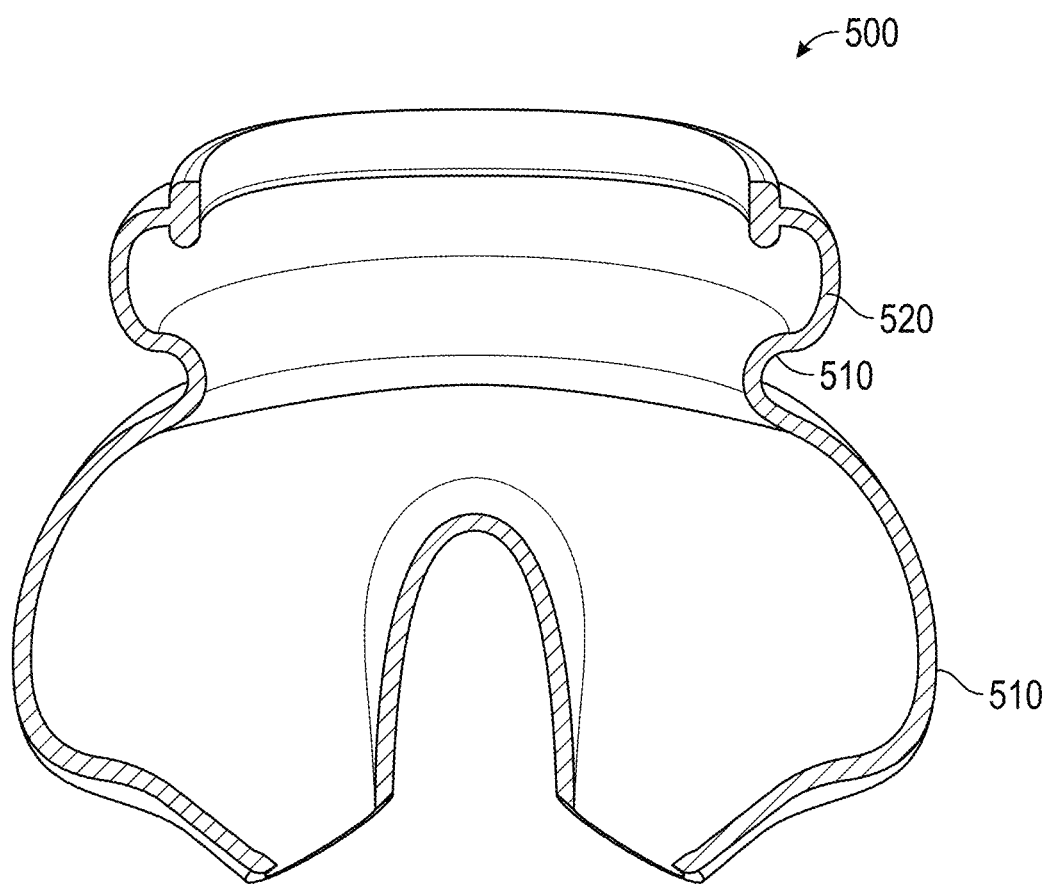
FIG. 42A is a sectional view of the seal of FIG. 32.
Figure 42B:
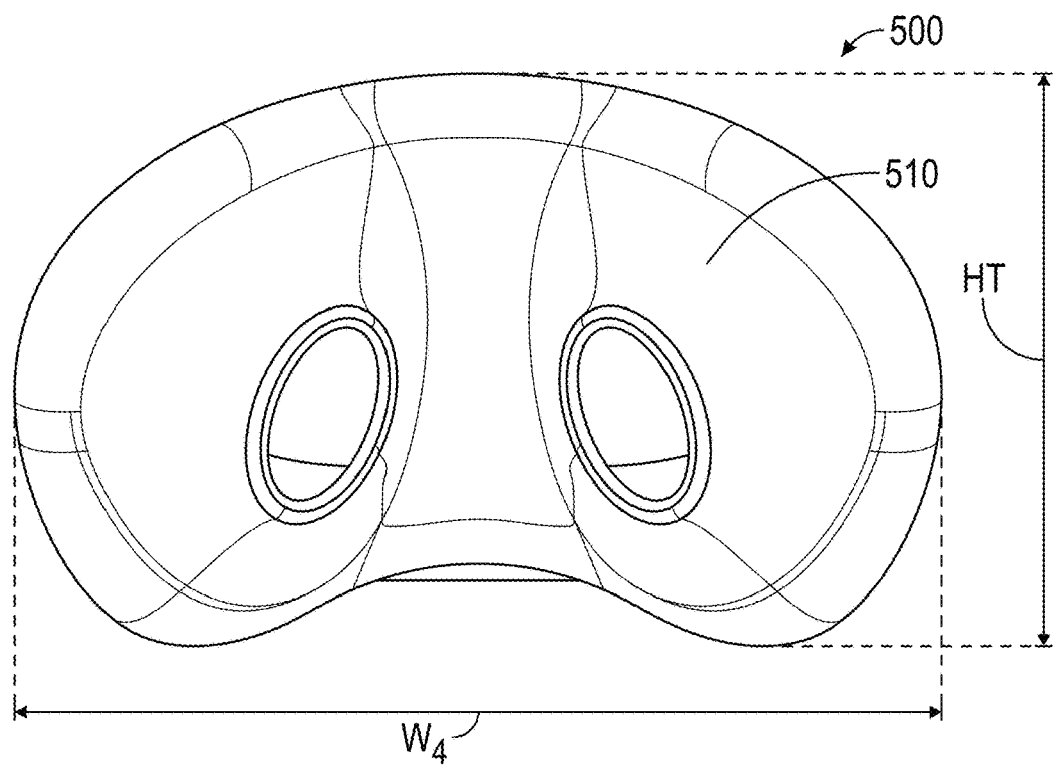
FIG. 42B is a view of the seal of FIG. 32 as viewed along arrow A of FIG. 2.
Figure 42C:
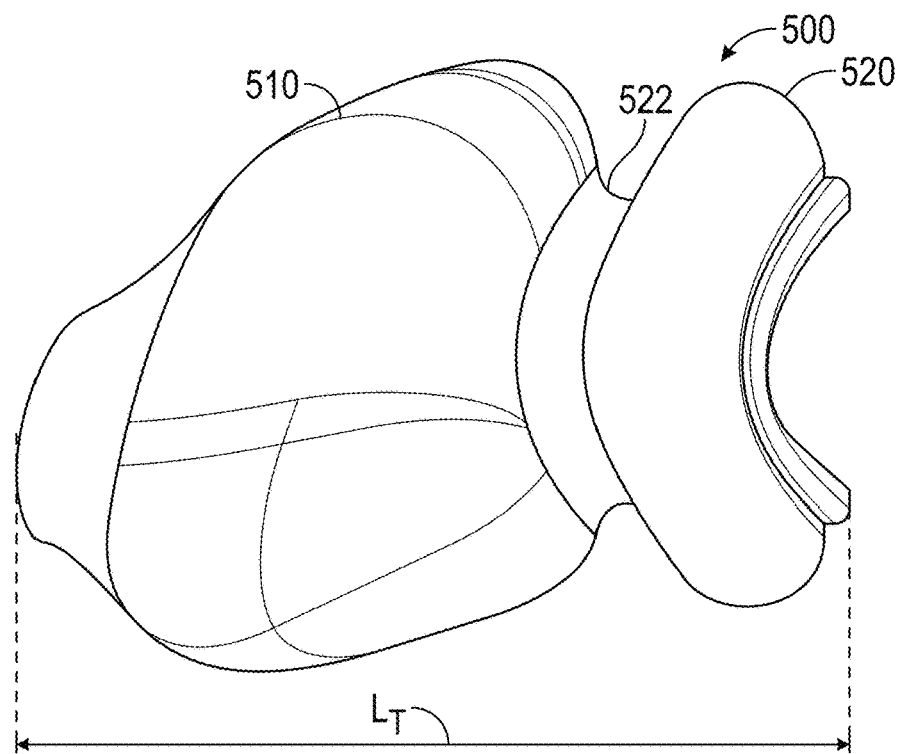
FIG. 42C is a side elevational view of the seal of FIG. 32.
Figure 42D:
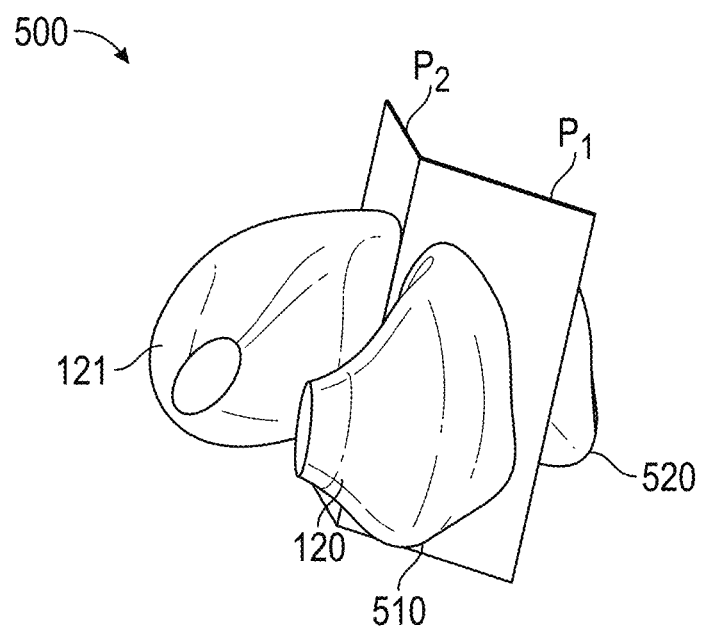
FIGS. 42D, 42E and 42F show various views of the seal of FIG. 32 showing interior volumes of various regions of the seal.
Figure 42E:
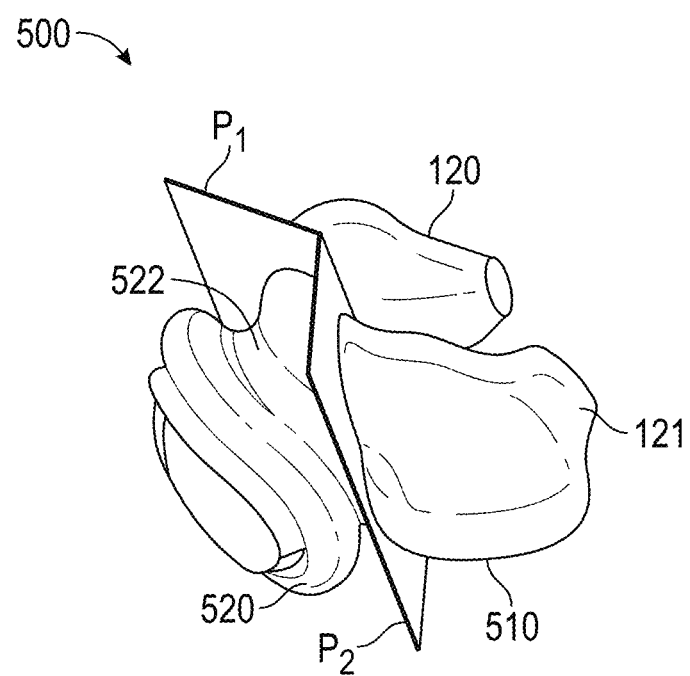
Figure 42F:
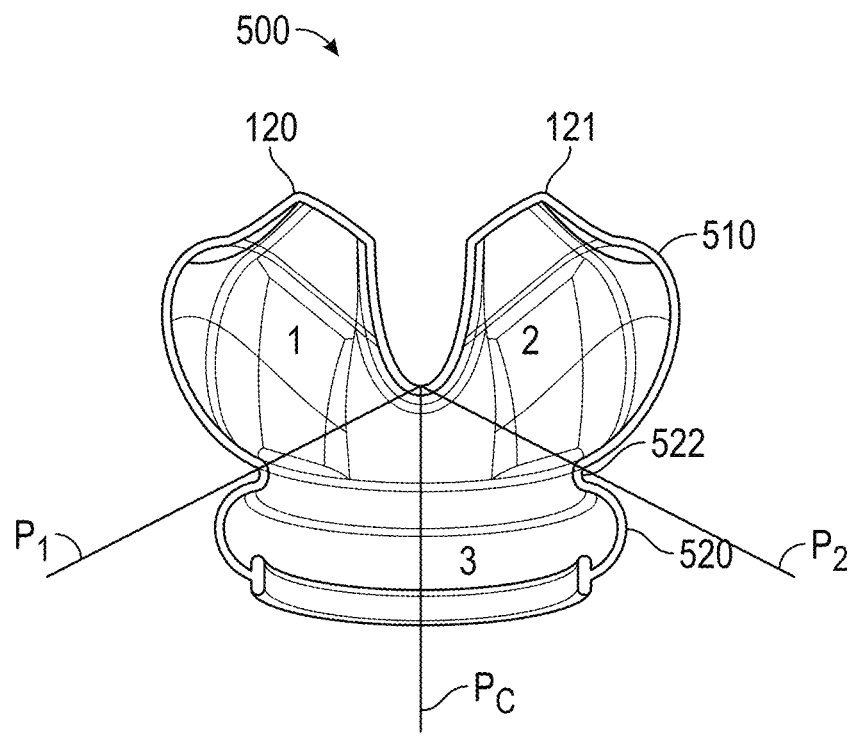
Figure 42G:
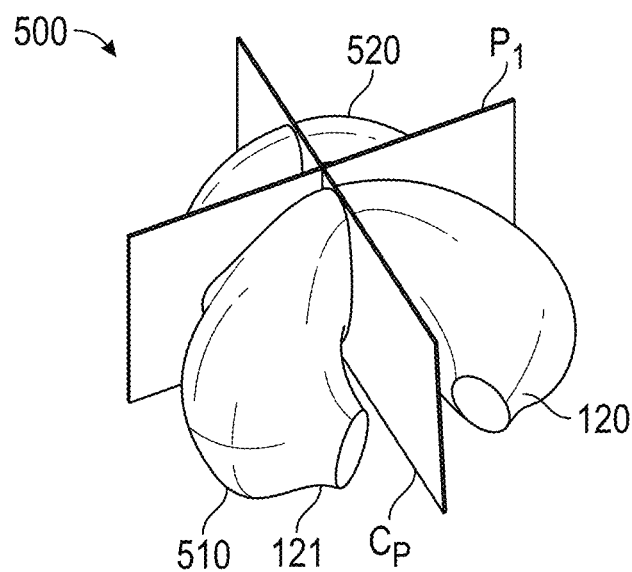
FIGS. 42G, 42H and 42I show various views of the seal of FIG. 32 showing interior volumes of various regions of the seal.
Figure 42H:
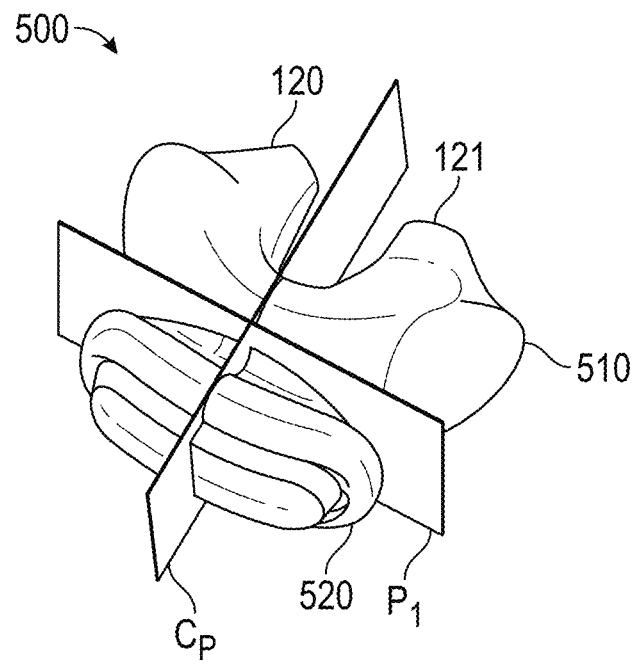
Figure 42I:
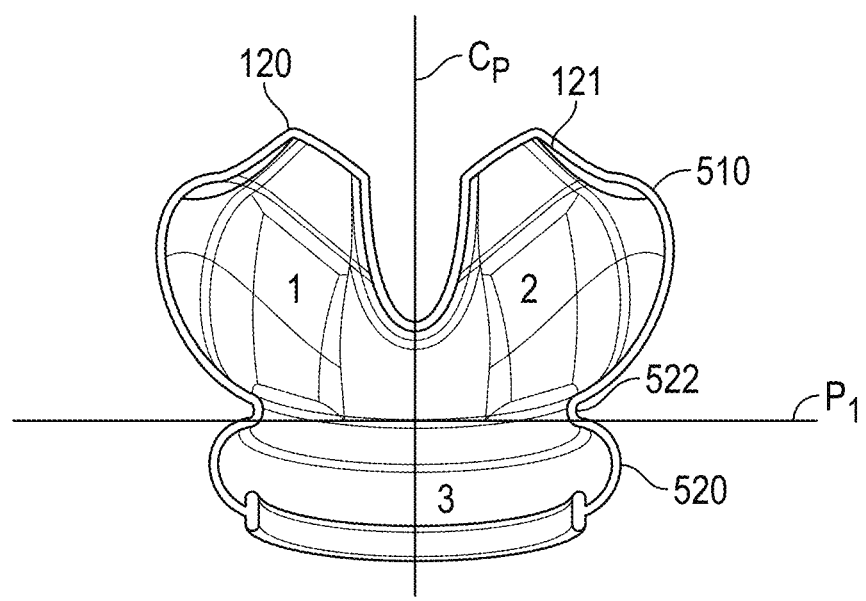

In some embodiments, an inner volume of the lower bellows portion 520, indicated by area 3 in FIG. 42I, is about 3966 mm3. In some embodiments, an inner volume of sealing portion 510 is about 11,158 mm3. An inner volume of each half of the sealing portion 510 (indicated by areas 1 and 2 in FIG. 42I where the sealing portion 510 is separated by a plane extending between the prongs 120, 121) can be 5579 mm3. Thus, the areas 1 and 2 can be collectively greater than the volume 3. In some configurations, each of the volumes 1 and 2 can be greater than the volume 3.

FIGS. 55A-55C illustrate another example embodiment of a seal 700 including a sealing portion 710, a lower bellows portion 720, a bellows structure or interface region 722, and the inlet orifice 130. The sealing portion 710 includes nostril prongs 120, 121, seal prong base 709, and sealing surfaces 712 that form seals with the nostrils of a user during use, which may be similar to other embodiments shown and described herein. The seal 700 can also have an apex A at a distal end (or end away from the patient) and a prong valley PV between the prongs 120, 121. In some embodiments, the prong 120, 121 apertures 118, 119 are elliptical as shown. Upper ends of the prongs 120, 121 and apertures 118, 119 can be angled inward such that the prong 120, 121 apertures 118, 119 form an inverted V shape when viewed from the front (or viewed from the perspective of the patient). The prongs 120, 121 can be sized and/or angled to advantageously reduce pressure on the patient's septum in use.

The lower bellows portion 720 supports the sealing portion 710. The inlet orifice 130 can have an oval or generally oval shape. In some embodiments, the inlet orifice 130 includes a rigid oval ring that acts as a connector for e.g., a frame or conduit. The bellows structure 722 can act as a compliant spring and/or resilient portion between the inlet orifice 130 and the prongs 120, 121. In some embodiments, the bellows structure 722 has a progressive spring rate as it compresses. During compression, support paddles on a frame coupled to the inlet orifice 130 can support lower corners 723 (shown in FIG. 55C) of the lower bellows portion 720.

Figure 55D:
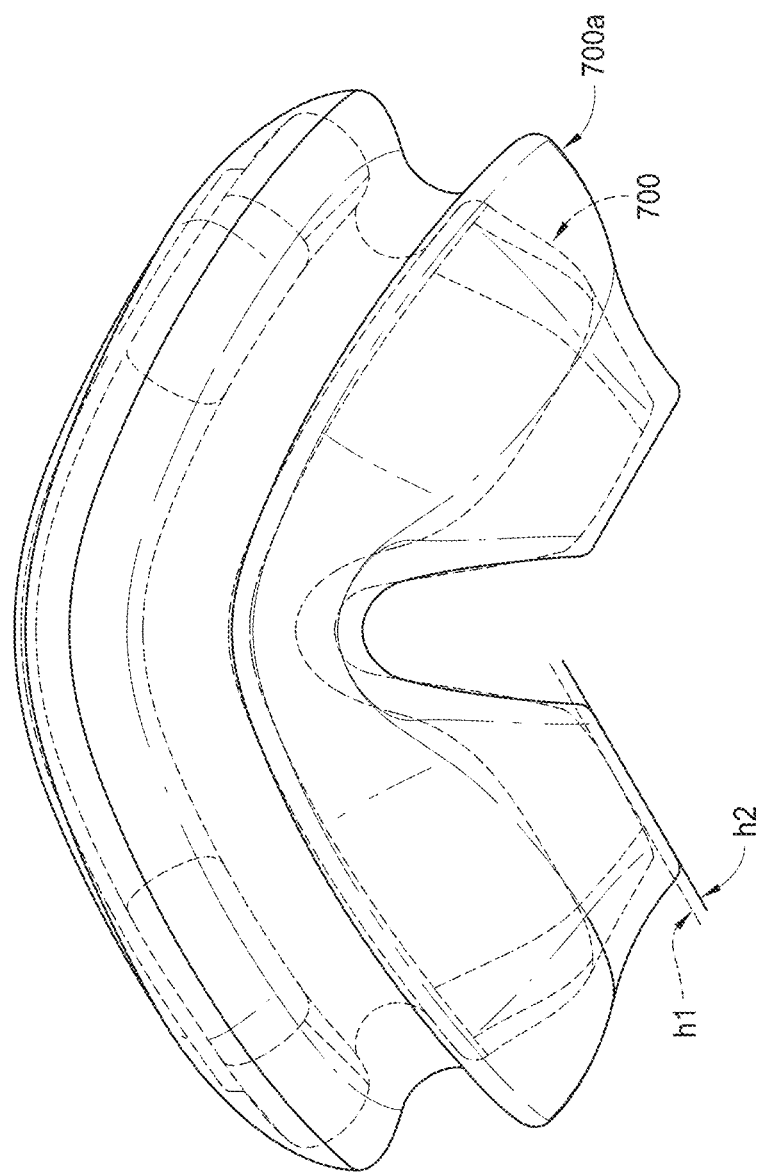
FIG. 55D is a top view of a large sized version of the seal superimposed over a medium sized version of the seal of FIG. 55A.
Figure 55E:
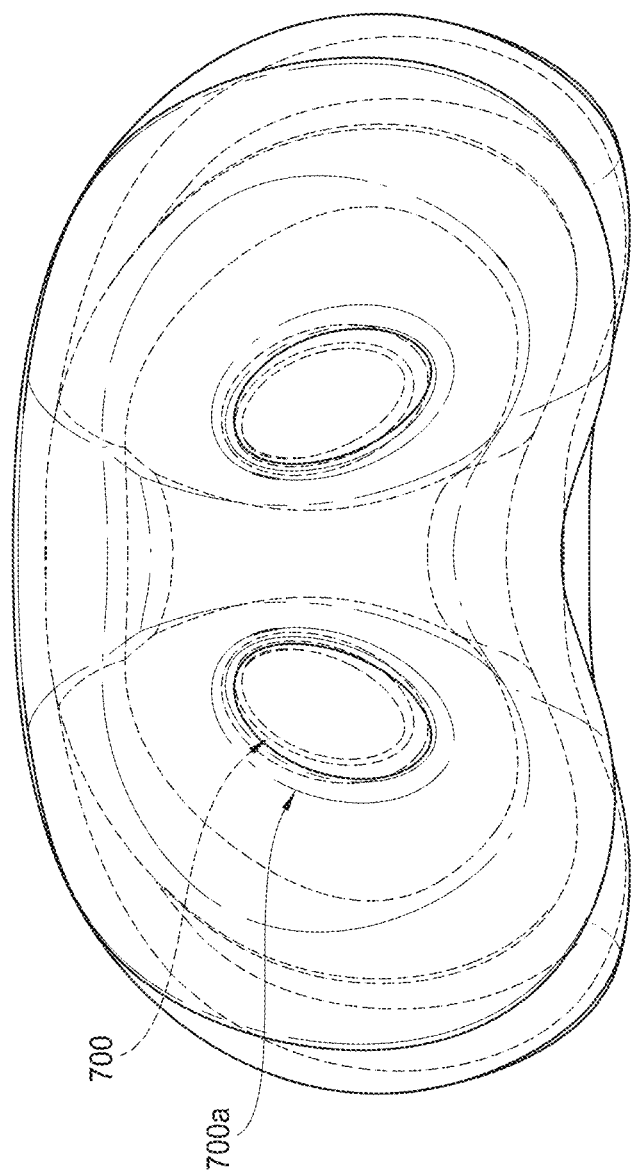
FIG. 55E is a front view of the seal of FIG. 55D.
Figure 62A:
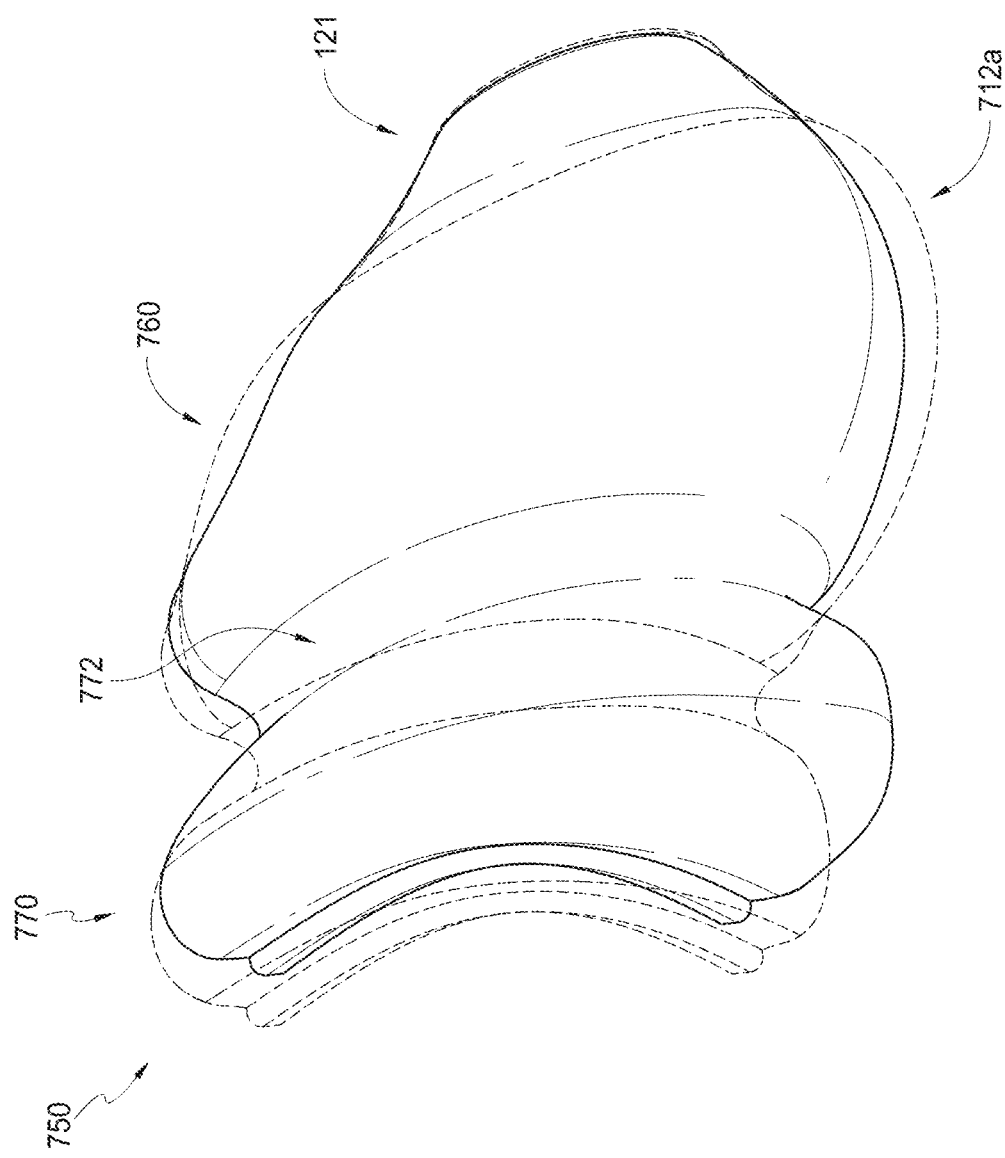
FIG. 62A is a side view of another example embodiment of a seal including a bellows.
Figure 62B:
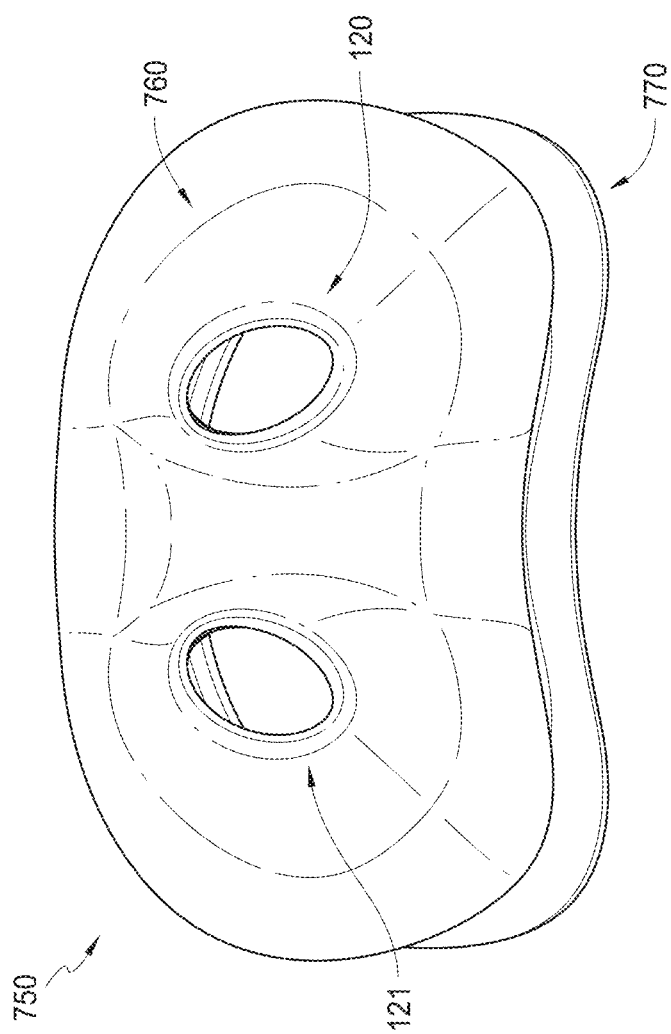
FIG. 62B is a front view of the seal of FIG. 62A.

In some embodiments, for example as shown in FIG. 55B, a lower central portion 711a of the sealing surfaces 712 and/or seal prong base 709 is raised (e.g., relative to lower lateral portions 711b and/or compared to, for example, the seal of FIGS. 62A-62B) to reduce, minimize, or eliminate contact with a central area of the patient's upper lip in use. A radius of curvature of the raised lower central portion 711a (shown as R1 in FIG. 55S) can be about 8.5 mm. A vertical displacement of the raised lower central portion 711a relative to a lowest point of the seal (shown as X2 in FIG. 55T) can be about 5.7 mm. In some embodiments, the lower lateral portions 711b can contact the patient's face, specifically, lateral portions of the patient's upper lip, in use. Such a configuration can advantageously increase patient comfort as the central area of the upper lip is often more sensitive than lateral portions of the upper lip. In some embodiments, a lower central portion 711c of the lower bellows portion 720 can also or alternatively be raised to reduce, minimize, or eliminate contact with the central area of the patient's upper lip in use. A radius of curvature of the raised lower central portion 711c (shown as R2 in FIG. 55S) can be about 22.0 mm. A vertical displacement of the raised lower central portion 711c relative to the lowest point of the seal (shown as X1 in FIG. 55T) can be about 3.9 mm. In some embodiments, lower lateral portions 711 of the lower bellows portion 720 can contact the patient's face, specifically, lateral portions of the patient's upper lip, in use. During hose tug, the lower lateral portions 711 of the lower bellows portion 720 can help provide stability by comfortably touching the patient's upper lip.

In some embodiments, for example as shown in FIG. 55A and the cross-sectional view of FIG. 55O, a distal surface 709a of the seal prong base 709 (or surface facing away from the patient) is flat or generally flat. In contrast, the distal surface of the sealing portion or seal prong base of the seals of FIGS. 61A-61C and 62A-62B can be rounded or curved. Such a flattened surface at a boundary between the interface region 722 and the seal prong base 709 can advantageously provide a defined flex region between the lower bellows portion 720 and the sealing portion 710 and/or a more even contact surface for contact between the seal prong base 709 or sealing portion 710 and the lower bellows portion 720, which can advantageously increase stability of the seal 700.

As shown in FIG. 55A, lateral sides of the lower bellows portion 720 can curve toward the sealing portion 710 such that the lower bellows portion 720 and/or bellows structure 722 is generally U-shaped or V-shaped. In the illustrated embodiment, a curvature of the lower bellows portion 720 matches or corresponds to (or substantially or generally matches or corresponds to) a curvature of the lower surfaces of the sealing portion 710. In other words, the lower bellows portion 720 of the seal 700 of FIGS. 55A-55C can be generally bean shaped rather than, for example, generally oval-shaped (like the lower bellows portion of the seal of, e.g., FIGS. 61A-61C). In such embodiments, a distance between the lower bellows portion 720 and the lower surfaces of the sealing portion 710 is substantially the same or equal around an entire circumference of the seal 700. The bellows structure 722 can have a consistent cross-section around the entire circumference of the seal. A constant distance between the lower bellows portion 720 and lower surfaces of the sealing portion 710 or constant bellows structure 722 cross-section around the circumference of the seal 700 can advantageously allow for a more even compression of the seal 700 around the entire lower bellows portion 720. In other words, the seal 700 is less likely to bottom out in one area of the seal 700 before a remainder of the circumference of the seal 700. In some embodiments, a U-shaped lower bellows portion 720 can advantageously reduce load on the underside of the patient's nose when the headgear is engaged to the patient's face to secure the seal 700 to the patient's face. The shape of the lower bellows portion 720 and/or bellows structure 722 can reduce an overall height of the seal 700, which can help minimize the effect of hose tug.

Figure 55H:
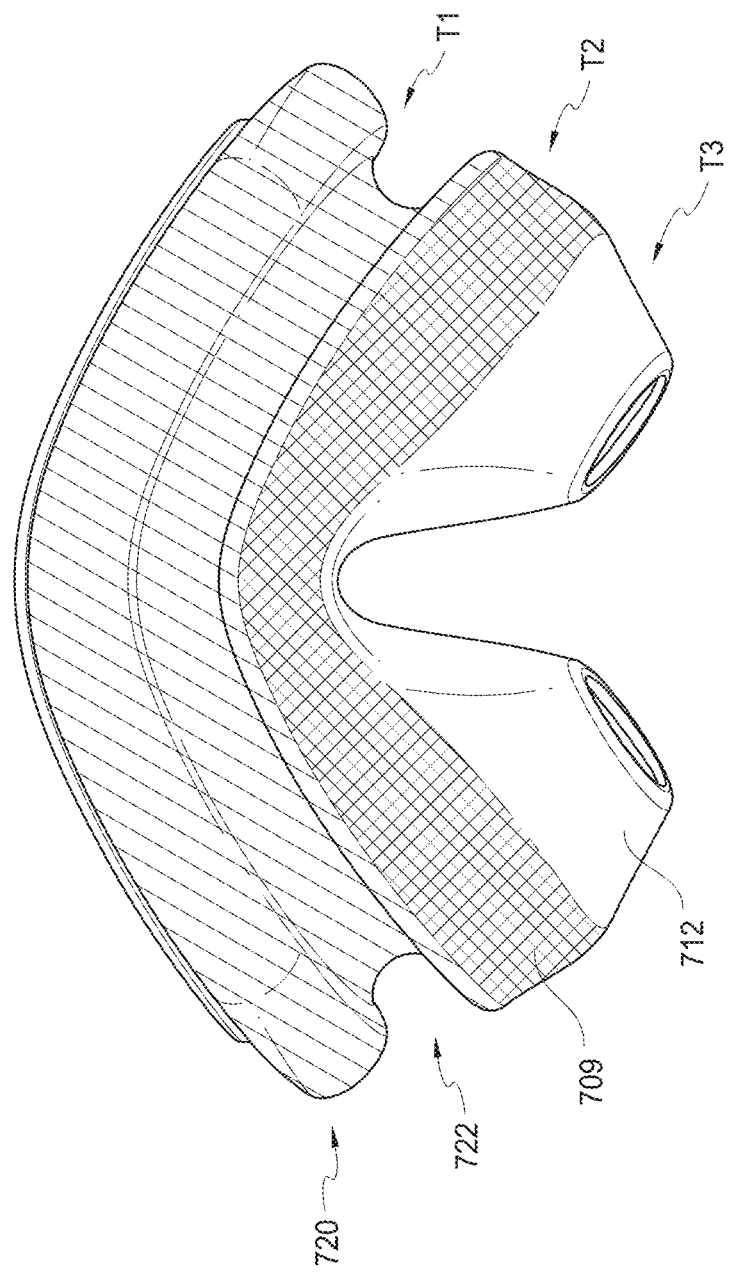
FIG. 55H is a top view of the seal of FIG. 55A showing various thickness regions.

In some embodiments, the seal 700 includes a thickened region. In some such embodiments, the thickened region extends along a front of the sealing surface 712 and/or prongs 120, 121, for example like thickened region 730 shown in FIG. 61C. The thickened region can help prevent or inhibit the sealing surface 712 from collapsing in the thickened region. In some embodiments, the thickened region is 1.0 mm thick and the remainder of the seal is 0.8 mm thick. In some embodiments, the seal 700 can have various thickness regions, as shown in FIG. 55H. In some embodiments, a first region T1 of the seal 700 that includes the lower bellows portion 720 and bellows structure or interface region 722 has a thickness in the range of about 0.7 mm to about 1.0 mm, for example, about 0.85 mm. A second region T2 that includes the seal prong base 709 can have a thickness in the range of about 0.9 mm to about 1.1 mm, for example, about 1.0 mm. A third region T3 that includes the sealing surfaces 712 can have a thickness in the range of about 0.7 mm to about 0.8 mm, for example about 0.75 mm. A thickness in this range can advantageously provide sufficient support to the sealing surfaces 712 and seal 700 to inhibit collapse without being too rigid. The second region T2 including the seal prong base 709 can have a greater thickness than the third region T3 including the sealing surfaces 712 to help support the sealing surfaces 712 under the compression experienced during use. The sealing surfaces 712 can have a reduced thickness compared to the seal prong base 709 to provide improved patient comfort and/or seal performance. In some embodiments, the thicknesses and/or profiles of the various regions of the seal 700 can be selected such that the lower bellows portion 720 and/or interface region 722 compress before the sealing surfaces 712 in use. This can help improve seal performance, increase seal 700 stability, and/or improve patient comfort. If the thickness of various region(s) of the seal 700 is altered, changes to the profile, e.g., length, of the seal 700 may be needed to maintain the same or approximately the same spring constant. For example, if the thickness of the first region T1 is increased from 0.85 mm to 1.0 mm, a length of the interface region 722 (which corresponds to the amount of displacement possible between the lower bellows portion 720 and seal prong base 709) preferably is increased to maintain the desired compression profile. The lower bellows portion 720 and/or interface region 722 can have a constant thickness. A constant thickness can help promote uniform compression along a lateral length of the interface region 722.

Figure 55M:
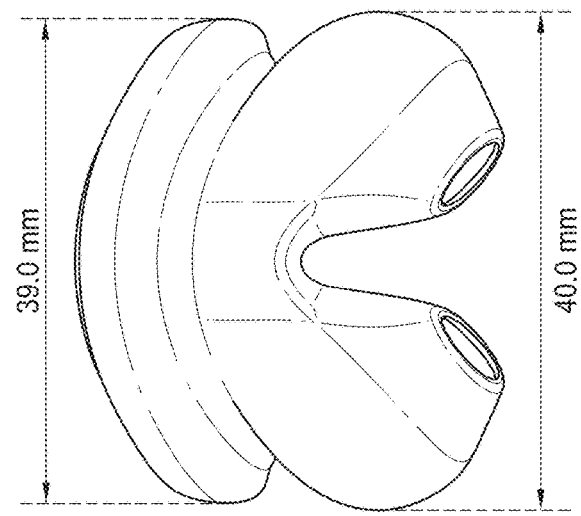
FIG. 55M is a top view of the seal of FIG. 62A.
Figure 55L:
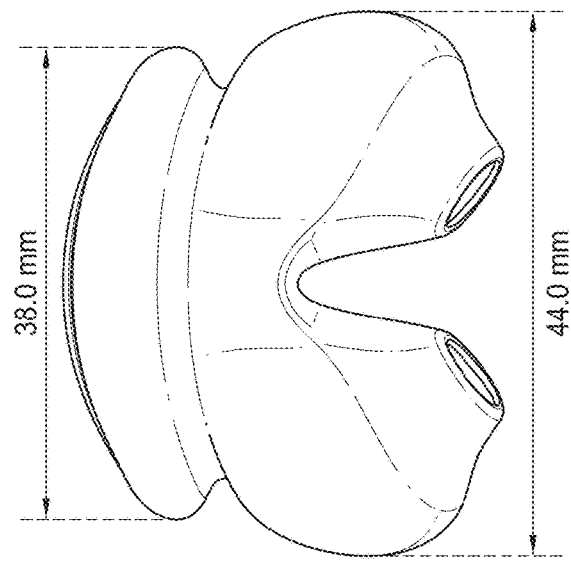
FIG. 55L is a top view of the seal of FIG. 61A.
Figure 55N:
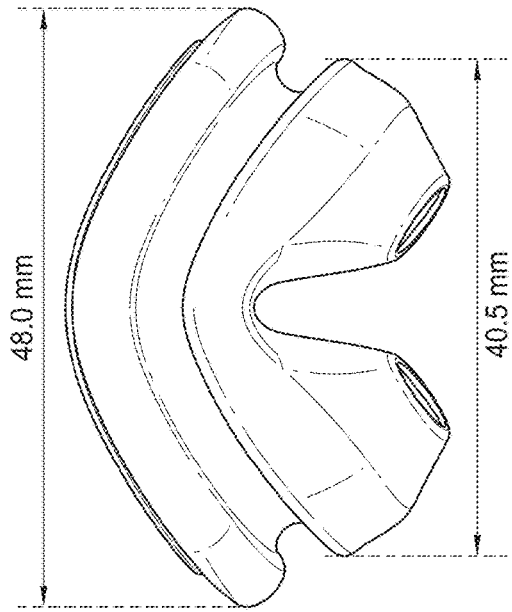
FIG. 55N is a top view of the seal of FIG. 55A.
Figure 550:
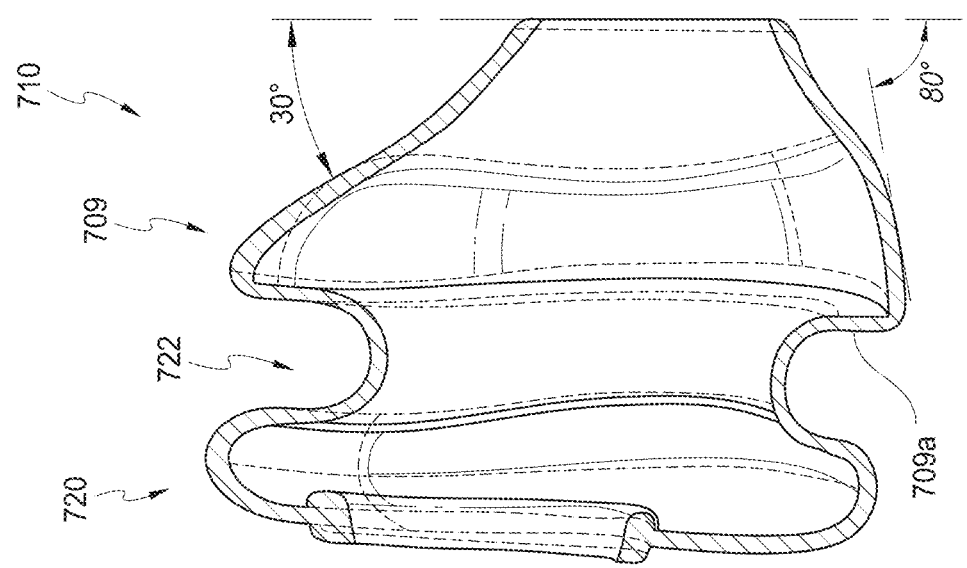

In the illustrated embodiment, the outer perimeter of the lower bellows portion 720 is larger and/or wider than the perimeter of the sealing portion 710. A larger lower bellows portion 720 can advantageously provide increased stability to the seal 700. A larger lower bellows portion 720 can allow the sealing portion 710 or sealing surfaces 712 and bellows structure 722 to compress and form a seat against the larger bellows portion 720. A larger lower bellows portion 720 can help prevent or inhibit splaying of the prongs. FIG. 55N illustrates a top view of the seal of FIG. 55A showing example dimensions of the lower bellows portion 720 and seal prong base 709. As shown, in the illustrated embodiment, a maximum lateral width of the sealing portion 710 can be about 40.5 mm and a maximum lateral width of the lower bellows portion 720 can be about 48.0 mm. In some embodiments, a ratio of the maximum lateral width of the lower bellows portion 720 to the maximum lateral width of the sealing portion 710 is about 5:4. For comparison, FIGS. 55L and 55M illustrate top views of the seals of FIGS. 61A-61C and FIGS. 62A-62B (described in greater detail below), respectively. As shown, the seal of FIG. 55L can have a maximum lateral width of the sealing portion of about 44.0 mm and a maximum lateral width of the lower bellows portion of about 38.0 mm. The seal of FIG. 55M can have a maximum lateral width of the sealing portion of about 40.0 mm and a maximum lateral width of the lower bellows portion of about 39.0 mm. In some situations in which the lateral width of the sealing portion is greater than the lateral width of the lower bellow portion, for example in the seals of FIGS. 55L and 55M, during compression the seal portion can deform around the outside or periphery of lower bellows portion, which can reduce the effectiveness of the seal. Widening the lower bellows portion such that the lower bellows portion is almost as wide as or wider than the sealing portion can prevent, inhibit, or reduce the likelihood of the sealing portion deforming around the edges of the lower bellows portion to help maintain a more effective seal under compression. In some configurations, a width of the lower bellows portion is at least about 90%, 95% or 97.5% of a width of the sealing portion.

In some embodiments, a width of the inlet orifice 130 is the same or about the same as a width of the sealing surface. A wider inlet orifice 130 and connection to the frame or conduit can provide for improved stability, for example, by allowing for less flexibility in the outward range. FIG. 55I illustrates a rear view of the seal 700 of FIG. 55A showing example dimensions of the inlet orifice 130 and overall seal 700. In the illustrated embodiment, a lateral width L1 of the inlet orifice 130 is about 43.0 mm and a total lateral width Lmax1 of the seal 700 is about 48.0 mm. For comparison, FIGS. 55J and 55K illustrate rear views of the seals of FIGS. 61A-61C and FIGS. 62A-62B (described in greater detail below), respectively. As shown, the seal of FIG. 55J can have an inlet orifice 130 lateral width L2 of about 30.0 mm and a total lateral width Lmax2 of about 44.0 mm, and the seal of FIG. 55K can have an inlet orifice 130 lateral width L3 of about 30.0 mm and a total lateral width Lmax3 of about 40.0 mm. The seal 700 of FIGS. 55A-55C and 55I therefore has a greater inlet orifice 130 lateral width than the seals of FIGS. 55J and 55K. The seal 700 of FIGS. 55A-55C and 55I also has a greater total lateral width than the seals of FIGS. 55J and 55K. The ratio of the inlet orifice 130 lateral width to the total lateral width of the seal 700 of FIGS. 55A-55C and 55I is also greater than the ratios of the inlet orifice 130 lateral width to the total lateral width of the seals of FIGS. 55J and 55K. As explained above, a wider inlet orifice 130 and connection to the frame or conduit, and/or a greater ratio of the inlet orifice lateral width to the total lateral width, can advantageously improve the stability of the seal, for example, by allowing for less flexibility in the outward range.

The seal 700 can be made in different sizes and/or shapes to accommodate different sizes and shapes of user's faces. For example, the elliptical apertures 118, 119 can be 10.5 mm long and 6.5 mm wide for a "standard" or "medium" size (e.g., as shown in FIGS. 55A-55C), 12.0 mm long and 7.9 mm wide for a "large" size (e.g., as shown in FIGS. 55D-55E) designed to accommodate users having relatively wide and/or round nostrils, or 8.5 mm long and 5.6 mm wide for a "small" size (e.g., as shown in FIGS. 55F-55G). The prongs 120, 121 and apertures 118, 119 can be sized and/or shaped to advantageously reduce pressure on the patient's septum in use.

Figure 55Q:
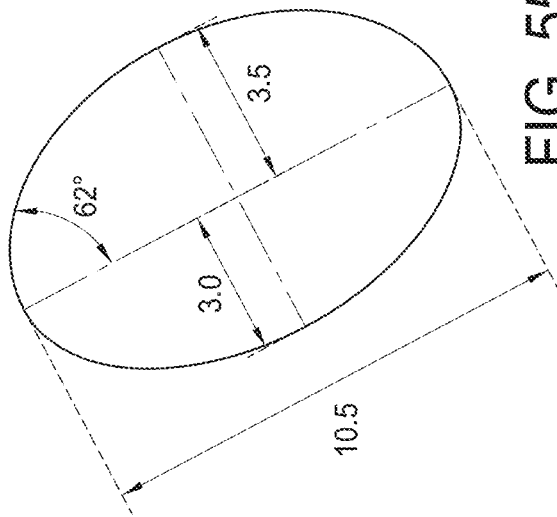
FIG. 55Q shows example dimensions of the prong apertures of the seal of FIG. 55A.

In some embodiments, the apertures 118, 119 are asymmetrical. In some such embodiments, a length of the minor axis (along the width of the aperture 118, 119) of a lateral half-oval portion of the aperture 118, 119 is greater than a length of the minor axis of a medial half-oval portion of the aperture 118, 119, for example, as shown in FIG. 55Q, which illustrates example dimensions for the apertures 118, 119 of a "standard" or "medium" size seal 700. In a "small" seal, the length of the minor axis of the lateral half-oval portion of the aperture 118, 119 can be 3.00 mm (compared to 3.5 mm for the "medium" size), and the length of the minor axis of the medial half-oval portion can be 2.6 mm (compared to 3.0 mm for the "medium"). In a "large" seal, the length of the minor axis of the lateral half-oval portion of the aperture 118, 119 can be 4.20 mm, and the length of the minor axis of the medial half-oval portion can be 3.70 mm. The ratio of the longer of the minor axes (the minor axis of the lateral half-oval portions in the illustrated embodiments) to the smaller of the minor axes (the minor axis of the medial half-oval portions in the illustrated embodiments) in any or all of the medium, small, and large seals can be in the range of 1:1 to 5:4, for example, about 1.15. A ratio in this range can advantageously inhibit or reduce the likelihood of localized collapse of surrounding wall sections of the seal. A ratio of the major axis to the overall minor axis of any or all of the medium, large, and small size seals can be about 1.5.

As shown in FIGS. 55D-55E, a height h2 of a "large" seal 700a can be increased relative to a height h1 of a "medium" seal 700. In some embodiments, h2 can be 1.5 mm greater than h1. The increased height can help maintain an outer nostril support angle (shown in FIG. 55F with respect to a "small" seal) of the prongs 120, 121, for example, of 120°. A minimum distance between the prongs 120, 121 can be the same or approximately the same in the large seal 700a as the medium seal 700 because septum measurements or thicknesses can be fairly consistent among patients having different nostril widths. As shown in FIGS. 55F-55G, a height h3 of a "small" seal 700b can be decreased relative to the height h1 of the "medium" seal 700. The decreased height can help maintain an outer nostril support angle, indicated by SA in FIG. 55F, of the prongs 120, 121. In the illustrated embodiment, the support angle SA is 120°. A minimum distance between the prongs 120, 121 can be the same or approximately the same in the small seal 700b as the medium seal 700 because septum measurements or thicknesses can be fairly consistent among patients having different nostril widths. In some embodiments, the distance between the ends (which include the apertures 118, 119) of the prongs 120, 121 is about 7.2 mm. This distance can be maintained or the same (or substantially the same) in all three sizes. In some embodiments, the ends of the prongs 120, 121, i.e., the apertures 118, 119, are oriented at an angle, indicated as PA in FIG. 55A, relative to a vertical axis of 120°. This angle can be maintained or the same (or substantially the same) in all three sizes.

Figure 55P:
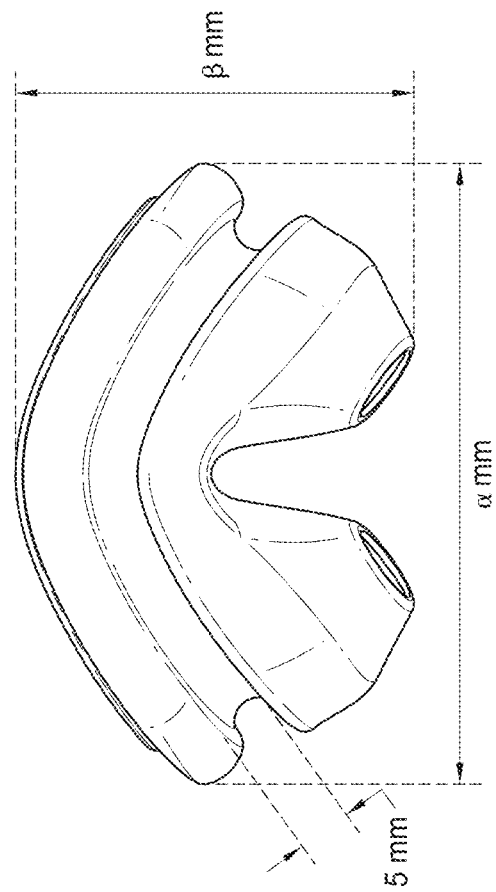
FIG. 55P is a top view of the seal of FIG. 55A showing certain dimensions of the seal.
Figure 55R:
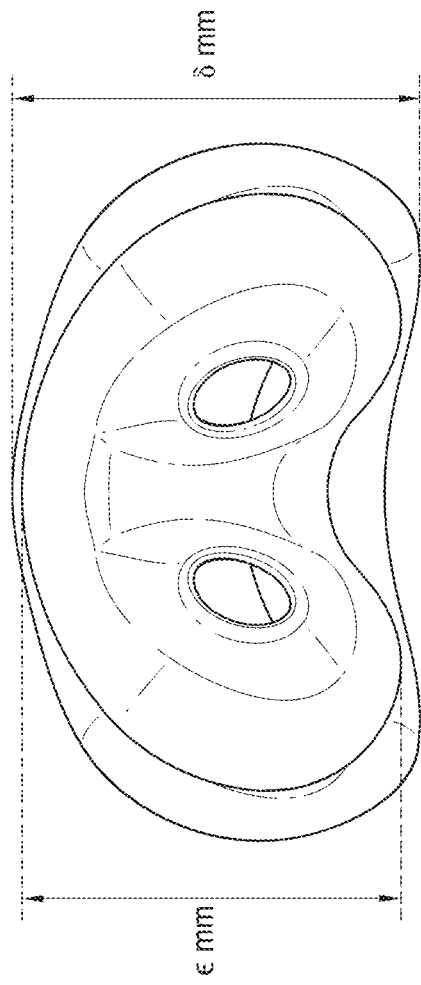
FIG. 55R is a front view of the seal of FIG. 55A showing certain dimensions of the seal.
Figure 55S:
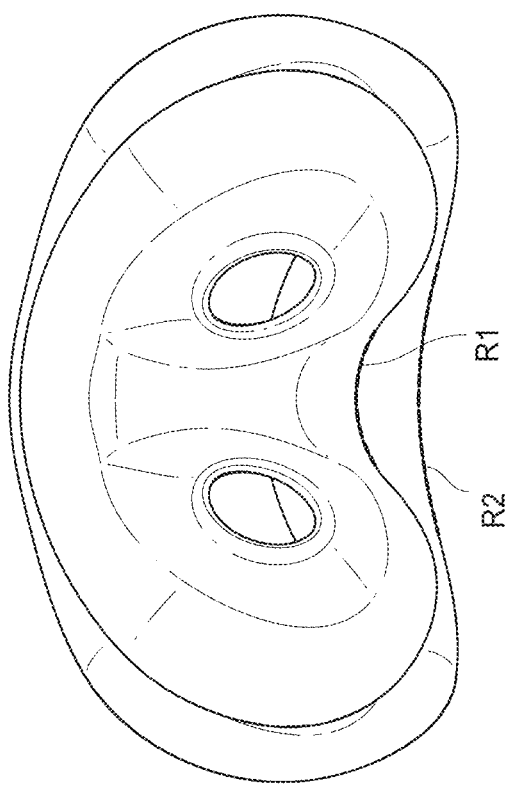
FIG. 55S is a front view of the seal of FIG. 55A showing the radii of curvature of lower central portions of the seal.
Figure 55T:
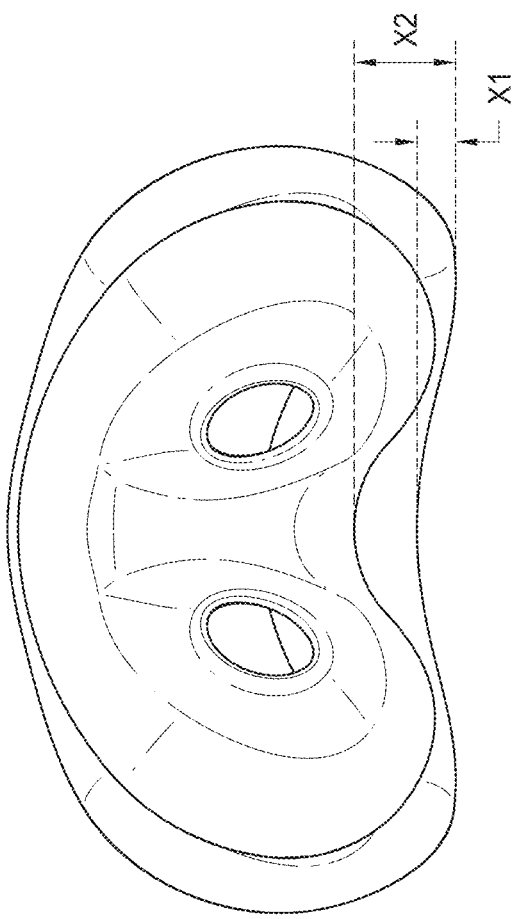
FIG. 55T is a front view of the seal of FIG. 55A showing the vertical offset of the lower central portions of the seal.

FIGS. 55P and 55R identify certain dimensions of the seal 700. Example values for those dimensions are shown in the table below. In some embodiments, a distance of the interface region 722, or distance between the distal surface 709a of the seal prong base 709 (or surface facing away from the patient) and the lower bellows portion is about 5 mm as indicated in FIG. 55P. This distance of the interface region 722 can be reduced compared to the seals of FIGS. 61A-61C and 62A-62B (discussed in greater detail below). The reduced interface region 722 distance can advantageously reduce the possible travel length of the seal 700, which can improve seal stability.

|   | Small | Medium | Large |
|---|---|---|---|
| α | 48.0 mm | 48.0 mm | 50.6 mm |
| β | 27.0 mm | 29.5 mm | 31.0 mm |
| δ | 28.0 mm | 28.5 mm | 29.5 mm |
| ε | 24.8 mm | 26.0 mm | 28.6 mm |

In some embodiments, for example as shown in FIG. 55P, lateral edges of the sealing surfaces 712 of the prongs 120, 121 are straight or generally straight in the medium seal. In some embodiments, lateral edges of the sealing surfaces 712 of the prongs 120, 121 are curved in the large seal. In some such embodiments, when viewed from the top, the lateral edges initially form a concave shape with respect to the user extending from the aperture 118, 119. In some embodiments, the curvature of the lateral edges changes to a convex shape with respect to the user at an inflection region. The convex shape can continue to the distal surface 709a of the seal prong base 709. The inflection region can be located approximately ⅓ of the length of the lateral edge from the aperture 118, 119. In some embodiments, the lateral edges of the sealing surfaces 712 of the prongs 120, 121 of the medium seal can be curved similarly to those of the large seal or the lateral edges of the sealing surfaces 712 of the prongs 120, 121 of the large seal can be straight similar to those of the medium seal.

Figure 56B:
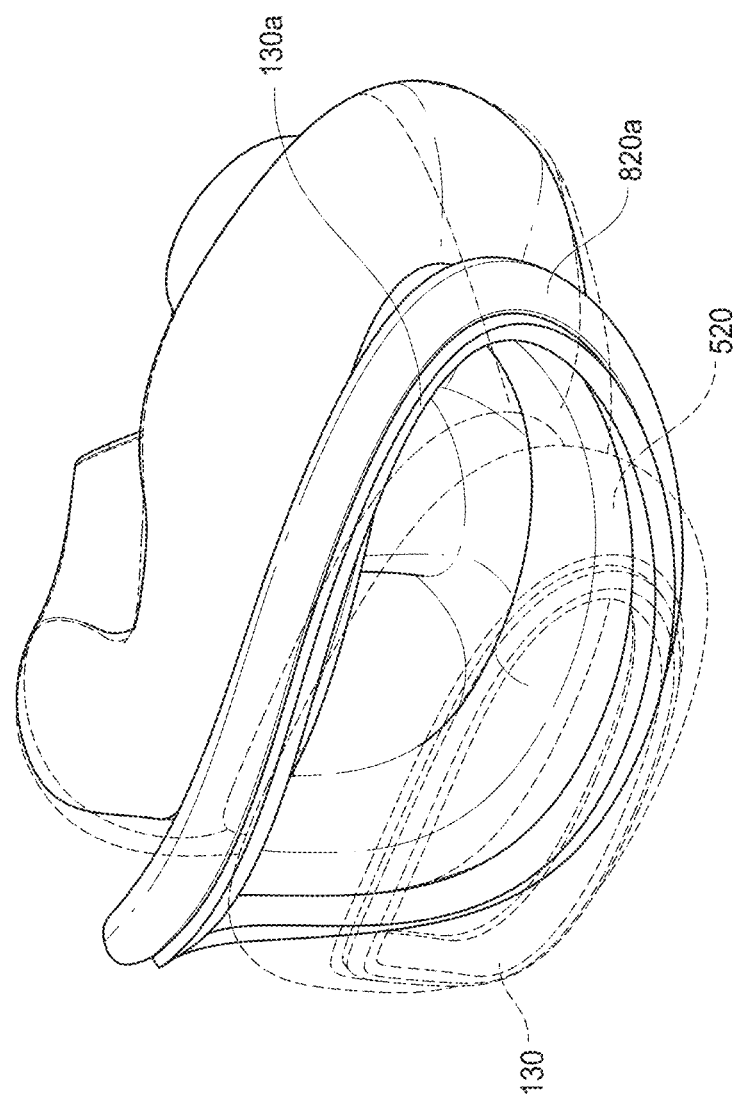
FIG. 56B is a rear perspective view of the seal of FIG. 56A.

FIGS. 56A-62B illustrate other example embodiments of seals including sealing portions with prongs 120, 121 and sealing surfaces and lower bellows portions with bellows structures and inlet orifices. In the embodiment of FIGS. 56A-56B, the lower bellows portion 820a and inlet orifice 130a are relatively wider and taller than the lower bellows portion 520 and inlet orifice 130 of the seal 500 of FIGS. 32-42I. The wider and taller lower bellows portion 820a can help support the lateral sides of the sealing portion 810a. The wider and taller inlet orifice 130a can allow for use of a shorter frame. The wider and taller inlet orifice 130a can allow placement of a vent arrangement (e.g., bias flow holes) on one or both lateral sides of a frame that supports the seal. In other words, the size (height and/or width) of the inlet orifice 130a allows the accommodation of both an inlet and an outlet (vent) within the area defined by the orifice 130a.

Figure 57A:
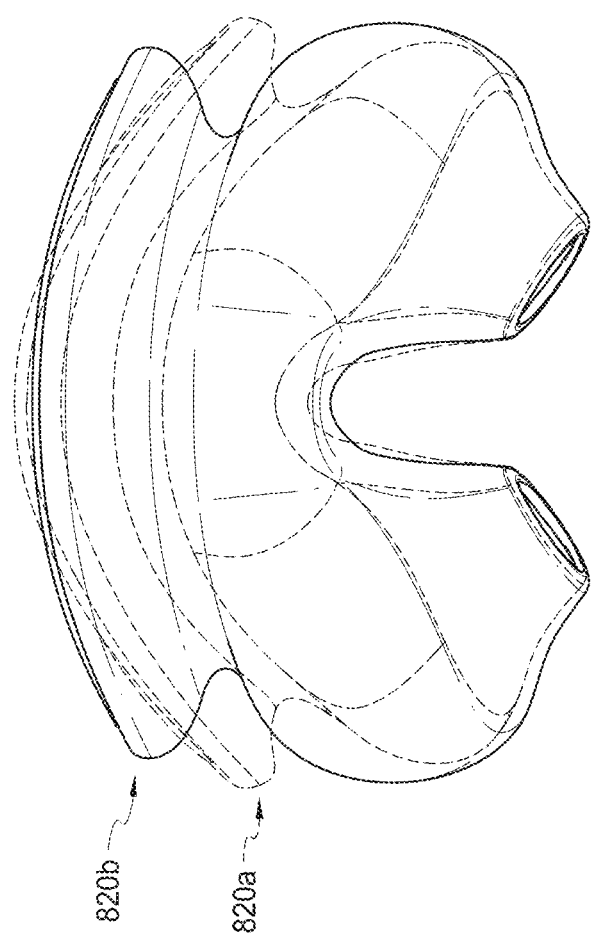
FIG. 57A is a top view of another example embodiment of a seal including a bellows.
Figure 57B:
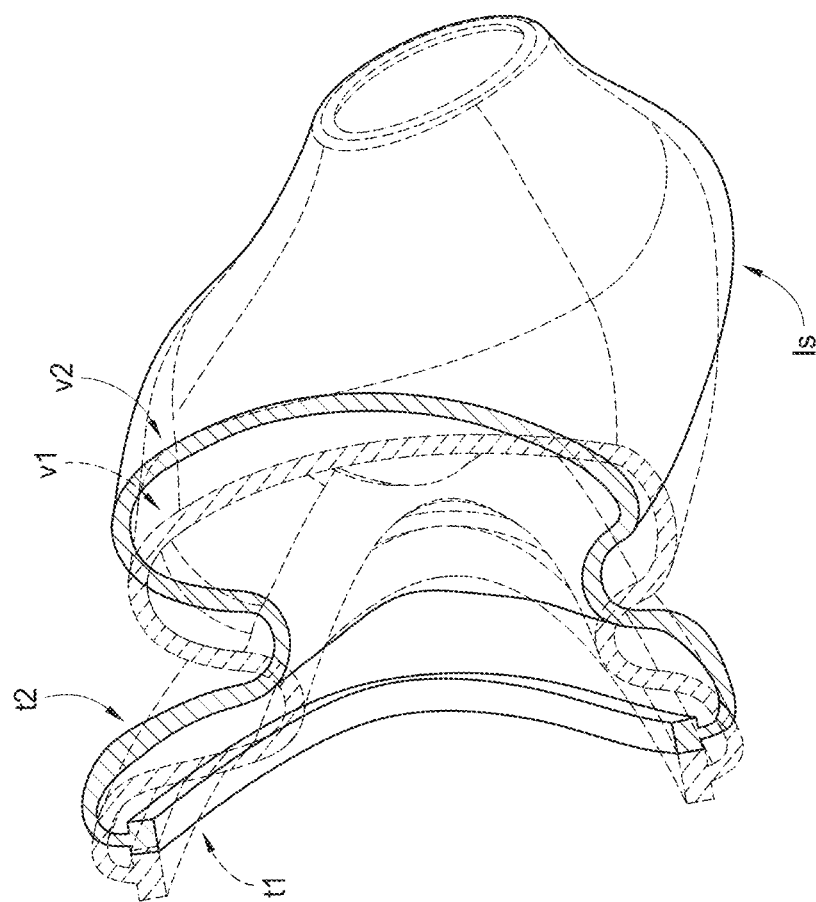
FIG. 57B is a side cross sectional view of the seal of FIG. 57A.

In the embodiment of FIGS. 57A-57B, the lower bellows portion 820b has a reduced curvature compared to the lower bellows portion 820a of the seal of FIGS. 56A-56B. The reduced curvature can allow the bellows structure to compress more evenly in use. As shown in FIG. 57B, a depth of the valley v2 between the prongs 120, 121 can be reduced compared to the depth of the valley v1 between the prongs 120, 121 in the embodiment of FIGS. 56A-56B. A reduced valley depth can allow for increased seal travel during compression. The lower bellows portion 820b can have an increased thickness t2 in the area of the tip of the patient's nose in use compared to the thickness t1 of the seal of FIGS. 56A-56B. The increased thickness in this region can help compensate for a reduction in stiffness of the seal that may otherwise result from the seal's shape. A lower surface is of the sealing surface 812 can be enlarged, for example, by 1.5 mm. An enlarged lower surface can help reduce leaks, for example, when the seal is used on patients having relatively flatter noses.

Figure 58:
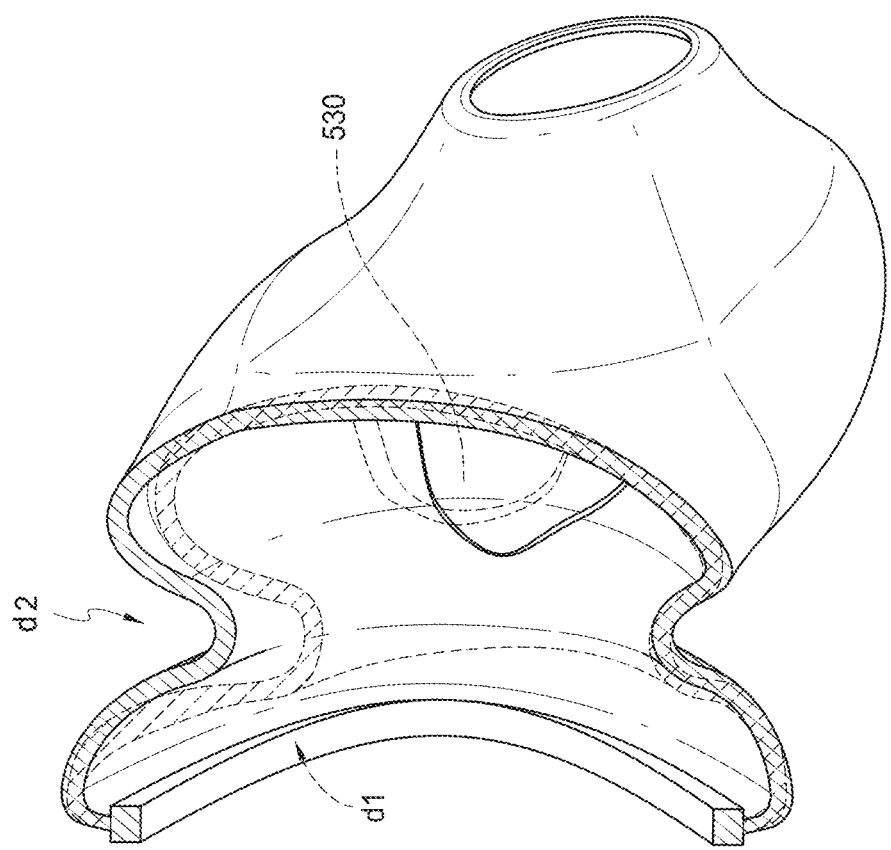
FIG. 58 is a side cross sectional view of another example embodiment of a seal including a bellows.

In the embodiment of FIG. 58, a depth d2 of the bellows structure is reduced at the front of the seal compared to the depth d1 of the bellows structure of the seal of FIGS. 57A-57B. The reduced depth can allow for more consistent compression of the lower bellows portion and bellows structure in use. An increased thickness zone 530, which can be similar to the region 530 of FIG. 41, can be sharply defined to allow visual confirmation of its placement relative to outer nostril.

Figure 59:
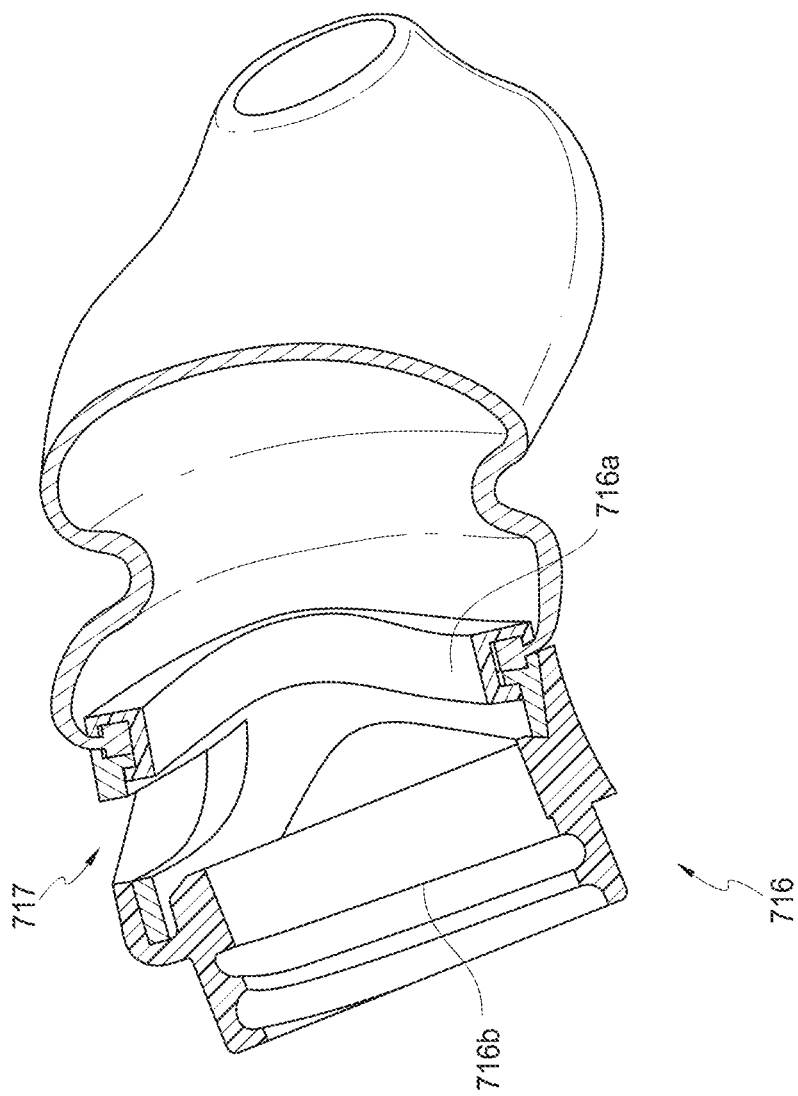
FIG. 59 is a side cross sectional view of another example embodiment of a seal including a bellows in combination with a seal clip and frame.

FIG. 59 illustrates an embodiment of a seal coupled to a frame assembly 716. The frame assembly 716 can be selectively coupled to a seal clip 716a that supports the seal. The frame assembly 716 can also define or include a conduit connector 716b that supports a conduit in use. In some embodiments, reducing a height of of the clip 716a that couples the seal to the frame 716 allows for more room for a central bias flow vent 717, allows the lower bellows portion to be moved farther away, e.g., by about 2 mm in some embodiments, from the patient's upper lip in use, and/or provides for a smoother transition from the seal to the frame assembly 716 to provide a smooth surface in the event the lower bellows portion contacts the patient's face during seal deflection due to hose tug in use. In some embodiments, the seal clips 716a include a bias feature 717, for example, a diffuser and/or bias holes. The bias feature 717 can allow for easier cleaning. In some embodiments, the lower bellows portion and/or bellows structure have a constant thickness, e.g., 1.0 mm, around the entire lower bellows portion and/or bellow structure to allow for consistent compression during use.

Figure 60A:
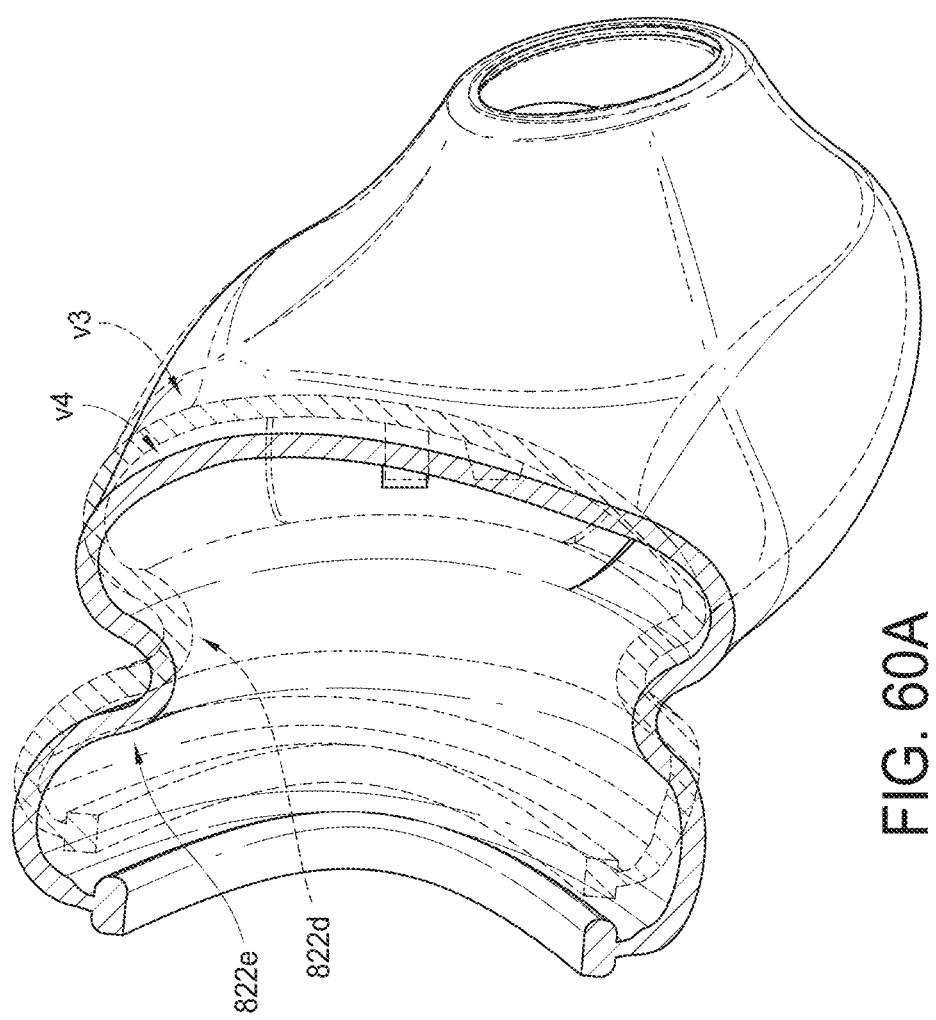
FIG. 60A is a side cross sectional view of another example embodiment of a seal including a bellows.
Figure 60B:
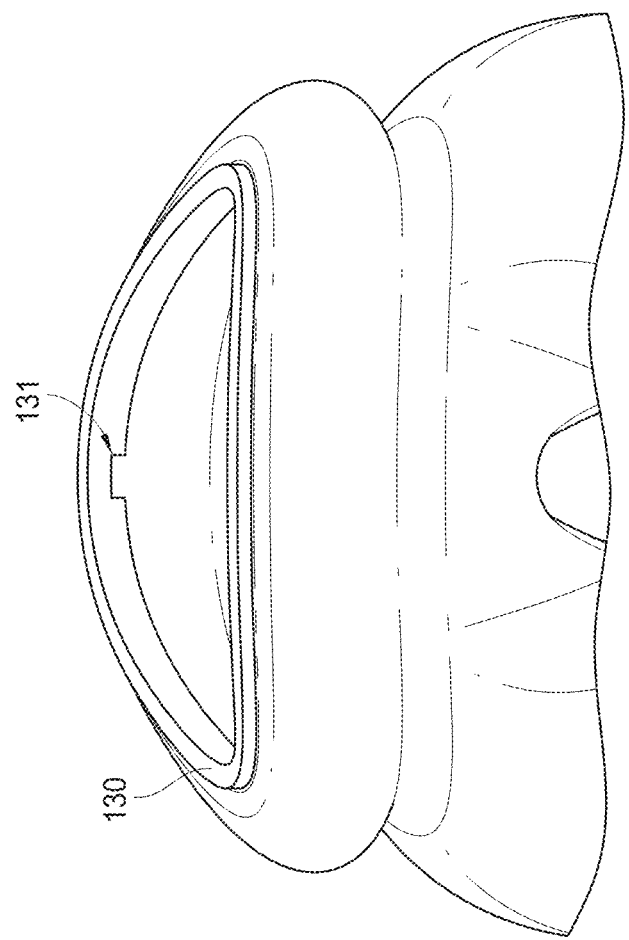
FIG. 60B is a partial view of the seal of FIG. 60A showing the bellows.

In the embodiment of FIGS. 60A-60B, the depth of the valley v4 between the prongs 120, 121 can be increased, for example, by 2 mm, compared to the depth of the valley v3 of the embodiment of FIGS. 58 and/or 59. The bellows structure 822e can be shifted away from the prongs 120, 121, for example, by 1 mm, compared to the bellows structure 822d of the embodiment of FIGS. 58 and/or 59. Shifting the bellows structure 822e away from the prongs 120, 121 can allow for a smoother radius in case the seal contacts the user's lip in use. An overall length of the seal can be increased, for example, by 3 mm to account for the deeper valley v4 and/or shifted bellows structure 822e. The increased length of the seal can allow for increased travel of the seal during use and a softer feel for the user. As shown in FIG. 60B, the inlet orifice 130 can include an alignment feature 131 to aid connection to the frame or conduit.

Figure 61A:
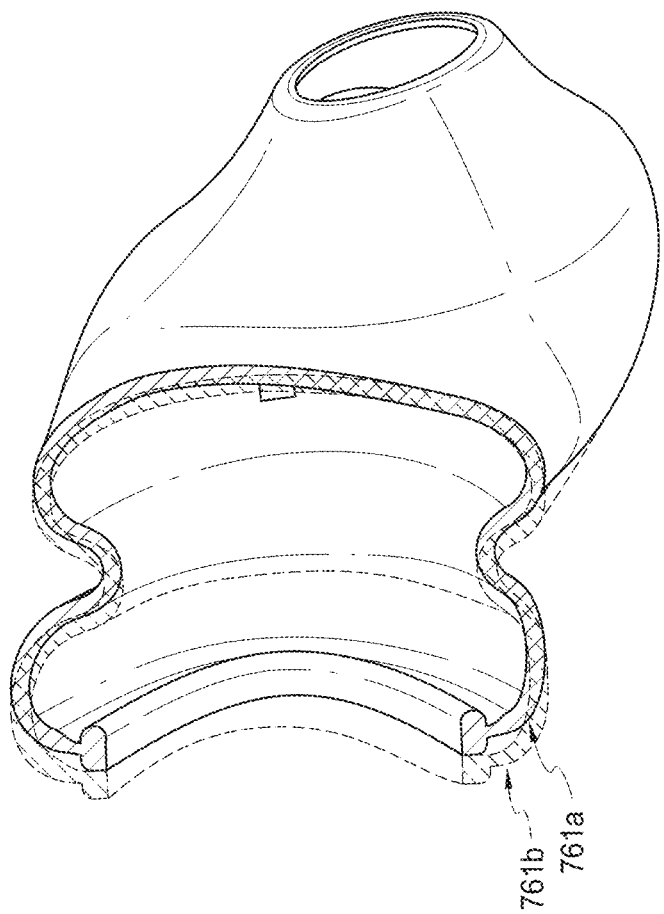
FIG. 61A is a side cross-sectional view of another example embodiment of a seal including a bellows.
Figure 61B:
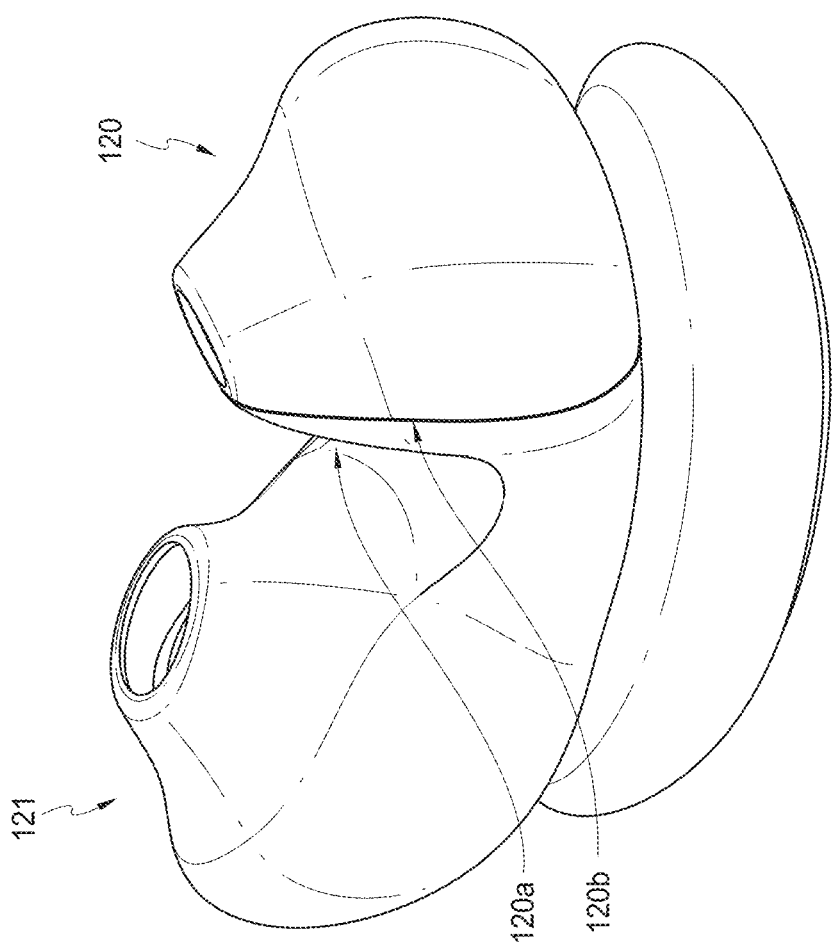
FIG. 61B is a perspective view of the seal of FIG. 61A.
Figure 61C:
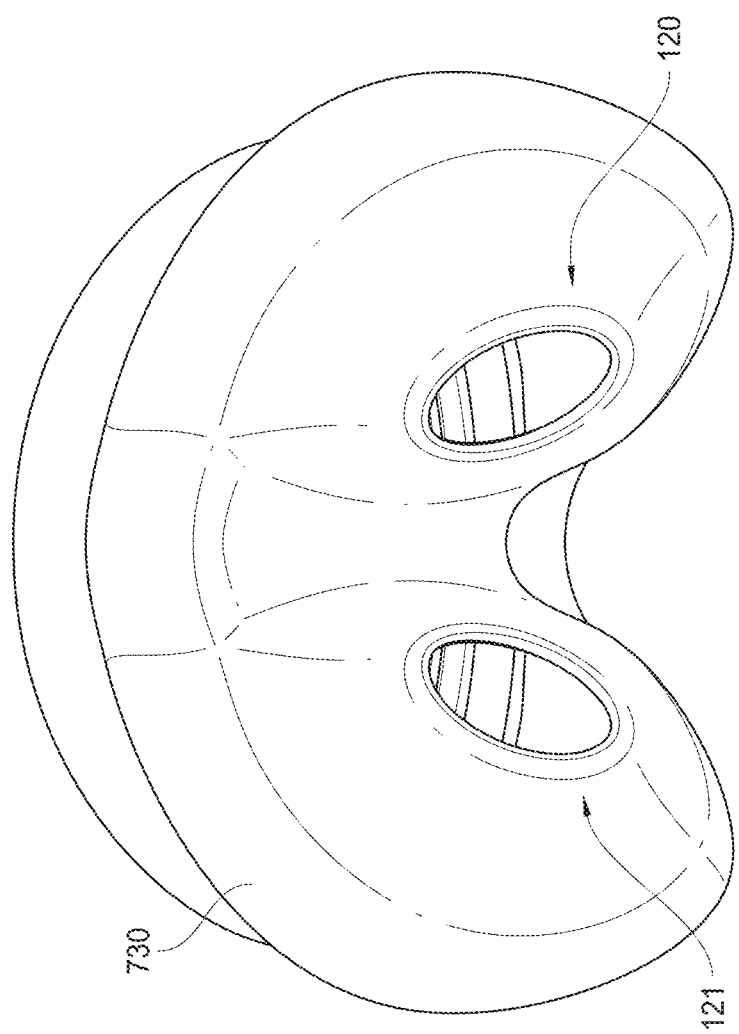
FIG. 61C is a front view of the seal of FIG. 61A.

In the embodiment of FIGS. 61A-61C, the prongs 120, 121 are more convex in the area configured to be positioned at or near the base of the patient's septum, for example as indicated at edge 120a compared to edge 120b. The seal can be shortened, for example as indicated by outline 761a compared to 761b, e.g., by 2 mm, without increasing the thickness of the lower bellows portion and/or bellows structure. Such a seal having a shorter length with constant thickness can provide a soft feel for the user, but the stiffness of the bellows structure can increase as the bellows structure is compressed in use. As shown in FIG. 61C, the seal can include a thickened region 730 extending across the front of the prongs 120, 121 or sealing surfaces. This thickened region can help prevent or inhibit the prongs 120, 121 from collapsing in use. In some embodiments, the thickened region is 1.0 mm thick and the remainder of the seal is 0.8 mm thick.

In the embodiment of FIGS. 62A-62B, the shape of the bellows structure 772 and/or lower bellows portion 770 matches or corresponds to the lower or rear surface of the sealing portion 760. The corresponding shapes can help the lower bellows portion 770 support the sealing portion 760. The bottom of the sealing portion 760 or underside of the prongs 120, 121, indicated by 712a in FIG. 62A, can be reduced in size, for example compared to the embodiment of FIGS. 57A-57B (e.g., by 1.5 mm in some embodiments). The embodiment of FIGS. 62A-62B can include the increased convex curvature in the area configured to be positioned at or near the base of the septum of the embodiment of FIGS. 61A-61C; this increased convex curvature region can allow the rear of the sealing portion or underside of the prongs 120, 121 to better engage the bottom of the patient's nostrils without an increase in the size of the underside of the prongs 120, 121 and/or without increasing the volume of the inner seal.

Seal with Rolling Section

Figure 43:
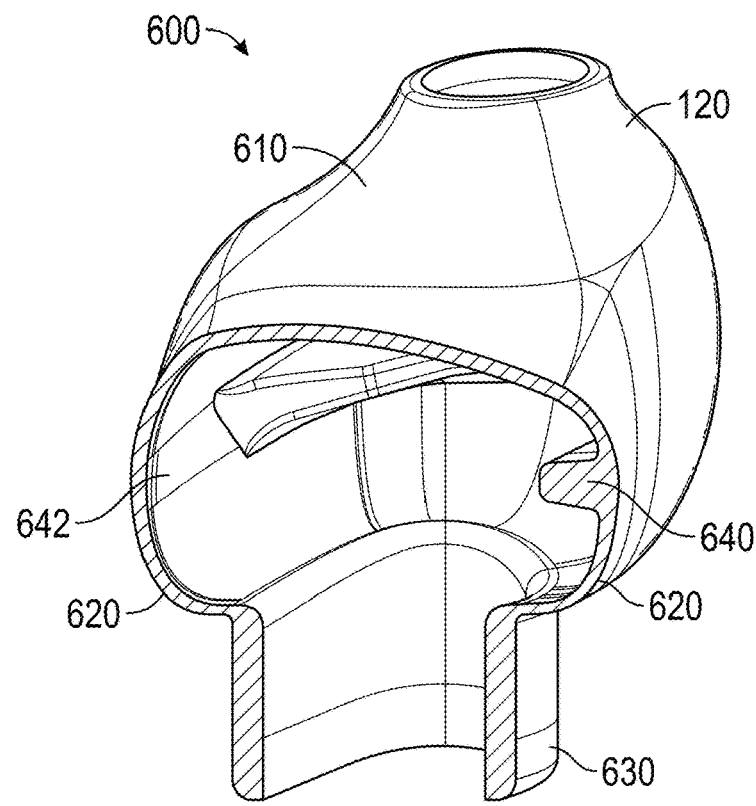
FIG. 43 is a sectional view of an example embodiment of a seal having a rolling section.
Figure 44:
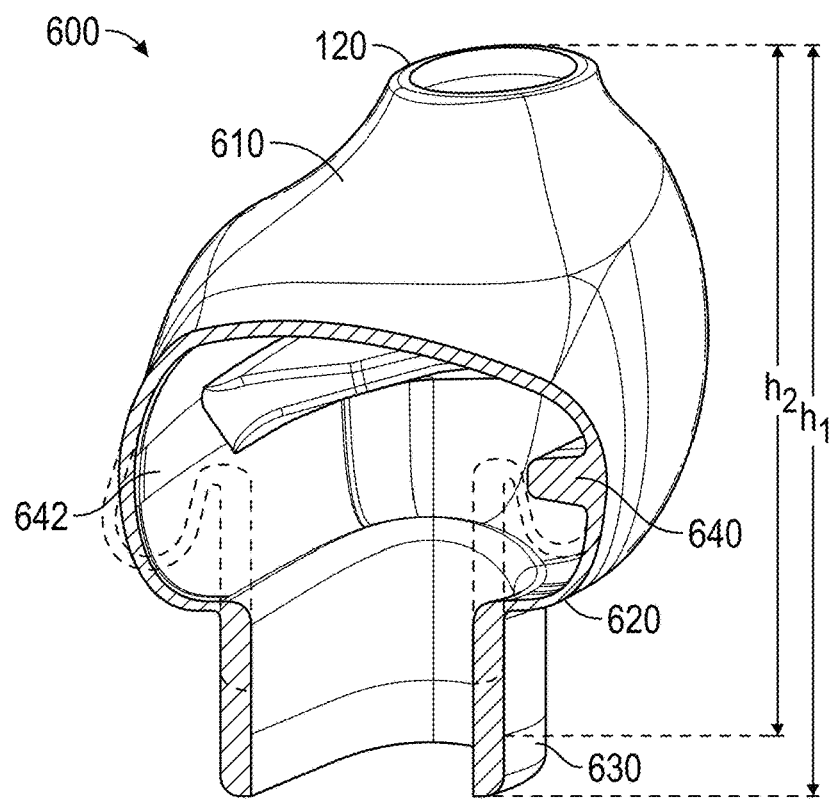
FIG. 44 is a sectional view of the seal of FIG. 43 showing an outline of the rolling section of the seal in a rolled state.
Figure 45:
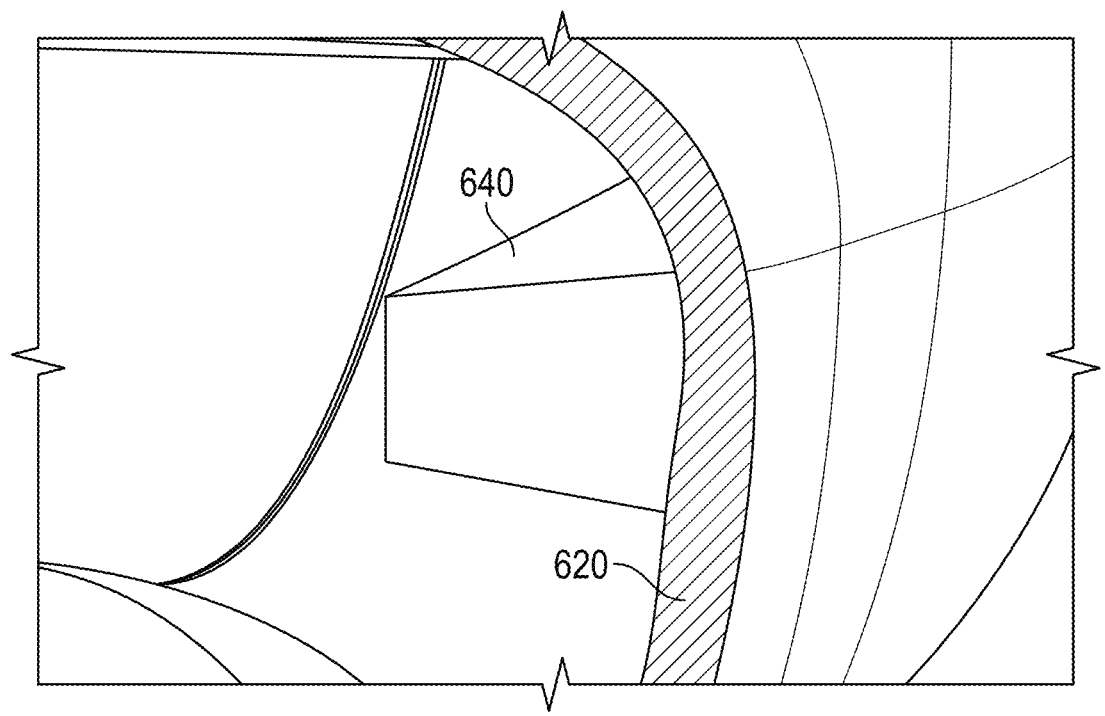
FIG. 45 is a detail view of a portion of a sectional view of the seal of FIG. 43 showing an internal rib.

FIGS. 43-54C illustrate an example embodiment of a seal 600 that includes a rolling section 620 between the sealing surface 610 and a connector receiving portion 630. The rolling section 620 can advantageously at least partially isolate the sealing surface 610 from hose drag forces. The rolling section 620 and sealing surface 610 are delimited or separated by a stiffener or stiffening member, such as a rib 640, that projects inwardly from an inner surface of the seal 600. The rolling section 620 is configured to roll over the connector receiving portion 630, as indicated by the dashed line profile in FIG. 44, to absorb or accommodate for forces on the connector receiving portion 630 and inhibit deformation of the sealing surface 610. In some embodiments, a height of the seal 600 in a neutral state, indicated by h1 in FIG. 44, is 34.5 mm. In some embodiments, a height of the seal 600 can decrease by approximately 5 mm or more when the rolling section 620 is rolled over the connector receiving portion 630. In some embodiments, the height of the seal 600 in a compressed state in which the rolling section 620 is rolled over the connector receiving portion 630, indicated by h2 in FIG. 44, is approximately 29.9 mm. In other configurations, the height may differ from that described above, but the relative amount of roll can remain the same.

The rib 640 can advantageously separate the rolling section 620 from the sealing surface 610 to help isolate movement of the connector receiving portion 630 from the sealing surface 610 and reduce or minimize the effect of hose drag. The rib 640 and/or rolling section 620 can also advantageously allow the sealing surface 610 to be positioned at differing angles relative to the connector receiving portion 630 such that the seal 600 can adapt to and accommodate varying facial geometries of different users. In some embodiments, the rib 640 is positioned approximately halfway between the sealing surface 610 (e.g., a portion of the sealing surface 610 between the prongs 120, 121) and the connector receiving portion 630.

The rib 640 can extend around an entire inner perimeter of the seal 600. In other embodiments, the rib 640 includes a gap 642 extending along at least a portion of the front of the seal 600 as shown in FIGS. 43-44. Once the rolling section 620 rolls over the connector receiving portion 630 to a certain extent, the rib 640 contacts internal surfaces of the rolling section 620 and/or the connector receiving portion 630 to prevent or inhibit further movement. In embodiments in which the rib 640 includes a gap 642 along the front of the seal 600, the gap allows the rolling section 620 in the front of the seal 600 to roll farther over the connector receiving portion 630 than the back of the seal 600. This allows for a greater travel or range of motion of the rolling portion 620 in the front of the seal 600 and the rolling section 620 in the front of the seal 600 may therefore not bottom out.

In some embodiments, the seal 600 is configured to be fitted to the user in use such that the rolling section 620 is at least partially rolled over the connector receiving portion 630 at least a majority of the time. This advantageously allows the connector receiving portion 630 to be pulled away from the sealing surface 610 to some extent without the sealing surface 610 losing contact with the user's nares.

In some embodiments, the rib 640 is made of silicone. In some embodiments, the rib 640 has an inner thickness (indicated by dimension Y in FIG. 45) in the range of 1 mm-4 mm, for example, 1.7 mm, an outer thickness (indicated by dimension Z in FIG. 45) in the range of 1 mm-5 mm, for example, 2.5 mm, and a length (indicated by dimension X in FIG. 45) in the range of 1 mm-6 mm, for example, 3 mm. The inner thickness can be less than the outer thickness. The length can be greater than the inner and outer thicknesses. In some embodiments, the rib 640 has rounded edges.

Figure 46:
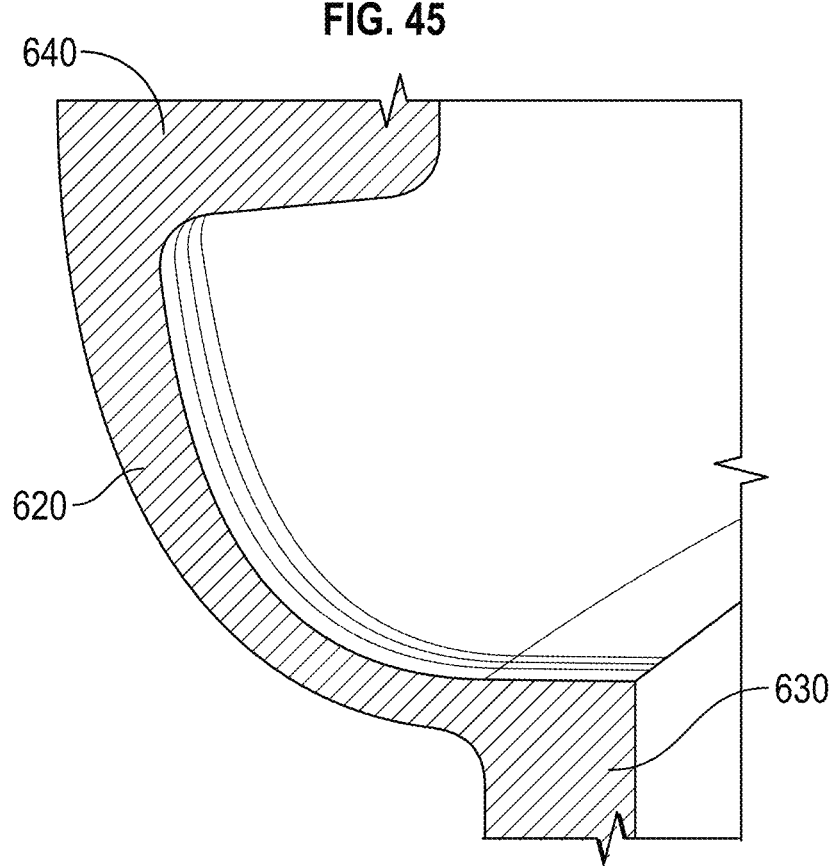
FIG. 46 is a detail view of a portion of a sectional view of the seal of FIG. 43 showing varying thickness in the rolling section.
Figure 47:
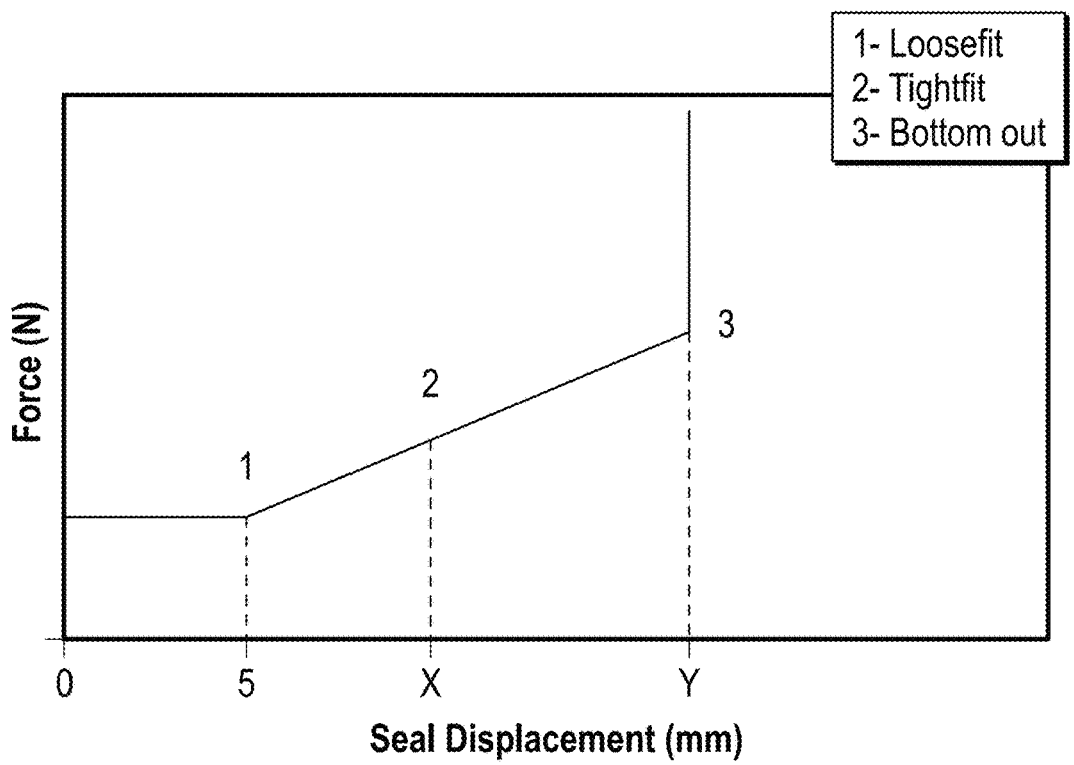
FIG. 47 is a theoretical force versus displacement profile of the seal of FIG. 43.
Figure 48:
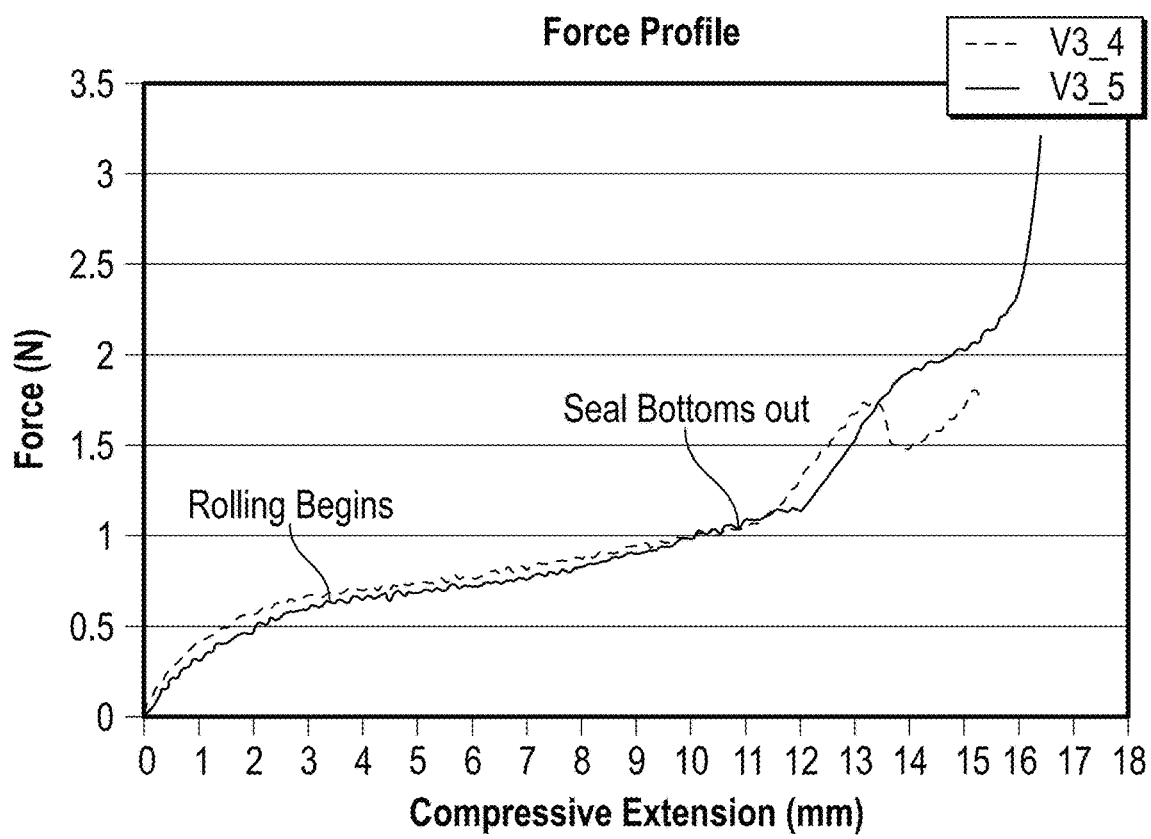
FIG. 48 shows a force profile of the seal of FIG. 43.
Figure 49:
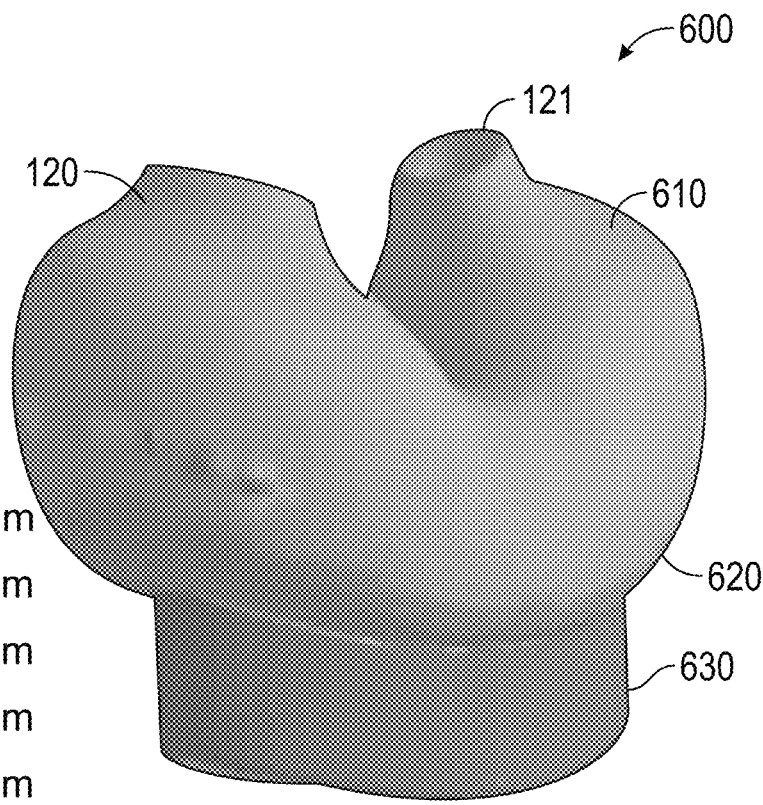
FIG. 49 shows a heat map illustrating the thickness of various regions of the seal of FIG. 43.

A thickness of the rolling section 620 can gradually transition between the rib 640 and the connector receiving portion 630 as shown in FIG. 46. For example, in some embodiments, the thickness transitions from 0.5 mm proximate or adjacent the connector receiving portion 630 to 0.8 mm proximate or adjacent the rib 640. In other configurations, the actual dimension may differ, but the proportions can be the same. The transitioning thickness advantageously allows the rolling section 620 to have a spring force that increases as the seal 600 becomes more compressed, which can help prevent or inhibit sharp increases in force that may be caused by the seal 600 suddenly bottoming out. This can advantageously improve user comfort. The force on the seal 600 increases substantially linearly as the rolling section 620 is displaced and remains relatively low until the rolling section 620 bottoms out, for example as shown in the theoretical force vs. displacement profile shown in FIG. 47 and force profile shown in FIG. 48. The thickness of the seal 600 can be consistent or constant throughout the sealing surface 610. In some embodiments, the thickness of the sealing surface 610 is 0.75 mm. FIG. 49 shows a heat map showing the generally constant thickness in the sealing surface 610 and varying thickness at the rib 640, rolling section 620, and connector receiving portion 630.

Figure 50A:
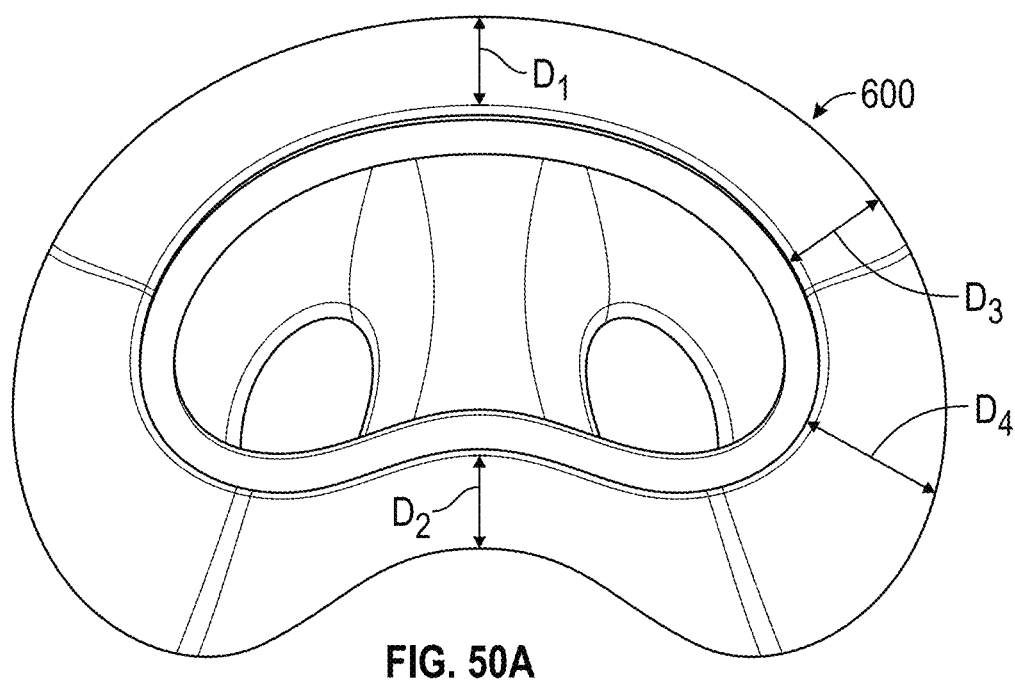
FIGS. 50A, 50B and 50C illustrate front elevational views of the seal of FIG. 43.
Figure 50B:
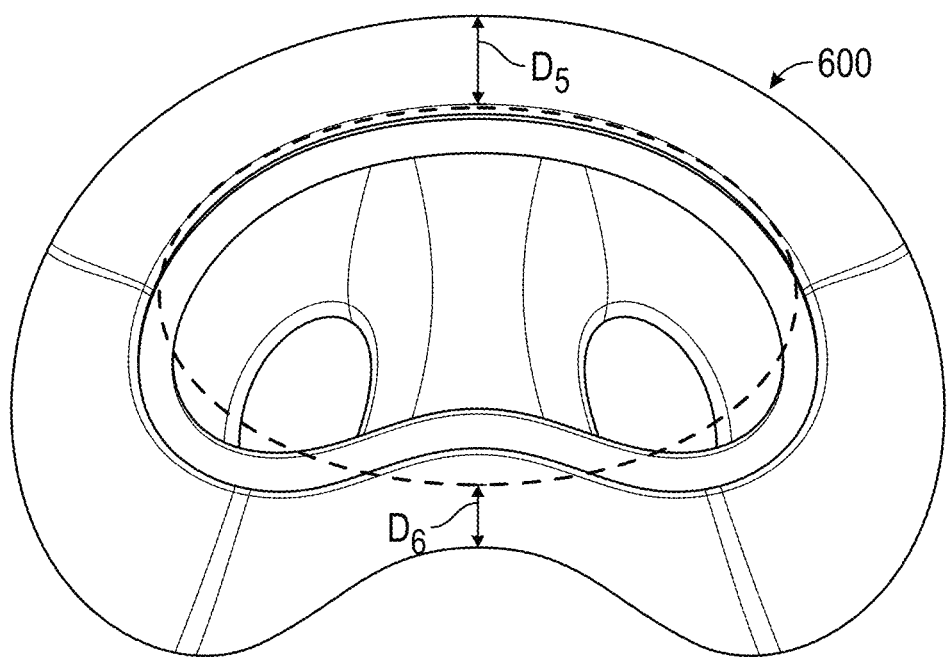
Figure 50C:
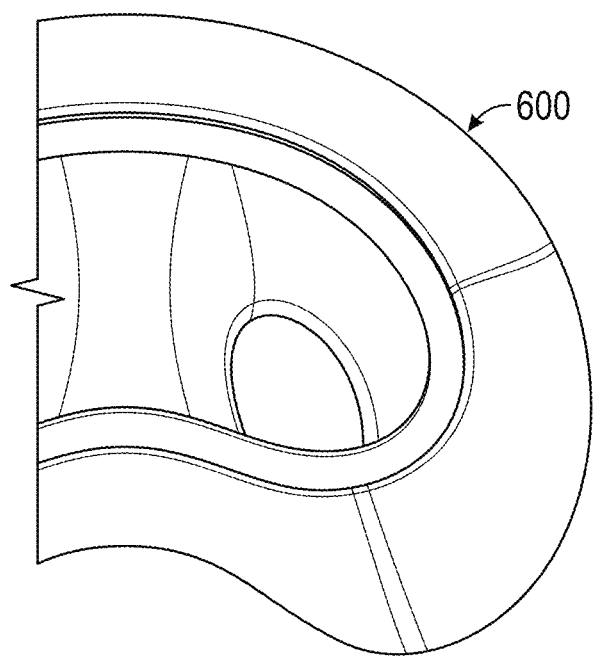
Figure 51:
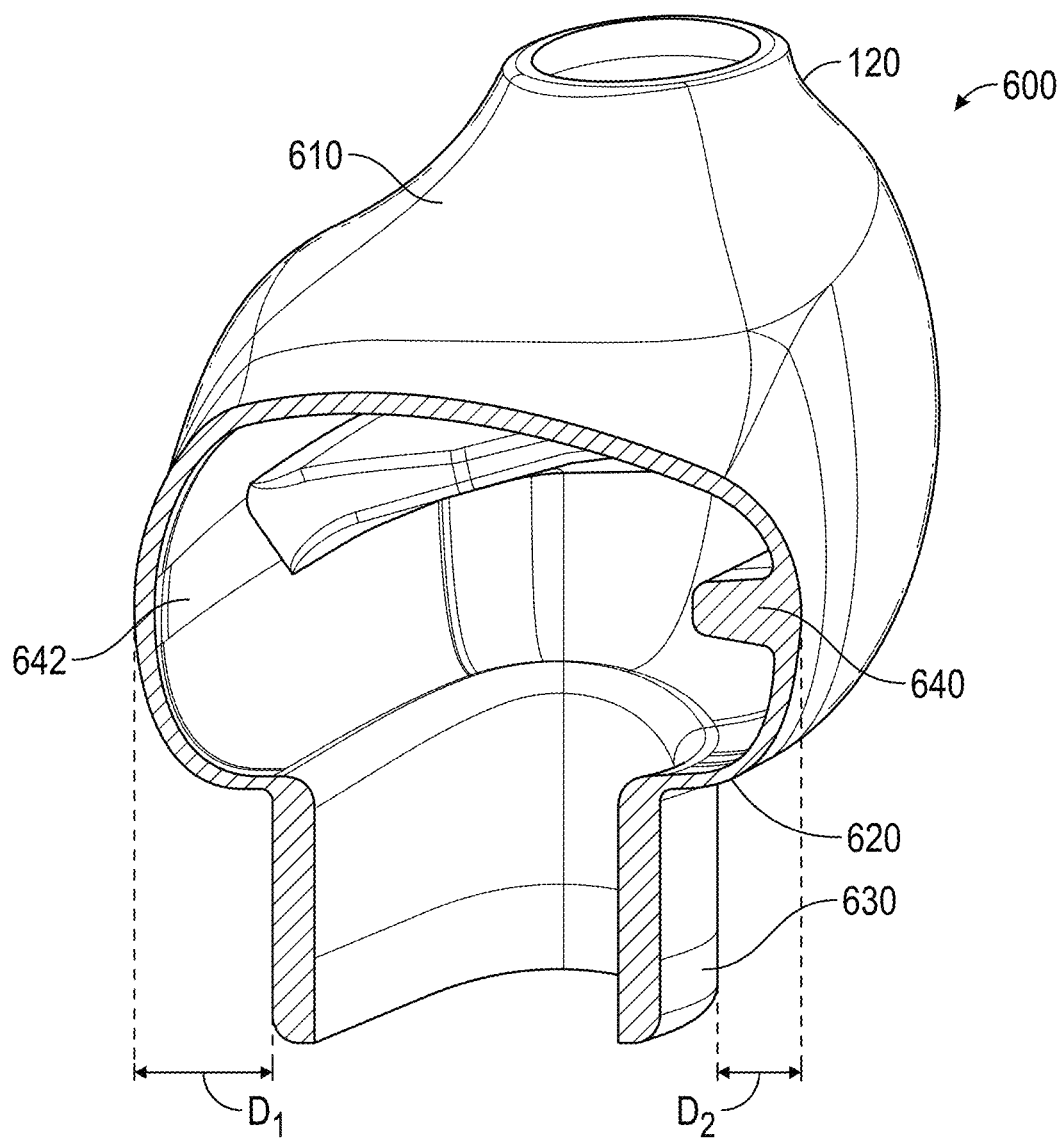
FIG. 51 is a sectional view of the seal of FIG. 43 showing a depth of the rolling section.

In some embodiments, the connector receiving portion 630 is generally kidney bean shaped and follows the overall shape of the seal 600 as shown in FIGS. 50A-50C. In such embodiments, the rolling section 620 extends outwardly from the connector receiving portion 630 a substantially or relatively more uniform depth or distance (indicated by the arrows in FIG. 50A as well as D1 and D2 in FIG. 51) around the entire perimeter or circumference of the seal 600. In contrast, if the connector receiving portion 630 had a generally oval shape, indicated by the dashed line in FIG. 50B, the rolling section 620 would have an uneven depth or distance as indicated by the arrows in FIG. 50B. A relatively more uniform depth of the rolling section 620, as provided by the kidney bean shaped connector receiving portion 630, advantageously allows the seal 600, e.g., the rolling section 620, to roll more evenly across the entire lower half of the seal 600 or around an entire perimeter or circumference of the seal 600.

Figure 52:
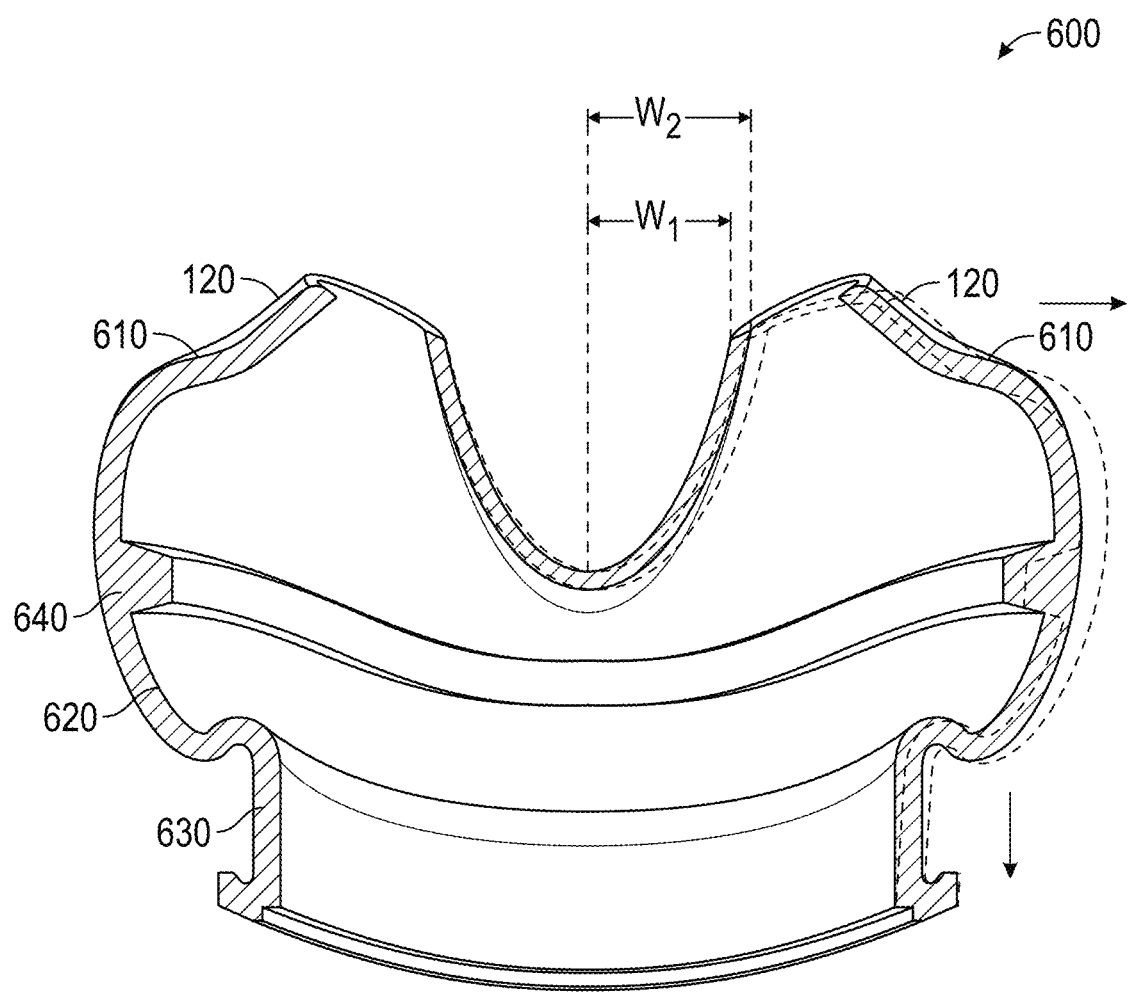
FIG. 52 is a sectional view of the seal of FIG. 43 showing an outline of the seal in a splayed state.
Figure 53A:
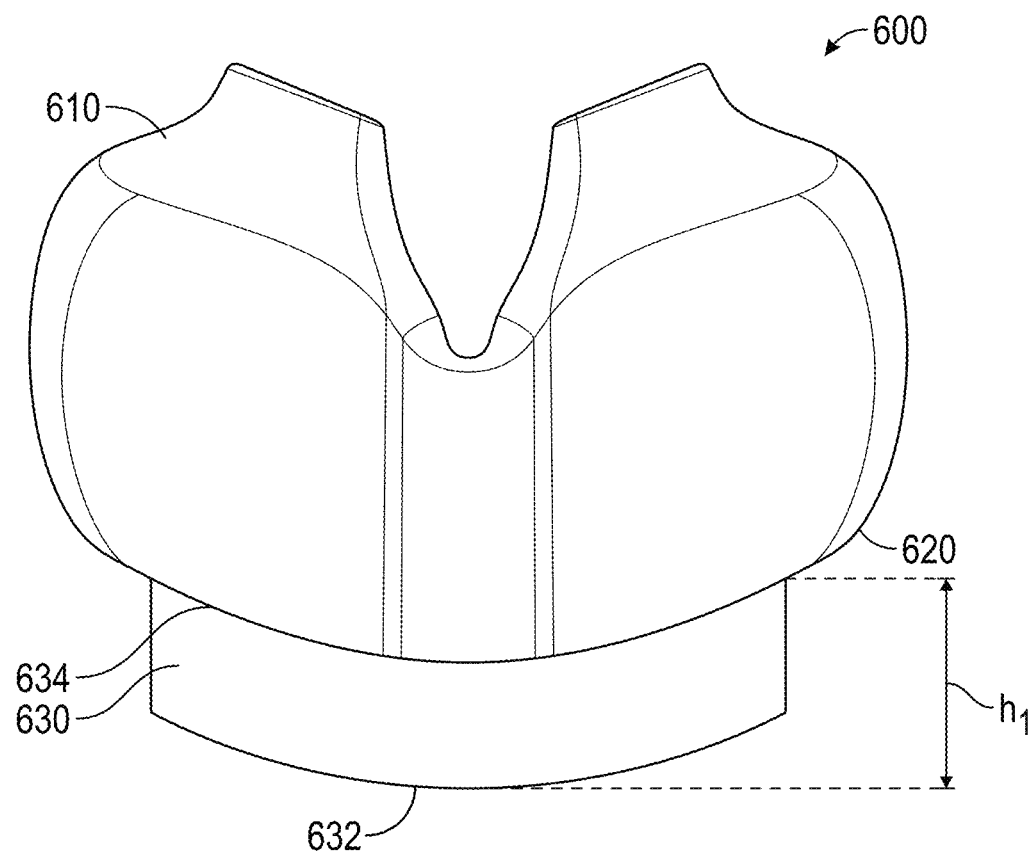
FIG. 53A is a top view of the seal of FIG. 43.
Figure 53B:
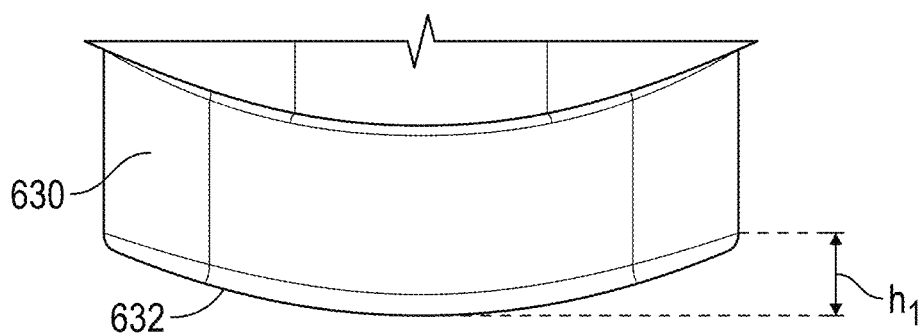
FIG. 53B is a detail view of a connector receiving portion of the seal of FIG. 43.
Figure 54A:
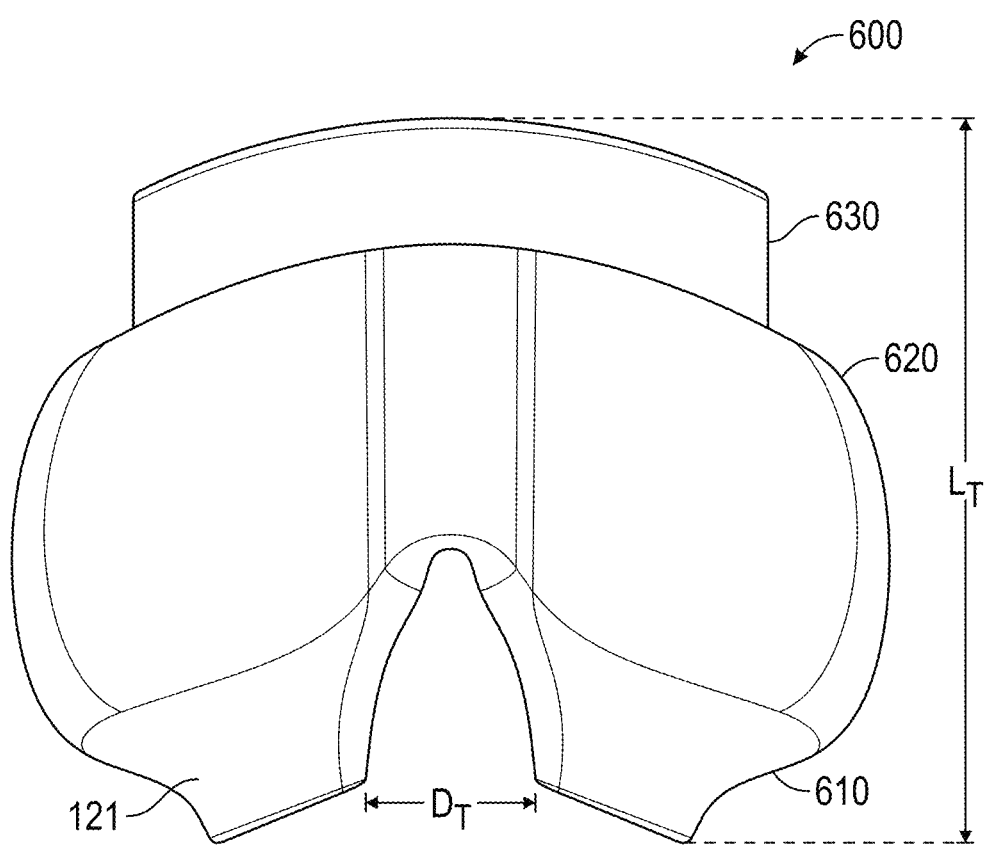
FIGS. 54A, 54B and 54C are various views of the seal of FIG. 43.
Figure 54B:
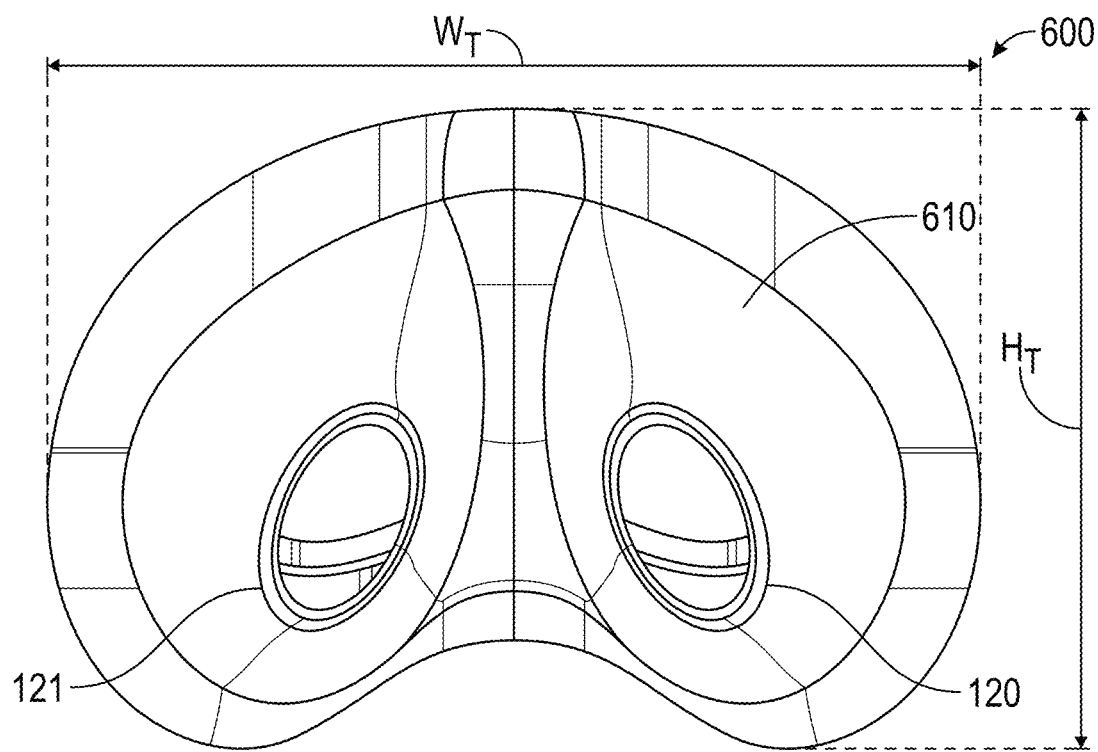
Figure 54C:
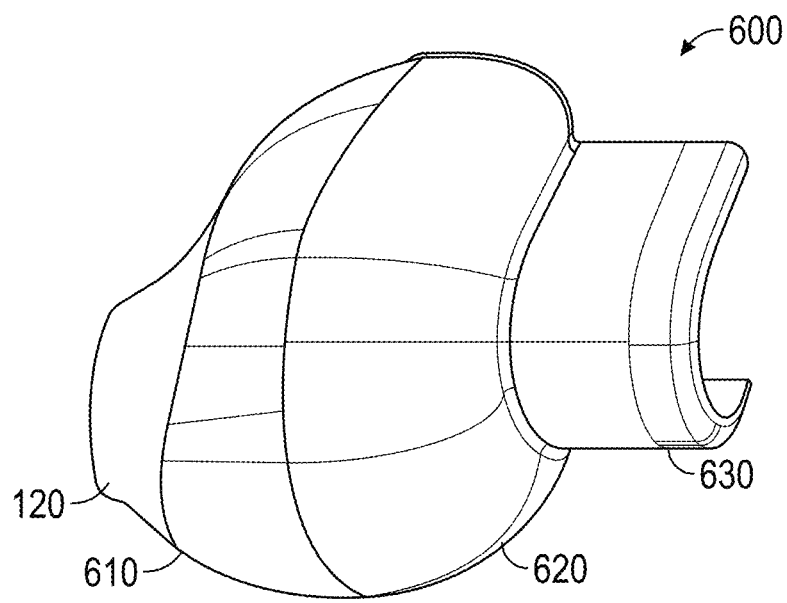

In some embodiments, the prongs 120, 121 can splay apart from each other to accommodate varying septum widths of different users as shown in FIG. 52. The rolling section 620 advantageously allows the prongs 120, 121 to splay apart without the sealing surfaces 610 collapsing or collapsing to a significant extent.

The connector receiving portion 630 extends from an intersection 634 with the rolling section 620 to an open base end 632 configured to receive, for example, a conduit or connector. In the illustrated embodiment, the open base end 632 and intersection 634 with the rolling section 620 are curved. The curvature of the intersection 634 can encourage consistent movement of the rolling section 620 around the perimeter or circumference of the seal 600. The curvature of the intersection 634 and/or base end 632 can also make the seal 600 shorter and/or give the seal 600 a relatively smaller appearance compared to a seal having a flat or straight intersection and/or base end. In some embodiments, the curvature is such that a distance (indicated by h1 in FIG. 53A) between a center of the base end 632 or intersection 634 and a lateral side of the base end 632 or intersection 634, respectively, along a line parallel to an axis extending through the center of the connector receiving portion 630 and between the prongs 120, 121 is approximately 3.26 mm.

Alternative Seals

Figure 63B:
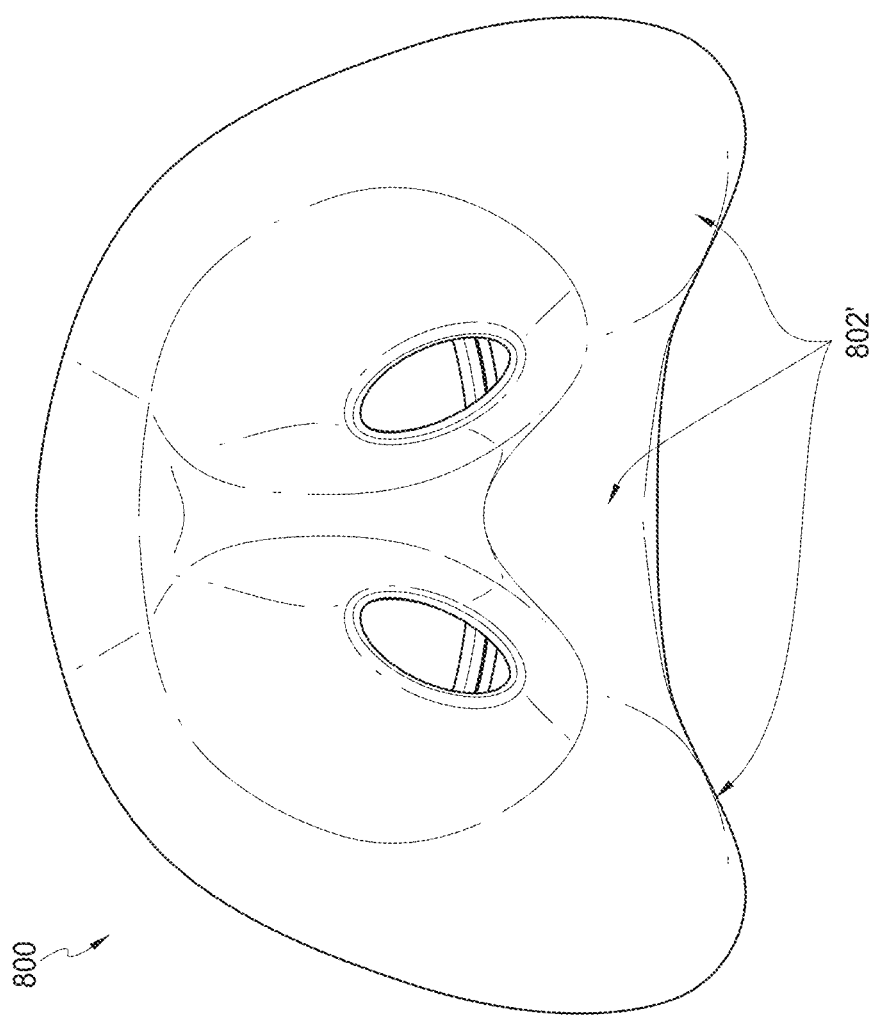
FIG. 63B is a front view of another example embodiment of a seal including support features.
Figure 63C:
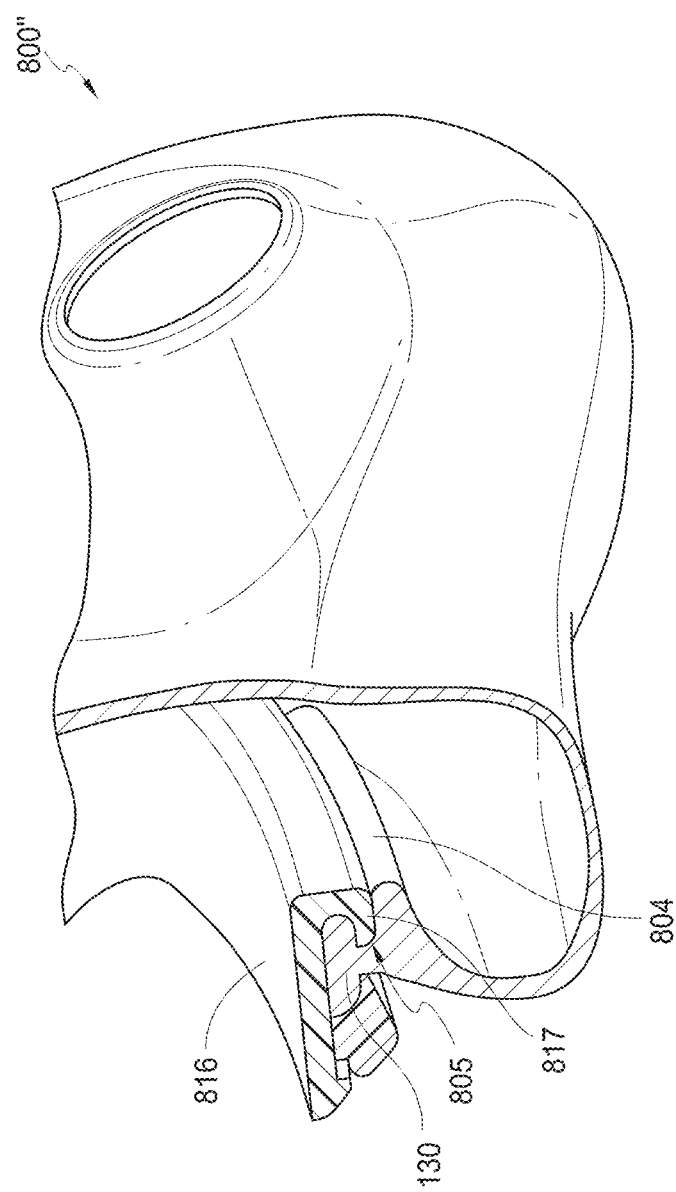
FIG. 63C is a partial side cross sectional view of an example embodiment of a seal including a seal clip.
Figure 63D:
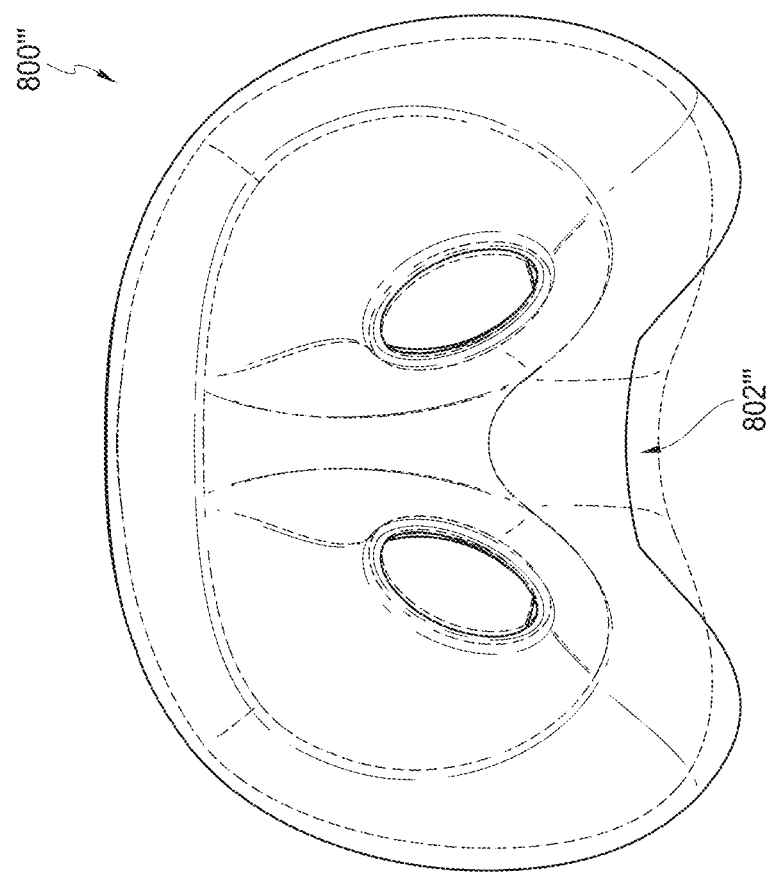
FIG. 63D is a front view of another example embodiment of seal including support features.

FIGS. 63A-63D illustrate additional alternative seal embodiments. As shown in FIG. 63A, the seal 800 can include support features 802 extending from lower portions on each side of the seal. In use, the support features 802 can contact the user's face at or near sides of the upper lip. In the seal 800' embodiment of FIG. 63B, the support features 802' are designed to be more evenly spread across the user's upper lip in use compared to the embodiment of FIG. 63A. The support features 802' can be shaped and sized to contact the outsides of the upper lip before the center, or the center of the upper lip before the sides, in use. In some embodiments, the depth of the valley between the prongs 120, 121 can be increased to allow the seal 800' to have increased lateral movement. FIG. 63D illustrates a seal 800''' having relatively more rounded and smooth support surfaces 802''', compared to, for example, the relatively more pointed or defined outer portions of the support features 802, 802' of the seals 800, 800' of FIGS. 63A-63B. In some embodiments, a center portion of the support surfaces 802''' can be lifted, e.g., by 3 mm in some embodiments, away from a position the center portion would otherwise be in if following the curvature of the side portions and/or away from the user's upper lip in use to avoid or reduce contact with the center of the upper lip in use.

In some embodiments, the support features 802, 802', 802''' can have a thickness of 1.0 mm and the remainder of the seal, or substantially the remainder of the seal, including the prongs, can have a thickness of 0.8 mm. In some embodiments, the support features 802, 802', 802''' can have a thickness of 0.4 mm and the remainder of the seal, or substantially the remainder of the seal, including the prongs, can have a thickness of 0.8 mm. In some embodiments, the support features 802, 802', 802''' can have a thickness of 0.5 mm, the prongs can have a thickness of 0.7 mm, and the remainder of the seal, or substantially the remainder of the seal, can have a thickness of 0.8 mm. In some embodiments, the sealing surfaces 802, 802', 802''' or an area of the seal that contacts or is placed adjacent or near the patient's upper lip in use has a thickness of 0.2 mm.

In some embodiments, for example as shown in FIG. 63C, the seal 800'' can include a support ledge 804 proximate the inlet orifice 130. As described above, in some embodiments, the inlet orifice 130 includes a rigid oval ring that defines the inlet orifice and acts as a connector for e.g., a frame or conduit. The support ledge 804 can support seal clips 816, a frame, or a conduit coupled to the inlet orifice 130. In the illustrated embodiment, a recess 805 is formed between the inlet orifice 130 and the support ledge 804. The recess 805 can receive a lip or flange 817 of, for example, a seal clip 816.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavor in any country in the world.

The inventions disclosed herein may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the inventions and without diminishing its attendant advantages. For instance, various components may be repositioned as desired. It is therefore intended that such changes and modifications be included within the scope of the inventions. Moreover, not all of the features, aspects and advantages are necessarily required to practice the present inventions. Accordingly, the scope of some of the present inventions is intended to be defined only by the claims that follow.

What is claimed is:

1. A nasal seal comprising:
   a sealing portion including:
      a first nostril prong,
      a second nostril prong, and
      a sealing surface;

an inlet orifice;
a bellows structure extending between the inlet orifice and the sealing portion, the bellows structure comprising:
a bellows portion; and
a lower bellows portion extending between the inlet orifice and the bellows portion, wherein the lower bellows portion defines a radial dimension in a direction radially outward from the inlet orifice to a maximal extent of the lower bellows portion
wherein the radial dimension of a side of the lower bellows portion located towards a patient is larger than the radial dimension of a side of the lower bellows portion located away from the patient; and
wherein the bellows structure extends circumferentially around the sealing portion.

2. The nasal seal according to claim 1, wherein the sealing portion comprises a lower surface having a curvature that substantially matches the curvature of the lower bellows portion.

3. The nasal seal according to claim 1, wherein a distance between the lower bellows portion and a lower surface of the sealing portion is the same around an entire circumference of the sealing portion.

4. The nasal seal according to claim 1, wherein the bellows structure has a consistent cross-section around an entire circumference of the sealing portion.

5. The nasal seal according to claim 1, wherein the sealing portion includes a thickened region extending along a front of the sealing surface and/or the first nostril prong and the second nostril prong.

6. The nasal seal according to claim 1, wherein the sealing portion includes various thickness regions.

7. The nasal seal of claim 6 wherein a thickness of the various thickness regions is selected such that the lower bellows portion and/or bellows region compress before the sealing surface in use.

8. The nasal seal according to claim 6, wherein a first region including the bellows structure has a thickness in a range of about 0.7 mm to about 1.0 mm, a second region including a base of the first nostril prong and the second nostril prong that has a thickness in a range of about 0.9 mm to about 1.1 mm, and/or a third region including the sealing surface has a thickness in the range of about 0.7 mm to about 0.8 mm.

9. Nasal seal according to claim 1, wherein the lower bellows portion and/or bellows region has a constant thickness.

10. The nasal seal according to claim 1, wherein the inlet orifice has an oval shape.

11. The nasal seal according to claim 1, wherein the inlet orifice includes a rigid oval ring configured to act as a connector.

12. The nasal seal according to claim 1, wherein a base of the first nostril prong and the second nostril prong is flat or substantially flat.

13. The nasal seal according to claim 1, wherein an outer perimeter of the lower bellows portion is larger and/or wider than a perimeter of the sealing portion.

14. The nasal seal according to claim 1, wherein a width of the inlet orifice is the same as a width of the sealing surface.

* * * * *